(12) United States Patent
Zhang et al.

(10) Patent No.: US 11,293,923 B2
(45) Date of Patent: Apr. 5, 2022

(54) S-LAYER PROTEIN 2D LATTICE COUPLED DETERGENT-FREE GPCR BIOELECTRONIC INTERFACES, DEVICES, AND METHODS FOR THE USE THEREOF

(71) Applicant: Massachusetts Institute of Technology, Cambridge, MA (US)

(72) Inventors: Shuguang Zhang, Lexington, MA (US); Rui Qing, Somerville, MA (US); Andreas Breitwieser, Vienna (AT); Uwe Sleytr, Vienna (AT)

(73) Assignee: Massachusetts Institute of Technology, Cambridge, MA (US)

( * ) Notice: Subject to any disclaimer, the term of this patent is extended or adjusted under 35 U.S.C. 154(b) by 71 days.

(21) Appl. No.: 16/118,989

(22) Filed: Aug. 31, 2018

(65) Prior Publication Data
US 2019/0353654 A1 Nov. 21, 2019

Related U.S. Application Data

(60) Provisional application No. 62/553,266, filed on Sep. 1, 2017, provisional application No. 62/570,174, filed on Oct. 10, 2017.

(51) Int. Cl.
*G01N 33/566* (2006.01)
*C07K 14/705* (2006.01)
(Continued)

(52) U.S. Cl.
CPC .......... *G01N 33/566* (2013.01); *C07K 14/32* (2013.01); *C07K 14/36* (2013.01); *C07K 14/705* (2013.01); *C07K 14/7158* (2013.01); *C07K 17/14* (2013.01); *C12N 15/70* (2013.01); *G01N 33/551* (2013.01); *G01N 33/6863* (2013.01); *C07K 2319/00* (2013.01); *C07K 2319/30* (2013.01); *G01N 2333/7158* (2013.01)

(58) Field of Classification Search
None
See application file for complete search history.

(56) References Cited

U.S. PATENT DOCUMENTS

| 7,262,281 B2 | 8/2007 | Sleytr et al. |
| 2004/0137527 A1 | 7/2004 | Sleytr et al. |
| (Continued) | | |

FOREIGN PATENT DOCUMENTS

| WO | 2008058302 A1 | 5/2008 | |
| WO | WO-2008058302 A1 * | 5/2008 | ............ B01D 69/02 |

OTHER PUBLICATIONS

Schuster et al., Biomimetic interfaces based on S-layer proteins, lipid membranes and functional biomolecules, J. R. Soc. Interface 11:20140232, Jan. 20, 2014 (Year: 2014).*

(Continued)

*Primary Examiner* — Rebecca M Giere
*Assistant Examiner* — Xiaoyan Zou
(74) *Attorney, Agent, or Firm* — Elmore Patent Law Group, P.C.; Carolyn Elmore; Mahreen Hoda

(57) ABSTRACT

The invention includes a bioelectronic interface comprising a self-assembling unit, wherein the self-assembling unit comprises a variant GPCR fusion protein bound to an S-layer fusion protein. The invention also encompasses a biosensor or device comprising the bioelectronic interface and methods of screening for a ligand of a GPCR.

25 Claims, 37 Drawing Sheets
Specification includes a Sequence Listing.

(51) Int. Cl.
       C07K 17/14      (2006.01)
       C07K 14/32      (2006.01)
       C07K 14/36      (2006.01)
       C12N 15/70      (2006.01)
       G01N 33/551     (2006.01)
       G01N 33/68      (2006.01)
       C07K 14/715     (2006.01)

(56) References Cited

U.S. PATENT DOCUMENTS

| | | | |
|---|---|---|---|
| 2007/0042954 | A1 | 2/2007 | Chen et al. |
| 2012/0025271 | A1 | 2/2012 | Nakano |
| 2012/0252719 | A1 | 10/2012 | Zhang et al. |
| 2014/0113370 | A1* | 4/2014 | Camphausen ......... C07K 16/40 435/328 |
| 2014/0364330 | A1* | 12/2014 | Mershin ............... G01N 21/553 506/9 |
| 2015/0370960 | A1 | 12/2015 | Zhang et al. |
| 2015/0370961 | A1* | 12/2015 | Zhang .................... G16B 35/00 506/8 |
| 2015/0376261 | A1 | 12/2015 | Steyaert et al. |
| 2016/0123919 | A1* | 5/2016 | Johnson ................. C23C 16/44 506/38 |

OTHER PUBLICATIONS

Ilk et al., Surfaces functionalized with self-assembling S-layer fusion proteins fornanobiotechnological applications, Colloids and Surfaces A: Physicochem. Eng. Aspects 321 (2008) 163-167. (Year: 2008).*
Neumann et al., Functional immobilization of a ligand-activated G-protein-coupled receptor. ChemBio Chem. 2002;3:993-998. (Year: 2002).*
Vollenkle et al., Construction of a Functional S-Layer Fusion Protein Comprising an Immunoglobulin G-Binding Domain for Development of Specific Adsorbents for Extracorporeal Blood Purification, Applied and Environmental Microbiology, Mar. 2004, p. 1514-1521 (Year: 2004).*
Badelt-Iichtblau et al., Bioconjugate Chem. 2009, 20, 895-903 (Year: 2009).*
Sleytr, U. B. & Glauert, A. M. (1975) Analysis of regular arrays of subunits on bacterial surfaces: evidence for a dynamic process of assembly, J Ultrastruct Res. 50, 103-116.
Sleytr, U. B., et al., S-layers: principles and applications, FEMS Microbiol Rev. 38, 823-64 (2014).
Sleytr, U. B., et al., S-Layers as a tool kit for nanobiotechnological applications, FEMS Microbiol Lett. 267, 131-144 (2007).
Sleytr, U. B., Egelseer, E. M., Ilk, N., Pum, D. & Schuster, B. (2007) S-layers as a Basic Building Block in a Molecular Construction Kit, FEBS J. 274, 323-334.
Moll, D., Huber, C., Schlegel, B., Pum, D., Sleytr, U. B. & Sára, M. (2002) S-layer-streptavidin fusion proteins as template for nanopatterned molecular arrays, Proc Natl Acad Sci U S A. 99, 14646-51.
Huber, C., Egelseer, E. M., Ilk, N., Sleytr, U. B. & Sára, M. (2006) S-layer-streptavidin fusion proteins and S-layer-specific heteropolysaccharides as part of a biomolecular construction kit for application in nanobiotechnology, Microelectron Eng. 83, 1589-1593.
Vollenkle, C., et al., (2004) Construction of a functional S-layer fusion protein comprising an immunoglobulin G-binding domain for development of specific adsorbents for extracorporeal blood purification, Appl Environ Microbiol. 70, 1514-21.
Breitwieser, A., et al., (2002) A recombinant bacterial cell surface (S-layer)-major birch pollen allergen-fusion protein (rSbsC/Bet v1) maintains the ability to self- assemble into regularly structured monomolecular lattices and the functionality of the allergen, Protein Eng. 15, 243-9.
Sleytr, U. B. & Beveridge, T. J. (1999) Bacterial S-layers, Trends Microbiol. 7, 253-60.

Pum, D. & Sleytr, U. B. (1995) Monomolecular reassembly of a crystalline bacterial cell surface layer (S layer) on untreated and modified silicon surfaces, Supramol Sci. 2, 193-197.
Picher, M., et al., (2013) Nanobiotechnology advanced antifouling surfaces for the continuous electrochemical monitoring of glucose in whole blood using a lab-on-a-chip, Lab Chip. 13, 1780-9.
Rothbauer, M., et al., (2013) Exploitation of S-layer anisotropy: pH-dependent nanolayer orientation for cellular micropatterning, ACS Nano. 7, 8020-30.
Sara, M. & Sleytr, U. B. (1987) Production and characteristics of ultrafiltration membranes with uniform pores from two-dimensional arrays of proteins, J Membr Sci. 33, 27-49.
Ilk, N., et al., (2002) Molecular characterization of the S-layer gene, sbpA, of Bacillus sphaericus CCM 2177 and production of a functional S-layer fusion protein with the ability to recrystallize in a defined orientation while presenting the fused allergen, Appl Environ Microbiol. 68, 3251-60.
Ilk, N., Egelseer, E. M. & Sleytr, U. B. (2011) S-layer fusion proteins—construction principles and applications, Curr Opin Biotechnol. 22, 824-831.
Breitwieser, A., Pum, D., Toca-Herrera, J.L. Sleytr, U.B (2016) Magnetic beads functionalized with recombinant S-layer protein exhibit high human IgG-binding and anti-fouling properties, Current Topics in Peptide & Protein Research. 17, 45-55.
Huber, C., et al., (2006) Heterotetramers formed by an S-layer-streptavidin fusion protein and core-streptavidin as nanoarrayed template for biochip development., Small. 2, 142-150.
Ucisik, M. et al., (2015) S-layer fusion protein as a tool functionalizing emulsomes and CurcuEmulsomes for antibody binding and targeting, Colloids Surf B Biointerfaces. 128, 132-9.
Gyorvary, E. S., et al., (2003) Self-assembly and recrystallization of bacterial S-layer proteins at silicon supports imaged in real time by atomic force microscopy, J Microsc. 212, 300-6.
Vinothkumar, K.R., et al. Structures of membrane proteins. Quarterly Reviews of Biophysics 43, 65-158 (2010).
Lv, X. et al. In vitro expression and analysis of the 826 human G protein-coupled receptors. Protein Cell 7, 325-337 (2016).
Scott, D.J., et al., Stabilizing membrane proteins through protein engineering. Current Opinion in Chemical Biology 17, 427-435 (2013).
Hardy, D., et al., Overcoming bottlenecks in the membrane protein structural biology pipeline. Biochem. Soc. Trans. 44, 838-844 (2016).
Mizrachi, D. et al., Making water-soluble integral membrane proteins in vivo using an amphipathic protein fusion strategy. Nature Commun. 6, 6826. (2015).
Slovic, A.M. et al., Computational design of a water-soluble analog of phospholamban. Protein Science 12, 337-348 (2003).
Slovic, A.M. et al., Computational design of water-soluble analogues of the potassium channel KcsA. Proc. Natl. Acad. Sci USA. 101, 1828-1833 (2004).
Slovic, A.M. et al., X-ray structure of a water-soluble analog of the membrane protein phospholamban: sequence determinants defining the topology of tetrameric and pentameric coiled coils. J. Mol. Biol. 348, 777-787 (2005).
Perez-Aguilar, J.M. et al., A computationally designed water-soluble variant of a G-protein-coupled receptor: the human mu opioid receptor. PLoS ONE 8, e66009 (2013).
Zhao, X. et al., Characterization of a computationally designed water-soluble human μ-opioid receptor variant using available structural information. Anesthesiology 121, 866-875 (2014).
Thomson, A.R. et al., Computational design of water-soluble a-helical barrels. Science 346, 485-488 (2014).
Huang, P.S., et al., The coming age of de novo protein design. Nature 537, 320-327 (2016).
Fersht, A. (1998) Structure and Mechanism in Protein Science: A guide to enzyme catalysis and protein folding. W. H. Freeman, New York, pp. 10-13, 523-532.
Wu, B. et al. Structures of the CXCR4 chemokine GPCR with small-molecule and cyclic peptide antagonists. Science 330, 1066-1071 (2010).

(56) References Cited

OTHER PUBLICATIONS

Perutz, M.F., et al., Structure of haemoglobin: a three-dimensional Fourier synthesis at 5.5Å resolution, obtained by X-ray analysis. Nature 185, 416-422 (1960).
Weed, R.I., Reed, C.F. & Berg, G. Is hemoglobin an essential structural component of human erythrocyte membranes? J Clin Invest. 42, 581-588 (1963).
Fersht, A., et al., Enzyme hyperspecificity: rejection of threonine by the Valyl-trna synthetase by misacylation and hydrolytic editing. Biochemistry, 15, 3342-3346 (1976).
Lin, L., et al., Schimmel, P. Aminoacylation error correction. Nature 384, 33-34 (1996).
Lin, L. & Schimmel, P. Mutational analysis suggests the same design for editing activities of two tRNA synthetases. Biochemistry 35, 5596-5601 (1996).
Chou, P.Y., Empirical Predictions of Protein Conformation. Ann. Rev. Biochemistry 47, 251-276. (1978).
Shavit, RB., G-Protein-Coupled Receptors in Cancer, International Journal of Molecular Sciences, vol. 17, pp. 1-16 (2016).
O'Hayre, M., et al., Novel insights into G protein and G protein-coupled receptor signaling in cancer. Curr Opin Cell Biol 27, 126-35 (2014).
Halvorsen, E.C. et al. Maraviroc decreases CCL8-mediated migration of CCR5(+) regulatory T cells and reduces metastatic tumor growth in the lungs. Oncoimmunology 5, e 1150398 (2016).
Babcock, G.J., et al., Ligand binding characteristics of CXCR4 incorporated into paramagnetic proteoliposomes. J. Bio. Chem. 276, 38433-38440 (2001).
Stenlund, P., et al., Capture and reconstitution of G protein-coupled receptors on a biosensor surface Analytical Biochemistry 316, 243-250 (2003).
Navratilova, I., et al., Solubilization, stabilization, and purification of chemokine receptors using biosensor technology. Analytical Biochemistry 339, 271-281 (2005).
Navratilova, I., et al., Analyzing ligand and small molecule binding activity of solubilized GPCRs using biosensor technology. Analytical Biochemistry 355, 132-139 (2006).
Oberlin, E. et al. The CXC chemokine SDF-1 is the ligand for LESTR/fusin and prevents infection by T-cell-line-adapted HIV-1. Nature 382, 833-835 (1996).
Bleul, et al. The HIV co-receptors CXCR4 and CCR5 are differentially expressed and regulated on human T lymphocytes. Proc. Natl. Acad. Sci. USA, 94, 1925-1930 (1997).
Jin, J. et al., Targeting spare CC chemokine receptor 5 (CCR5) as a principle to inhibit HIV-1 entry. J. Biol. Chem. 289, 19042-19052, (2014).
Tan, Q. et al. Structure of the CCR5 chemokine receptor-HIV entry inhibitor maraviroc complex. Science 341, 138seven-1390 (2013).
Fields, S. et al., A novel genetic system to detect protein-protein interactions. Nature 340, 245-246 (1989).
Li, J., et al., W. Development of a membrane-anchored ligand and receptor yeast two-hybrid system for ligand-receptor interaction identification. Scientific Reports 6, 35631. (2016).
Eble, J.A., et al., A. alpha 2beta 1 integrin is not recognized by rhodocytin but is the specific, high affinity target of rhodocetin, an RGD-independent disintegrin and potent inhibitor of cell adhesion to collagen. J. Biol. Chem. 276, 12274-12284 (2001).
Duhr, S., et al., Why molecules move along a temperature gradient. Proc Natl Acad Sci USA 103, 19678-19682 (2006).
Wienken, C.J., et al., Protein-binding assays in biological liquids using microscale thermophoresis. Nature Commun. 1, 100 (2010).
Gazit, E., Mechanisms of amyloid fibril self-assembly and inhibition: model short peptides as a key research tool, FEBS J 272, 5971-5978 (2005).
Wang, X. et al., Peptide surfactants for cell-free production of functional G protein-coupled receptors. Proc Natl Acad Sci 108, 9049-9054 (2011).
Corin, K. et al., Structure and function analyses of the purified GPCR human vomeronasal type 1 receptor 1. Sci Rep 1, 172 (2011).

Seidel, S.A. et al., Microscale thermophoresis quantifies biomolecular interactions under previously challenging conditions. Methods 59, 301-315 (2013).
Parker, J.L., Newstead, S. Molecular basis of nitrate uptake by the plant nitrate transporter NRT1.1. Nature 507, 68-72 (2014).
Tegler, L.T., et al., Cell-free expression, purification, and ligand-binding analysis of *Drosophila melanogaster* olfactory receptors DmOR67a, DmOR85b and DmORCO. Scientific Reports 5, 7867 (2015).
Moller, F.M., et al., Photochemical microscale electrophoresis allows fast quantification of biomolecule binding. J Am Chem Soc. 138, 5363-5370 (2016).
Sandal, M., et al. GOMoDo: A GPCRs Online Modeling and Docking Webserver. PLoS ONE 8: e74092 (2013).
Krieger, E., et al., Improving Physical Realism, Stereochemistry, and side-chain accuracy in homology modeling Four approaches that performed well in CASP8. Proteins. 77 Suppl. 9, 114-122 (2009).
Konagurthu, A.S., et al., A.M. Mustang: A multiple structural alignment algorithm. Proteins 64, 559-574 (2006).
Reshetnyak, Y.K., et al., E.A. Decomposition of protein tryptophan fluorescence spectra into log-normal components. II. The statistical proof of discreteness of tryptophan classes in proteins, Biophys J 81, 1710-1734 (2001).
Edelhoch, H., et al., Tyrosine fluorescence in proteins. Ann N Y Acad Sci, 158, 391-409 (1969).
Balabanian, K., et al., The chemokine SDF-1/CXCL12 binds to and signals through the orphan receptor RDC1 in T Tymphocytes. J Biol Chem 280: 35760-35766 (2005).
Naumann, U., et al., CXCR7 Functions as a Scavenger for CXCL12 and CXCL11. PLoS ONE 5, e9175 (2010).
Miao, Z., et al., CXCR7 (RDC1) promotes breast and lung tumor growth in vivo and is expressed on tumor-associated vasculature. Proc Natl Acad Sci USA 104, 15735-15740 (2007).
Xiong, N., et al., CCR10 and its ligand in regulation of epithelial immunity and diseases. Protein Cell 3, 571-580 (2012).
Pan, et al., A novel chemokine ligand for CCR10 and CCR3 expressed by epithelial cells in mucosal tissues. J. Immul. 165, 2943-2949 (2000).
Wang, et al., Identification of a Novel Chemokine (CCL28), which Binds CCR10 (GPR2) J. Biol. Chem. 275, 22313-22323 (2000).
Bemredjem, B., et al., Mutational Analysis of atypical chemokine receptors (ACKR3/CXCR7) interaction with its chemokine ligands CXCL11 and CXCL12. J. Biol. Chem. 292, 31-42 (2017).
Navratilova, I., Sodroski, J., Myszka, D.G. Solubilization, stabilization, and purifcation of chemokine receptors using biosensor technology. Analytical Biochemistry 339, 271-281 (2005).
Witte, M.D., et al., "Preparation of Unnatural N-to-N and C-to-C Protein Fusions," PNAS, vol. 109 (30); pp. 11993-11998 (Jul. 2012).
Chen, et al. (2013), Adv Drug Deliv Rev 65(10): 1357-1369.
Lodish, et al., Chapter 3 (titled Protein Structure and Function) of Molecular Cell Biology $8^{th}$ Edition (2016).
Yu, K., et al., "Synthetic Fusion Protein Design and Applications," Biotechnology Advances, 33, pp. 155-164 (2015).
Schmidt, "Fusion Proteins: Applications and Challenges" in Fusion Protein Technologies for Biopharmaceuticals: Applications and Challenges, John Wiley & Sons, Inc. 2013, 3-24.
Hoffman, T.L., et al., "A Biosensor Assay for Studying Ligand-Membrane Receptor Interactions: Binding of Antibodies and HIV-1 Env to Chemokine Receptors," PNAS, 97(21): pp. 11215-11220 (2000).
Gyorvary, E.S., et al., "Self-Assembly and Recrystallization of Bacterial S-Layer Proteins at Silicon Supports Imaged in Real Time by Atomic Force Microscopy," Journal of Microscopy, vol. 212, pp. 300-306 (2003).
Zhang, R., et al., "Tools for GPCR Drug Discovery," Acta Pharmacologica Sinica, 33: pp. 372-384 (2012).
Sleytr, U., et al., "Heterologous Reattachment of Regular Arrays of Glycoproteins on Bacterial Surfaces," Nature, vol. 257, pp. 400-401 (1975).
Sleytr, U., et al., S-Layers Principles and Applications, FEMS Microbiology Rev., pp. 1-42 (2014).

(56) References Cited

OTHER PUBLICATIONS

Pum, D., et al., "Reassembly of S-Layer Proteins," Nanotechnology, pp. 1-15 (2014).
Bleckmann, J., et al., "Surface-Layer Lattices as Patterning Element for Multimeric Extremozymes," Small Journal, pp. 1-8 (2013).
Breitwieser, A., et al., "Magnetic Beads Functionalized with Recombinant S-Layer Protein Exhibit High Human IgG-Binding and Anti-Fouling Properties," Current Topics in Peptide & Protein Research, vol. 17, pp. 45-55 (2016).
Rothbauer, M., et al., "Exploitation of S-Layer Anisotropy: pH-Dependent Nanolayer Orientation for Cellular Micropatterning," Acs NANO, published online (2013).

* cited by examiner

| Name | pI | MW (kDa) | Variation rate(%) | Variation rate(TM %) |
|---|---|---|---|---|
| CCR5 | 9.21 | 40.52 | / | / |
| CCR5$^{QTY}$ | 9.10 | 40.98 | 21.88 | 46.67 |

FIG. 8A

```
1                                                                    60
   MDYQVSSPIYDINYYTSEPCQKINVKQIAARLLPPLYSLVFIFGFVGNMLVILILINCKR
   ||||||||||||||||||||||||||||**|*||**|*||****||||
   MDYQVSSPIYDINYYTSEPCQKINVKQIAARQQPFQYSQTPTYGFTGNMQTTQTQINCKR
61                                                                   120
   LKSMTDIYLLNLAISDLYFLLTVPFWAHYAAAQWDFGNTMCQLLTGLYFIGFFSGIFFII
   ||||||||*|||****||*||**||**|||||||
   LKSMTDIYLQNQAISDQYYQQTTPYWAHYAAAQWDFGNTMCQQQTCQYFTGYYSGTYYTT
121                                                                  180
   LLTIDRYLAVVHAVFALKAPTVTFGVVTSVITWVVAVFASLPGIIFTRSQKEGLHYTCSS
   **|*|||||||||||||||*|*|**||**|**|*|***||||||||||
   QQTTDRYLAVVHAVFALKARTTTYGTTTSTTTWTTATYASQPQTTYTRSQKEGLHYTCSS
181                                                                  240
   HFPYSQYQFWKNFQTLKIVILGLVLPLLVMVICYSGILKTLLRCRNEKKRHRAVRLIFTI
   |||||||||||||||*|*|*|***|*|||**|||||||||**|*
   HPPYSQYQFWKNFQTLKITIQSQVQPQQTMVTCYSGTQKTLLPCRNEKKRHRAVRQTFTT
241                                                                  300
   MIVYFLSWAPYNIVLLLNTFQEFFGLNNCSSSNRLDQAMQVTETLGMTHCCINPIIYAFV
   |**|***||****||||||||||||||*||||**|*||**|
   MTTYYQYWAPYNTTQQLNTFQEFFGLNNCSSSNRLDQAMQVTETQGMTHCCTNPTIYAYV

SEQ ID NO: 2   301                                              360
               GEKFRNYLLVFFQKHIAKRFCKCCSIFQQEAPERASSVYTRSTGEQEISVGL
SEQ ID NO: 3   ||||||||||||||||||||||||||||||||||||||||||||||||||||
               GEKFRNYLLVFFQKHIAKRFCKCCSIFQQEAPERASSVYTRSTGEQEISVGL
```

FIG. 8B

| Name | pI | MW (kDa) | Variation rate(%) | Variation rate(TM %) |
|---|---|---|---|---|
| CXCR4 | 8.46 | 39.75 | / | / |
| CXCR4$^{QTY}$ | 8.40 | 40.21 | 29.26 | 58.11 |

FIG. 8C

```
  1  ════════════════════════════════════════════════⌇⌇⌇⌇⌇⌇⌇⌇⌇⌇⌇⌇  60
     MEGISIYTSDNYTEENGSSDYDSMKEPCFREENANFNKIFLPTIYSIIFLTGIVGNGLVI
     |||||||||||||||||||||||||||||||***||*|||****||**|*|***
     MEGISIYTSDNYTEENGSSDYDSMKEPCFREENANFNKTYQPTTYSTTYQTGTTGQGQTT

61 ══⌇⌇⌇═════════⌇⌇⌇⌇⌇⌇⌇⌇══════════════════════⌇⌇⌇⌇═════════  120
     LVMGYQEKLRSMTDKYRLHLSVADLLFVITLPFWAVDAVANWYFGNFLCKAVHVIYTVNL
     **|||||||*|*|*|||*****|*|*|*|*****|*|*||||||*||**||***
     QTMGYQEKQRSMTDKYRQHQSTADQQYTTTQPYWATDATANWYFGNFQCKATHTTYTTQQ

121 ═⌇⌇⌇⌇═══════════════════════════════⌇⌇⌇⌇⌇⌇⌇══════════════  180
     YSSVLIAFISLDRYLAIVHATNSQRPRKLLAEKVVYVGVWIPALLLTIPDFIFANVSEA
     |||****|**|*|||||||||||||||**||**|*|*|***|*|****||||
     YSSTQTQAYTSQDRYLAIVHATNSQRPRKQQAEKTTYTGTWTPAQQQTTPDYTYANVSEA

181 ═══════⌇⌇⌇⌇⌇⌇⌇════════════════════════════════════════════  240
     DDRYICDRFYPNDLWVVVFQFQHIMVGLILPGIVLLSCYCITISKLSHSKGHQKRKALKT
     |||||||||||||||****|*|*|***|****|||**||||||||||||||||
     DDRYICDRFYPNDLWTTTYQYQHTMTGQTQPGTTTQSCYCTTTSKLSHSKGHQKRKALKT

241 ══⌇⌇⌇⌇⌇⌇⌇⌇══════════════════════════════⌇⌇⌇⌇⌇⌇⌇⌇═══════  300
     TVLILLAFFACWLPYYIGISIDSFILLEIIKQGCEFENTVHKWISITEALAFFHCCLNPI
     |*****|**|**|*|*|||||||||||||||||||*|*|||*|**||**|*
     TTTQTQAYYACWQPYYTGTSTDSFILLEIIKQGCEFENTVHKWTSTTEAQAYYHCCQQPT

301 ══ ·································· 360
     LYAFLGAKFKTSAQHALTSVSRGSSLKILSKGKRGGHSSVSTESESSSFHSS       SEQ ID NO: 4
     *||**|||*|||||*|*|||||*|**|||||||||||||||
     QYAYQGAKYKTSAQHAQTSTSRGSSQKTQSKGKRGGHSSTSTESESSSFHSS       SEQ ID NO: 5
```

FIG. 8D

| Name | pI | MW (kDa) | Variation rate(%) | Variation rate(TM %) |
|---|---|---|---|---|
| CCR10 | 9.85 | 38.42 | / | / |
| CCR10PTY | 9.61 | 39.18 | 19.34 | 47.95 |

FIG. 8E

```
  1 ─────────────────────────────────────────────────────⌒⌒⌒ 60
    MGTEATEQVSWGHYSGDEEDAYSAEPLPELCYKADVQAFSRAFQFSVSLTVAALGLAGNG
    ||||||||||||||||||||||||||||||||||||||||||||||*||*||||
    MGTEATEQVSWGHYSGDEEDAYSAEPLPELCYKADVQAFSRAFQFSVSLTVAAQGQAGNG
 61 ⌒⌒⌒─────────⌒⌒⌒⌒⌒⌒⌒──────────────────────⌒⌒⌒ 120
    LVLATHLAARRAARSPTSAHLLQLALADLLLALTLPFAAAGALQGWSLGSATCPTISGLY
    ***||||*|****||||||||**|||*|***||*|***|||||||||||||*|||
    QTQATHQAAPRAARSPTSAHQQQAQADQQQAQTQPYAAAGALQGWSLGSATCPTTSQQY
121 ⌒⌒⌒⌒⌒⌒⌒⌒──────────────────────────⌒⌒⌒⌒⌒⌒ 180
    SASFHSGFLFLACISADRYVAIAPKLPAGPEPSTPGRAHLVSVIVWLLSLLIALPALLES
    ||*||*****||||||||||||*|||*|||||||||**|***|**|***|*|*|***|
    SASYHAGYQYQACTSADRYVAIARALPAGPRPSTPGRAHQTSTTTWQQSQQQAQPAQQYS
181 ──────────────⌒⌒⌒⌒⌒⌒⌒──────────────────── 240
    QDGQREGQRRCRLIFPEGLTQTVKGASAVAQVALGFALPLGVMVACYALLGRTLLAAPGP
    |||||||||||||||||||||||||*||||*|*|*|*|*|*||*|*|||*||*||||
    QDGQREGQRRCRLIFPEGLTQTVKGASATAQTAQGYAQPQGTMTACYALLGPTLLAARGP
241 ───────⌒⌒⌒⌒⌒⌒⌒⌒⌒⌒⌒⌒⌒⌒⌒⌒──────────────── 300
    ERPRALRVVVALVAAFVVLQLPYSLALLLDTADLLAARERSCPASKRKDVALLVTSGLAL
    ||||**|**|****|*||*|***||||||||||||||||||||||||***||*|*
    ERPPALRTTTAQTAAYTTQXQPYSQAQQQDTADLLAARERSCPASKRKDVAQQTTSKQAQ
301 ⌒⌒⌒⌒⌒─────────────────────────────────────────── 360
    ARCGLNPVLYAFLGLRFPQDLRRLLRGGSCPSGPQPRRGCPRRPRLSSCSAPTETHSLSW
    ||*||**||*||*||||||||||||||||||||||||||||||||||||||||||
    ARCGQNPTQYAYQGLRFPQDLRRLLRSGSCPSGPQPRRGCPRRPLSSCSAPTETHSLSW
361 ······················································ 420
     ── SEQ ID NO: 6
     ── SEQ ID NO: 7
```

FIG. 8F

| Name | pI | MW (kDa) | Variation rate(%) | Variation rate(TM %) |
|------|------|------|------|------|
| CXCR7 | 7.52 | 41.49 | / | / |
| CXCR7mut | 7.50 | 41.96 | 23.20 | 56.38 |

FIG. 8G

```
  1 ────────────────────────────────────⌒⌒⌒⌒⌒⌒⌒⌒ 60
    MGLELFDYSEPGNFSQISWPCNSSHKIVVDTVWCPNMPNKEVLLYTLSFIYIFIFVIGMI
    ||||||||||||||||||||||||*||||||||||*|***|****|*|||***|||*
    MGLELFDYSEPGNFSDISWPCNSSDPCIVVDTVWCPNMPNKSTQQYTQSYTYTYTTGMI
 61 ⌒────────────⌒⌒⌒⌒⌒⌒⌒─────────────────────── 120
    ANSVVVWVNIQAKTTGYDTHCYILNLAIADLWVVLTIPVWVVSLVQHNQWPMGELTCNVT
    |||||||||||||||||||*||*||*||*|||*|||**|**||||||*||||*||*
    ANSVVVWVNIQAKTTGYDTHCYTQNQATADQWTQTPTWTTSLVQHNQWPMGELTCKTT
121 ⌒⌒⌒⌒⌒⌒──────────────────────────────────────── 180
    HLIFSINLFGSIFFLTCMSVDRYLSITYFTNTPSSRKKMVRRVVCILVWLLAFCVSLPDT
    |***|*|**|****|||||||||||||||||||||||**|***|**|*|*|*|||
    HQTYSTNQYGSTYYQTCMSVDRYLSITYFTPTPSSRHPMVRRTTCTQTWQQAYCTSQPDT
181 ───────────────────────⌒⌒⌒⌒⌒⌒⌒⌒───────────────── 240
    YYLKTVTSASNNETYCRSFYPEHSIKEWLIGRELVSVVLGFAVPFSIIAVFYFLLARAIS
    ||*||||||||||||*||||||||||||||*||||*|**|*|||****|*|*|||||
    YYQKTVTSASNNETYCRSFYPEHSIKEWLIGREQTSTTQGYATPYSTTATYYQLARAIS
241 ───────────⌒⌒⌒⌒⌒⌒⌒⌒⌒⌒───────────────────── 300
    ASSDQEKHSSRKIIFSYVVVFLVCWLPYHVAVLLDIFSILHYIPFTCRLEHALFTALHVT
    |||||||||||||||***|*****|||||||*|*|*|||||||||||||||*|*|*
    ASSDQEKHSSRKTTISYTTTYQTDWQPYHTATQLSIPSILHYIPFTCRLEHALFIAQHTT
301 ⌒⌒⌒⌒⌒⌒─────────────────────────────────────── 360
    QCLSLVHCCVNPVLYSFINRNYRRYLMKAFIFKYSAHTGLTKLIDASRVSETEYSALEQS
    ||*||*|*||**||**||||||||||||||*|*|||*|||||||||||||||||||*
    QDSQTHCCTNPTQSYTNRNYPYELMKAFIEKYSAKTSLFKLIDASRVSETEYSALEQS
361 ······················································ 420
     ── SEQ ID NO: 8
     ── SEQ ID NO: 9
```

FIG. 8H

SEQUENCE LISTING

<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ser Gly Gly Gly Ser Gly Gly Gly Ala Ser Ser Gly Gly Gly Ala Gly
1               5                   10                  15

Gly Gly Ala Ser
            20

<210> SEQ ID NO 2
<211> LENGTH: 352
<212> TYPE: PRT
<213> ORGANISM: Homo sapiens

<400> SEQUENCE: 2

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

-continued

```
Leu Pro Pro Leu Tyr Ser Leu Val Phe Ile Phe Gly Phe Val Gly Asn
             35                  40                  45

Met Leu Val Ile Leu Ile Leu Ile Asn Cys Lys Arg Leu Lys Ser Met
 50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Gln Trp Asp Phe
                 85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 3
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Gln
                20                  25                  30

Gln Pro Pro Gln Tyr Ser Gln Thr Phe Thr Tyr Gly Phe Thr Gly Asn
```

```
                35                  40                  45
Met Gln Thr Thr Gln Thr Gln Ile Asn Cys Lys Arg Leu Lys Ser Met
 50                  55                  60

Thr Asp Ile Tyr Leu Gln Asn Gln Ala Ile Ser Asp Gln Tyr Tyr Gln
 65                  70                  75                  80

Gln Thr Thr Pro Tyr Trp Ala His Tyr Ala Ala Gln Trp Asp Phe
                 85                  90                  95

Gly Asn Thr Met Cys Gln Gln Thr Gly Gln Tyr Phe Thr Gly Tyr
                100                 105                 110

Tyr Ser Gly Thr Tyr Tyr Thr Thr Gln Gln Thr Asp Arg Tyr Leu
                115                 120                 125

Ala Val Val His Ala Val Phe Ala Leu Lys Ala Arg Thr Thr Tyr
                130                 135                 140

Gly Thr Thr Thr Ser Thr Thr Thr Trp Thr Thr Ala Thr Tyr Ala Ser
145                 150                 155                 160

Gln Pro Gly Thr Thr Tyr Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Thr Ile Gln Gly Gln Val Gln Pro Gln Gln
                195                 200                 205

Thr Met Val Thr Cys Tyr Ser Gly Thr Gln Lys Thr Leu Leu Arg Cys
210                 215                 220

Arg Asn Glu Lys Lys Arg His Arg Ala Val Arg Gln Thr Phe Thr Thr
225                 230                 235                 240

Met Thr Thr Tyr Tyr Gln Tyr Trp Ala Pro Tyr Asn Thr Thr Gln Gln
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Gln Gly Met Thr
                275                 280                 285

His Cys Cys Thr Asn Pro Thr Ile Tyr Ala Tyr Val Gly Glu Lys Phe
                290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350

<210> SEQ ID NO 4
<211> LENGTH: 352
<212> TYPE: PRT
<213> ORGANISM: Homo sapiens

<400> SEQUENCE: 4

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
                35                  40                  45

Phe Leu Thr Gly Ile Val Gly Asn Gly Leu Val Ile Leu Val Met Gly
                50                  55                  60
```

-continued

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 5
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Thr Tyr Gln Pro Thr Thr Tyr Ser Thr Thr
        35                  40                  45

Tyr Gln Thr Gly Thr Thr Gly Gln Gly Thr Gln Thr Met Gly
    50                  55                  60

Tyr Gln Lys Lys Gln Arg Ser Met Thr Asp Lys Tyr Arg Gln His Gln
65                  70                  75                  80

Ser Thr Ala Asp Gln Gln Tyr Thr Thr Thr Gln Pro Tyr Trp Ala Thr
                 85                  90                  95

Asp Ala Thr Ala Asn Trp Tyr Phe Gly Asn Phe Gln Cys Lys Ala Thr
            100                 105                 110

His Thr Thr Tyr Thr Thr Gln Gln Tyr Ser Ser Thr Gln Thr Gln Ala
        115                 120                 125

Tyr Thr Ser Gln Asp Arg Tyr Leu Ala Ile Val His Ala Thr Asn Ser
    130                 135                 140

Gln Arg Pro Arg Lys Gln Gln Ala Glu Lys Thr Thr Tyr Thr Gly Thr
145                 150                 155                 160

Trp Thr Pro Ala Gln Gln Thr Thr Pro Asp Tyr Thr Tyr Ala Asn
                165                 170                 175

Val Ser Glu Ala Asp Asp Arg Tyr Ile Cys Asp Arg Phe Tyr Pro Asn
            180                 185                 190

Asp Leu Trp Thr Thr Thr Tyr Gln Tyr Gln His Thr Met Thr Gly Gln
        195                 200                 205

Thr Gln Pro Gly Thr Thr Thr Gln Ser Cys Tyr Cys Thr Thr Thr Ser
    210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Thr Ser Thr Thr Glu
        275                 280                 285

Ala Gln Ala Tyr Tyr His Cys Cys Gln Gln Pro Thr Gln Tyr Ala Tyr
    290                 295                 300

Gln Gly Ala Lys Tyr Lys Thr Ser Ala Gln His Ala Gln Thr Ser Thr
305                 310                 315                 320

Ser Arg Gly Ser Ser Gln Lys Thr Gln Ser Lys Gly Lys Arg Gly Gly
                325                 330                 335

His Ser Ser Thr Ser Thr Glu Ser Glu Ser Ser Ser Phe His Ser Ser
            340                 345                 350

<210> SEQ ID NO 6
<211> LENGTH: 362
<212> TYPE: PRT
<213> ORGANISM: Homo sapiens

<400> SEQUENCE: 6

Met Gly Thr Glu Ala Thr Glu Gln Val Ser Trp Gly His Tyr Ser Gly
1               5                   10                  15

Asp Glu Glu Asp Ala Tyr Ser Ala Glu Pro Leu Pro Glu Leu Cys Tyr
                20                  25                  30

Lys Ala Asp Val Gln Ala Phe Ser Arg Ala Phe Gln Pro Ser Val Ser
            35                  40                  45

Leu Thr Val Ala Ala Leu Gly Leu Ala Gly Asn Gly Leu Val Leu Ala
        50                  55                  60

Thr His Leu Ala Ala Arg Arg Ala Arg Ser Pro Thr Ser Ala His
65                  70                  75                  80

Leu Leu Gln Leu Ala Leu Asp Leu Leu Ala Leu Thr Leu Pro
                85                  90                  95

Phe Ala Ala Ala Gly Ala Leu Gln Gly Trp Ser Leu Gly Ser Ala Thr

```
            100                 105                 110
Cys Arg Thr Ile Ser Gly Leu Tyr Ser Ala Ser Phe His Ala Gly Phe
            115                 120                 125

Leu Phe Leu Ala Cys Ile Ser Ala Asp Arg Tyr Val Ala Ile Ala Arg
    130                 135                 140

Ala Leu Pro Ala Gly Pro Arg Pro Ser Thr Pro Gly Arg Ala His Leu
145                 150                 155                 160

Val Ser Val Ile Val Trp Leu Ser Leu Leu Ala Leu Pro Ala
                165                 170                 175

Leu Leu Phe Ser Gln Asp Gly Gln Arg Glu Gly Gln Arg Arg Cys Arg
            180                 185                 190

Leu Ile Phe Pro Glu Gly Leu Thr Gln Thr Val Lys Gly Ala Ser Ala
            195                 200                 205

Val Ala Gln Val Ala Leu Gly Phe Ala Leu Pro Leu Gly Val Met Val
            210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Val Ala Leu Val Ala Ala Phe
                245                 250                 255

Val Val Leu Gln Leu Pro Tyr Ser Leu Ala Leu Leu Asp Thr Ala
            260                 265                 270

Asp Leu Leu Ala Ala Arg Glu Arg Ser Cys Pro Ala Ser Lys Arg Lys
            275                 280                 285

Asp Val Ala Leu Leu Val Thr Ser Gly Leu Ala Leu Ala Arg Cys Gly
            290                 295                 300

Leu Asn Pro Val Leu Tyr Ala Phe Leu Gly Leu Arg Phe Arg Gln Asp
305                 310                 315                 320

Leu Arg Arg Leu Leu Arg Gly Gly Ser Cys Pro Ser Gly Pro Gln Pro
                325                 330                 335

Arg Arg Gly Cys Pro Arg Arg Pro Arg Leu Ser Ser Cys Ser Ala Pro
                340                 345                 350

Thr Glu Thr His Ser Leu Ser Trp Asp Asn
            355                 360

<210> SEQ ID NO 7
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Thr Glu Ala Thr Glu Gln Val Ser Trp Gly His Tyr Ser Gly
1               5                   10                  15

Asp Glu Glu Asp Ala Tyr Ser Ala Glu Pro Leu Pro Glu Leu Cys Tyr
            20                  25                  30

Lys Ala Asp Val Gln Ala Phe Ser Arg Ala Phe Gln Pro Ser Val Ser
        35                  40                  45

Leu Thr Val Ala Ala Gln Gly Gln Ala Gly Asn Gly Gln Thr Gln Ala
    50                  55                  60

Thr His Gln Ala Ala Arg Arg Ala Ala Arg Ser Pro Thr Ser Ala His
65                  70                  75                  80

Gln Gln Gln Gln Ala Gly Ala Asp Gln Gln Ala Gln Thr Gln Pro
            85                  90                  95
```

-continued

```
Tyr Ala Ala Ala Gly Ala Leu Gln Gly Trp Ser Leu Gly Ser Ala Thr
                100                 105                 110

Cys Arg Thr Thr Ser Gly Gln Tyr Ser Ala Ser Tyr His Ala Gly Tyr
            115                 120                 125

Gln Tyr Gln Ala Cys Thr Ser Ala Asp Arg Tyr Val Ala Ile Ala Arg
        130                 135                 140

Ala Leu Pro Ala Gly Pro Arg Pro Ser Thr Pro Gly Arg Ala His Gln
145                 150                 155                 160

Thr Ser Thr Thr Thr Trp Gln Gln Ser Gln Gln Ala Gln Pro Ala
                165                 170                 175

Gln Gln Tyr Ser Gln Asp Gly Gln Arg Glu Gly Gln Arg Cys Arg
            180                 185                 190

Leu Ile Phe Pro Glu Gly Leu Thr Gln Thr Val Lys Gly Ala Ser Ala
            195                 200                 205

Thr Ala Gln Thr Ala Gln Gly Tyr Ala Gln Pro Gln Gly Thr Met Thr
        210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Thr Thr Thr Ala Gln Thr Ala Ala Tyr
                245                 250                 255

Thr Thr Gln Gln Gln Pro Tyr Ser Gln Ala Gln Gln Gln Asp Thr Ala
            260                 265                 270

Asp Leu Leu Ala Ala Arg Glu Arg Ser Cys Pro Ala Ser Lys Arg Lys
        275                 280                 285

Asp Val Ala Gln Gln Thr Thr Ser Gly Gln Ala Gln Ala Arg Cys Gly
290                 295                 300

Gln Asn Pro Thr Gln Tyr Ala Tyr Gln Gly Leu Arg Phe Arg Gln Asp
305                 310                 315                 320

Leu Arg Arg Leu Leu Arg Gly Gly Ser Cys Pro Ser Gly Pro Gln Pro
                325                 330                 335

Arg Arg Gly Cys Pro Arg Arg Pro Arg Leu Ser Ser Cys Ser Ala Pro
            340                 345                 350

Thr Glu Thr His Ser Leu Ser Trp Asp Asn
            355                 360

<210> SEQ ID NO 8
<211> LENGTH: 362
<212> TYPE: PRT
<213> ORGANISM: Homo sapiens

<400> SEQUENCE: 8

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
                20                  25                  30

Met Cys Pro Asn Met Pro Asn Lys Ser Val Leu Leu Tyr Thr Leu Ser
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
                100                 105                 110
```

Gly Glu Leu Thr Cys Lys Val Thr His Leu Ile Phe Ser Ile Asn Leu
            115                 120                 125

Phe Gly Ser Ile Phe Phe Leu Thr Cys Met Ser Val Asp Arg Tyr Leu
        130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 9
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Thr Gln Gln Tyr Thr Gln Ser
        35                  40                  45

Tyr Thr Tyr Thr Tyr Thr Tyr Thr Thr Gly Met Thr Ala Asn Ser Val
    50                  55                  60

Val Val Trp Val Asn Ile Gln Ala Lys Thr Thr Gly Tyr Asp Thr His
65                  70                  75                  80

Cys Tyr Thr Gln Asn Gln Ala Thr Ala Asp Gln Trp Thr Thr Gln Thr
                85                  90                  95

Thr Pro Thr Trp Thr Thr Ser Leu Val Gln His Asn Gln Trp Pro Met

```
            100                 105                 110
Gly Glu Leu Thr Cys Lys Thr Thr His Gln Thr Tyr Ser Thr Asn Gln
        115                 120                 125

Tyr Gly Ser Thr Tyr Tyr Gln Thr Cys Met Ser Val Asp Arg Tyr Leu
        130                 135             140

Ser Ile Thr Tyr Phe Thr Asn Thr Pro Ser Ser Arg Lys Lys Met Val
145                 150                 155                 160

Arg Arg Thr Thr Cys Thr Gln Thr Trp Gln Gln Ala Tyr Cys Thr Ser
                165                 170                 175

Gln Pro Asp Thr Tyr Gln Lys Thr Val Thr Ser Ala Ser Asn Asn
            180                 185                 190

Glu Thr Tyr Cys Arg Ser Phe Tyr Pro Glu His Ser Ile Lys Glu Trp
            195                 200                 205

Leu Ile Gly Met Glu Gln Thr Ser Thr Thr Gln Gly Tyr Ala Thr Pro
        210                 215                 220

Tyr Ser Thr Thr Ala Thr Tyr Tyr Gln Leu Ala Arg Ala Ile Ser
225                 230                 235                 240

Ala Ser Ser Asp Gln Glu Lys His Ser Ser Arg Lys Thr Thr Tyr Ser
                245                 250                 255

Tyr Thr Thr Thr Tyr Gln Thr Cys Trp Gln Pro Tyr His Thr Ala Thr
                260                 265                 270

Gln Leu Asp Ile Phe Ser Ile Leu His Tyr Ile Pro Phe Thr Cys Arg
            275                 280                 285

Leu Glu His Ala Leu Phe Thr Ala Gln His Thr Thr Gln Cys Gln Ser
        290                 295                 300

Gln Thr His Cys Cys Thr Asn Pro Thr Gln Tyr Ser Tyr Thr Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
                340                 345                 350

Glu Tyr Ser Ala Leu Glu Gln Ser Thr Lys
            355                 360

<210> SEQ ID NO 10
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Tyr Asn Lys Thr Phe Leu Pro Thr Ile Tyr Ser Ile Ile
        35                  40                  45

Tyr Gln Thr Gly Thr Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Thr Ala Asp Leu Gln Phe Val Thr Thr Leu Pro Tyr Trp Ala Thr
                85                  90                  95
```

-continued

```
Asp Ala Thr Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
            130                 135                 140

Gln Arg Pro Arg Lys Leu Leu Ala Glu Lys Val Val Tyr Val Gly Val
145                 150                 155                 160

Trp Thr Pro Ala Gln Leu Leu Thr Thr Pro Asp Tyr Thr Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Thr Thr Leu Ile Gln Ala Phe Phe Ala Cys Trp Gln Pro Tyr Tyr
                245                 250                 255

Thr Gly Ile Ser Ile Asp Ser Tyr Ile Leu Leu Glu Ile Ile Lys Gln
                260                 265                 270

Gly Cys Glu Phe Glu Asn Thr Val His Lys Trp Ile Ser Thr Thr Glu
                275                 280                 285

Ala Gln Ala Phe Tyr His Cys Cys Gln Asn Pro Thr Gln Tyr Ala Tyr
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350
```

S-LAYER PROTEIN 2D LATTICE COUPLED DETERGENT-FREE GPCR BIOELECTRONIC INTERFACES, DEVICES, AND METHODS FOR THE USE THEREOF

RELATED APPLICATIONS

This application claims the benefit of U.S. Provisional Application No. 62/553,266 filed Sep. 1, 2017 and U.S. Provisional Application No. 62/570,174 filed Oct. 10, 2017. The entire teachings of each of the above-referenced applications are incorporated herein by reference.

BACKGROUND OF THE INVENTION

The G-protein-coupled receptor (GPCR) family is a superfamily of signaling proteins that play a role in numerous processes including energy conversion, cell signaling, cell-cell interactions, cell adhesion, cell migration, protein trafficking, viral fusion, neural synaptic activities, and ion and metabolite transport. GPCRs are seven transmembrane proteins that consist of a single polypeptide folded into a globular shape and which are embedded in plasma membranes. Humans have nearly 1000 different GPCRs, each highly specific to a particular signal. Because they play a role in such a range of vital processes, these receptors are a major focus of drug discovery efforts for a diverse set of diseases. It is estimated that one-third to one-half of all marketed drugs act by binding to a GPCR. Indeed, recent studies have shown that GPCRs play a critical role in tumor initiation, progression, invasion and metastasis. Despite their importance, there remains a large proportion of GPCRs for which ligands have not yet been identified. In addition, a further understanding of the structure and function of GPCRs is needed.

There are several factors that impede the study of GPCRs and the development of ligand-binding assays. For example, these transmembrane proteins are difficult to solubilize, extract, and purify. Native GPCRs are insoluble in water without detergents. However, when GPCRs are isolated in detergents, the detergents can have negative effects on the stability and function of the transmembrane proteins. It would therefore be advantageous to develop cell-free and detergent-free devices and methods to detect and measure ligand binding of GPCRs.

SUMMARY OF THE INVENTION

The present invention is based on the discovery that the two-dimensional (2D) crystalline lattice formed by self-assembling S-layer proteins on a surface can be used as a carrier for water-soluble variant GPCRs. For example, as shown in the Examples, CXCR4-QTY-Fc bound to rSbpA$_{31-1068}$ZZ-coated hydrophobic silicon wafers.

In certain aspects, the invention is directed to a self-assembling unit comprising a variant GPCR fusion protein bound to an S-layer fusion protein wherein:
  i. the S-layer fusion protein comprises an S-layer protein and a fusion domain, wherein the fusion domain is fused to the C-terminus of the S-layer protein, and wherein a plurality of S-layer fusion proteins are capable of self-assembly into a two-dimensional crystal lattice on a surface; and
  ii. the variant GPCR fusion protein comprises a variant GPCR and a binding moiety;
    wherein the variant GPCR is a water-soluble variant of a native GPCR wherein a plurality of amino acid residues Leucine (L), isoleucine (I), valine (V), and phenylalanine (F) within the seven-transmembrane α-helical domain of the native GPCR are replaced with glutamine (Q), threonine (T), threonine (T), and tyrosine (Y), respectively; and
    wherein the binding moiety is fused to the C-terminus of the variant GPCR, has binding affinity for the fusion domain of the S-layer fusion protein, and further wherein the binding moiety is bound to the fusion domain.

In some embodiments, the present invention is directed to a bioelectronic interface, or a surface-modified substrate, comprising:
  a) a solid substrate; and
  b) a plurality of self-assembling units wherein:
    i. each self-assembling unit comprises a variant GPCR fusion protein bound to an S-layer fusion protein;
    ii. the S-layer fusion protein comprises an S-layer protein and a fusion domain,
      wherein the N-terminus of the S-layer fusion protein is bound to the surface of the solid substrate,
      wherein the fusion domain is fused to the C-terminus of the S-layer protein, and
      wherein a plurality of S-layer fusion proteins form a two-dimensional crystalline lattice on the surface of the solid substrate;
    iii. the variant GPCR fusion protein comprises a variant GPCR and a binding moiety;
      wherein the variant GPCR is a water-soluble variant of a native GPCR wherein a plurality of amino acid residues Leucine (L), isoleucine (I), valine (V), and phenylalanine (F) within the seven-transmembrane α-helical domain of the native GPCR are replaced with glutamine (Q), threonine (T), threonine (T), and tyrosine (Y), respectively, and
      wherein the binding moiety is fused to the C-terminus of the variant GPCR, has binding affinity for the fusion domain of the S-layer fusion protein, and further wherein the binding moiety is bound to the fusion domain of the S-layer fusion protein.

In additional aspects, the invention encompasses a biosensor or device comprising the bioelectronic interface or surface-modified substrate. In yet additional aspects, the invention includes a method for screening for a ligand of a GPCR comprising the steps of contacting a potential ligand with the bioelectronic interface or surface-modified substrate and measuring the binding of the potential ligand to the bioelectronic interface or surface modified substrate. In further embodiments, the invention is directed to a method of determining the presence of a GPCR ligand in a sample comprising the steps of contacting the sample with the bioelectronic interface or surface-modified substrate and measuring the binding of the ligand to the bioelectronic interface or surface modified substrate.

In further embodiments, the invention encompasses a method for screening a potential ligand for binding to a G-protein coupled receptor (GPCR) comprising the steps of:
  a) contacting a potential ligand with a variant GPCR immobilized on a solid substrate,
    wherein the variant GPCRs is part of a self-assembling unit that comprises a variant GPCR fusion protein bound to an S-layer fusion protein; wherein:
      i. the S-layer fusion protein comprises an S-layer protein and a fusion domain, wherein the fusion domain is fused to the C-terminus of the S-layer protein, and wherein a plurality of S-layer fusion proteins self-assembles into a two-dimensional crystal lattice on the surface; and ii. the variant GPCR fusion protein comprises the variant GPCR and a binding moiety;

wherein the variant GPCR is a water-soluble variant of a native GPCR wherein a plurality of amino acid residues Leucine (L), isoleucine (I), valine (V), and phenylalanine (F) within the seven-transmembrane α-helical domain of the native GPCR are replaced with glutamine (Q), threonine (T), threonine (T), and tyrosine (Y), respectively; and wherein the binding moiety is fused to the C-terminus of the variant GPCR, has binding affinity for the fusion domain of the S-layer fusion protein, and further wherein the binding moiety is bound to the fusion domain;

and b) measuring the binding of the potential ligand to the variant GPCR, wherein the binding of the potential ligand to the variant GPCR is indicative of binding to the native GPCR.

In yet further embodiments, the invention encompasses a method for detecting a G-protein coupled receptor (GPCR) ligand in a sample comprising the steps of:

a) contacting the sample with a variant GPCR immobilized on a solid substrate, wherein the variant GPCRs is part of a self-assembling unit that comprises a variant GPCR fusion protein bound to an S-layer fusion protein; wherein:

i. the S-layer fusion protein comprises an S-layer protein and a fusion domain, wherein the fusion domain is fused to the C-terminus of the S-layer protein, and wherein a plurality of S-layer fusion proteins self-assembles into a two-dimensional crystal lattice on the surface; and ii. the variant GPCR fusion protein comprises the variant GPCR and a binding moiety;

wherein the variant GPCR is a water-soluble variant of a native GPCR wherein a plurality of amino acid residues Leucine (L), isoleucine (I), valine (V), and phenylalanine (F) within the seven-transmembrane α-helical domain of the native GPCR are replaced with glutamine (Q), threonine (T), threonine (T), and tyrosine (Y), respectively; and wherein the binding moiety is fused to the C-terminus of the variant GPCR, has binding affinity for the fusion domain of the S-layer fusion protein, and further wherein the binding moiety is bound to the fusion domain;

and b) measuring the binding of the ligand to the variant GPCR, wherein the binding of the potential ligand to the variant GPCR is indicative of binding to the native GPCR.

The invention also encompasses a GPCR variant fusion protein comprising a variant GPCR as described herein fused to an Fc region; for example, a human IgG Fc region such as a human IgG1 Fc region.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

(FIG. 7A) Crystallographic electronic density maps of the following amino acids: Leucine (L), Asparagine (N), Glutamine (Q), Isoleucine (I), Valine (V), Threonine (T), Phenylalanine (F) and Tyrosine (Y). The density maps of L, N and Q are very similar. Likewise, the density maps of I, V and T are similar, and the density maps of F and Y are similar. The CA, CB, CG, CD, CE and CZ denote the alpha, beta, gamma, delta, epsilon and zeta positions of carbon; OG1, OD1, OE1 and OH1 denote the gamma, delta, epsilon and eta positions of oxygen; ND2 and NE2 denote the delta and epsilon positions of nitrogen. The side chains of L, V, I, and F cannot form any hydrogen bonds with water, thus rendering them water-insoluble. On the other hand, N and Q can form 4 hydrogen bonds with 4 water molecules, 2 on OD1 and OE1 as hydrogen donors and 2 on DN2 and NE2 as hydrogen acceptors. Likewise, 3 water molecules can form hydrogen bonds with the —OH (2 H-donors and 1 H-acceptor) on OG1 of Thr (T) and the OH1 of Tyr (Y). Both L and Q have high tendencies to form α-helices, but N frequently occurs at turns. Thus Q was used to replace L, but not N. I, V and T are all beta-branched amino acids. Their density maps are very similar indicating similar shapes. (FIG. 7B) Helical wheels before and after applying the QTY Code to transmembrane helical segment 1 (TM1) of CCR5. Before applying QTY code, there were 14 hydrophobic residues (green color); after applying the QTY Code, only 3 hydrophobic residues remained. Amino acids that interact with water molecules are light blue in color. The QTY code conversions render the helical segment water-soluble. (FIG. 7C) Schematic depiction of a water-insoluble α-helix (green) rendered water-soluble (light blue). (FIG. 7D) Schematic depiction of a GPCR (green color) embedded in lipid membrane bilayer (left panel). After applying the QTY Code, the same GPCR is water-soluble (light blue color) and is surrounded by water molecules.

FIGS. 8A to 8H show alignments of the native CCR5, CXCR4, CCR10 and CXCR7 with detergent-free $CCR5^{QTY}$, $CXCR4^{QTY}$, $CCR10^{QTY}$ and $CXCR7^{QTY}$. (FIG. 8A) Characteristics of natural CCR5 and $CCR5^{QTY}$ with pI, molecular weight, total variation rate (21.88%) and membrane variation rate (46.67%). (FIG. 8B) The alignment of CCR5 and $CCR5^{QTY}$ with the α-helical segments (blue) shown above the protein sequences. (FIG. 8C) Characteristics of natural CXCR4 and $CXCR4^{QTY}$ with pI, molecular weight, total variation rate (29.26%) and membrane variation rate (58.11%). (FIG. 8D) The alignment of CXCR4 and $CXCR4^{QTY}$ with the α-helical segments (blue) shown above the protein sequences. Since the internal regions ICL1, ICL2, ICL3 and the C-terminus do not interact with the ligand SDF1α, additional residues in these regions were modified according to the QTY Code to further increase the water-solubility of $CXCR4^{QTY}$. (FIG. 8E) Characteristics of natural CCR10 and $CCR10^{QTY}$ with pI, molecular weight, total variation rate (19.34%) and membrane variation rate (47.95%). (FIG. 8F) The alignment of CCR10 and $CCR10^{QTY}$ with α-helical segments (blue) shown above the protein sequences. (FIG. 8G) Characteristics of natural CXCR7 and $CXCR7^{QTY}$ with pI, molecular weight, total variation rate (23.20%) and membrane variation rate (56.38%). (FIG. 8H) The alignment of CXCR7 and $CXCR7^{QTY}$ with α-helical segments (blue) shown above the protein sequences. In (FIG. 8B), (FIG. 8D), (FIG. 8F), and (FIG. 8H), the red and yellow lines denote the external and internal segments of the protein, respectively. The symbols | and * indicate the similar and different amino acids, respectively.

FIGS. 9A to 9E show Microscale thermophoresis (MST) ligand binding measurements. The receptors were labeled with a fluorescent dye since both receptors and ligands contain tryptophan. All ligands were serially diluted in either buffer or 50% human serum. Human insulin was used as a negative control since the chemokine receptors should not bind to human insulin. The Microscale Thermophoresis data are normalized to 0=unbound and 1=bound. The bars represent the standard deviation of 3 independent experiments with duplicate measurements for each experiment (a total of 6 measurements for each sample). (FIG. 9A) $CCR5^{QTY}$ with $CCL5_{26-91}$ (also called Rantes). In buffer $K_D$=33.9±4.8, and in 50% human serum $K_D$=45.9±7.9. (FIG. 9B) $CXCR4^{QTY}$ with $CXCL12_{24-88}$ (also called SDF1a). In buffer $K_D$=11.2±3.4, and in 50% human serum $K_D$=44.7±8.9, (FIG. 9C) $CCR10^{QTY}$ with CCL27 and CCL28. In buffer $K_D$=3.1±1.2 for CCL27 and $K_D$=9.3±1.8 for CCL28. In 50% human serum $K_C$=5.6±1.1 for CCL27 and $K_D$=21±4 for CCL28. (FIG. 9D) $CXCR7^{QTY}$ with CXCL11 and $CXCL12_{24-88}$. In buffer $K_D$=16±3 for CXCL11 and $K_D$=2.2±0.7 for CXCL12. In 50% human serum $K_D$=28±11 for CXCL11 and $K_D$=6.6±1.7 for CXCL12. (FIG. 9E) $CCR5^{QTY}$, $CXCR4^{QTY}$ and $CXCR7^{QTY}$ binding to HIV-1 coat protein gp41-120. $CCR5^{QTY}$ has $K_D$=3.1±0.7 nM in buffer, and $K_D$=4.3±1.5 in 50% human serum. $CXCR4^{QTY}$ has $K_D$=117±26 in buffer and $K_D$=185±25 nM in 50% human serum. $CXCR7^{QTY}$ has $K_D$=1.2±0.4 nM in buffer and $K_D$=7±1.5 nM in 50% human serum (Please see Table 1). These QTY variants do not bind human insulin, thus suggesting binding specificity.

FIGS. 10A to 10D: Thermostability of the chemokine receptors $CCR5^{QTY}$, $CXCR4^{QTY}$, $CCR10^{QTY}$ and $CXCR7^{QTY}$ measured using NanoDSF. In order to obtain Tm curves (green lines), the QTY engineered receptors were heated gradually to slowly denature them. In the controls (red lines), the proteins were heated to 90° C. for 15 minutes before taking any measurements. These experimental results show that (FIG. 10A) $CCR5^{QTY}$ has a Tm at 52.7° C., that (FIG. 10B) $CXCR4^{QTY}$ exhibits 2 transition temperatures: $Tm_1$ at 46.8° C. and $Tm_2$ at ~63.5° C., that (FIG. 10C) $CCR10^{QTY}$ has a Tm at 54.8° C., and that (FIG. 10D) $CXCR7^{QTY}$ has a Tm at 52.3° C. These results suggest the designed variants $CCR5^{QTY}$, $CXCR4^{QTY}$, $CCR10^{QTY}$ and $CXCR7^{QTY}$ are relatively thermally stable. Since there are few hydrophobic residues inside the proteins, the receptor structures may fold and remain stable via extensive hydrogen bonds within the protein and water molecule bridges. This situation is similar to the molecular structures of various collagens that have extensive water molecule bridges stabilizing their structures.

FIG. 11 shows computer simulations of $CCR5^{QTY}$ and $CXCR4^{QTY}$ superimposed with the crystal structures of CCR5 and CXCR4; and simulations of $CCR10^{QTY}$, $CXCR7^{QTY}$. Computer simulations of $CCR5^{QTY}$ and $CXCR4^{QTY}$ were carried out in an explicit water environment. The X-ray crystal structures of natural CCR5 (4MBS) and CXCR4 (3ODU) were obtained from the Protein Data Bank (PDB). The protein structures were determined with a rubredoxin (CCR5) or T4 lysozyme (CXCR4) insert in the $3r^d$ internal loop. The simulated $CCR5^{QTY}$ and $CXCR4^{QTY}$ do not have such rubredoxin or lysozyme inserts. For clarity, comparisons with $CCR5^{QTY}$ and $CXCR4^{QTY}$ have these inserts removed. After 1 μ second of simulation in an explicit water environment, $CCR5^{QTY}$ (teal color) was superimposed with its natural counterpart CCR5 (magenta color) and is shown with two different side views in (a) and (b) and in a top view in (c). Likewise, $CXCR4^{QTY}$ (blue color) was superimposed with its natural counterpart CXCR4 (green color). Two side views are shown in (d) and (e) and a top view is shown in (f). Currently there is no crystal structure available for CCR10. Thus, the simulated $CCR10^{QTY}$ is shown alone in two different side views (g, h) and a top view (1). Likewise, currently no crystal structure is available for CXCR7. Thus, the simulated $CXCR7^{QTY}$ is shown alone in two different side views (j, k) and a top view (l).

FIG. 12 shows internal hydrogen bonds in the simulated $CCR5^{QTY}$, $CXCR4^{QTY}$, $CCR10^{QTY}$ and $CXCR7^{QTY}$ variants. Numerous internal hydrogen bonds are formed in the QTY variants. These include three kinds of intra-helical or inter-helical hydrogen bonds: 1) bonds between side chains, 2) bonds between side chains and the backbone, and 3) bonds between networks of side-chains, side-chains, and the backbone. Notation: 's' denotes a side chain bond and 'b' denotes a backbone bond. Thus, Q121s-T152s-T148b denotes that the side chain of Q at location 121 forms a hydrogen bond with the side chain of T at location 152, which forms a hydrogen bond with the backbone of T at position 148. For example, i) in CCR5$^{QTY}$: (a) Q121s-T152s-T148b, (b) Q252s-Q256s-T199s-T195b, (c) Y118s-E283s-R247s, (d) T143b-T147s,b-T150s,b,-T154s, here, 4 consecutive T formed hydrogen bonds on their side chains in addition to the intra-helical hydrogen bonds, likely further stabilizing the structure, (e) Q33s-Q277s, (f) Q68s-D125s-R140s, (g) Y79s-Y108s; ii) In CXCR4$^{QTY}$: (h) Q260s-S260s-Y256b, (1) T215b-Q216s-Q246s, (j) Y249s-Q253, (k) Q167s-H203b, (1) T169s-Q165b, (m) T204s-Q208s, (n) Q78s-Q69s-Q69b, (o) T112s-Q108b, (p) Q290s-T287b; iii) in CCR10$^{QTY}$: (q) D35s-R192s-D289s, (r) Y14s-Q172-Q214/Q172-S106b, (s) Q63s-Q82s, (t) Q167s-T163s-H159b, (u) Q54s-Q305s-Y256b-Q252s-Q81s-T308s, (v) H66s-Q63s-Q82/Q63s-N306b, (w) Q259s-Q298s, (x) Y263 s-Q211s-S207b, (y) D270s-Q292s; iv) in CXCR7$^{QTY}$: (aa) Y257s-Q86s-S131s, (ab) Y124s-Y268s, (ac) Y315s-N69s-H80s, (ad) Y232s-T259s, (ae) T260s-H307s, (af) Q273-S15s, (ag) Q234s-R237s, (ah) Q314s-S256s, (ai) Q297s-A271b, (aj) T310-T306b, T313s-C309b. Numerous additional internal hydrogen bonds may stabilize the structures of the QTY variants, as suggested by their Tm. Without introducing the QTY mutations, these hydrogen bonds would not have been able to form: L, V, I and F do not have —OH and H$_2$N—CH—C═O side that these helical segments have become water-soluble. Comparison of (a) CCR5 and (b) CCR5$^{QTY}$, and comparison of (c) CXCR4 and (d) CXCR4$^{QTY}$ shows that the QTY variants are more water-soluble. Since currently there are no crystal or NMR structures available for CCR10 or CXCR7, only (e) CCR10$^{QTY}$ and (f) CXCR7$^{QTY}$ are shown.

(FIG. 25A) FM image of rSbpA31-1068 ZZ recrystallized on silicon wafer. A recombinant S-layer protein produced in *E. coli* inclusion body was purified and allow it to self-assemble on to 2D surface. A cluster (look like mini waffle) of S-layer proteins on the surface is shown. Each individual spot is a tetramer of S-layer proteins. The crystalline S-layer showing square (p4) lattice symmetry is clearly visible. After the assembly of the lattice and after linking GPCR-Fc, the whole complex can be inter- and intra-molecularly cross-linked. Using a proper support cross-linking can also involve binding sites between the lattice and the support. The cross-linking also enables very stable S-layers, which are very important for long-term shelf-life and drying process. Scale-bar 100 nm. (FIG. 25B) S-layer protein 2D crystal lattice arrays in high resolution. Each tetramer unit cell is about 13 nM$^2$. Thus each 1.3 cm$^2$ (about a fingernail size) contains ~10$^{12}$ S-layer tetramers.

DETAILED DESCRIPTION OF THE INVENTION

A description of preferred embodiments of the invention follows.

The words "a" or "an" are meant to encompass one or more, unless otherwise specified.

A "polypeptide" is a polymer of amino acid residues joined by peptide bonds. The term "polypeptide" includes proteins.

The invention encompasses bioelectronic interfaces, surface-modified substrates, bioelectronic devices including biosensors, and methods comprising the use of a self-assembling unit comprising an S-layer fusion protein bound to a GPCR variant protein. In certain aspects, the devices and methods can be used for detecting the binding of a ligand to a GPCR and/or for detecting the presence of a GPCR ligand in a sample.

In certain embodiments, the invention encompasses a bioelectronic interface that comprises the solid substrate and the self-assembling unit as described herein. A bioelectronic interface is an interface or region where a biological molecule is in contact with a non-biological surface, such as a silicon wafer, treated glass, or graphene, which can produce a transmittable electronic signal. The bioelectronic interface is also a region where a potential ligand, ligand, or sample containing a ligand contacts or interacts with the functional biomolecule, for example, GPCR variant, wherein the binding is detected and/or measured and/or regulated using a bioelectronic device.

Figure 2:
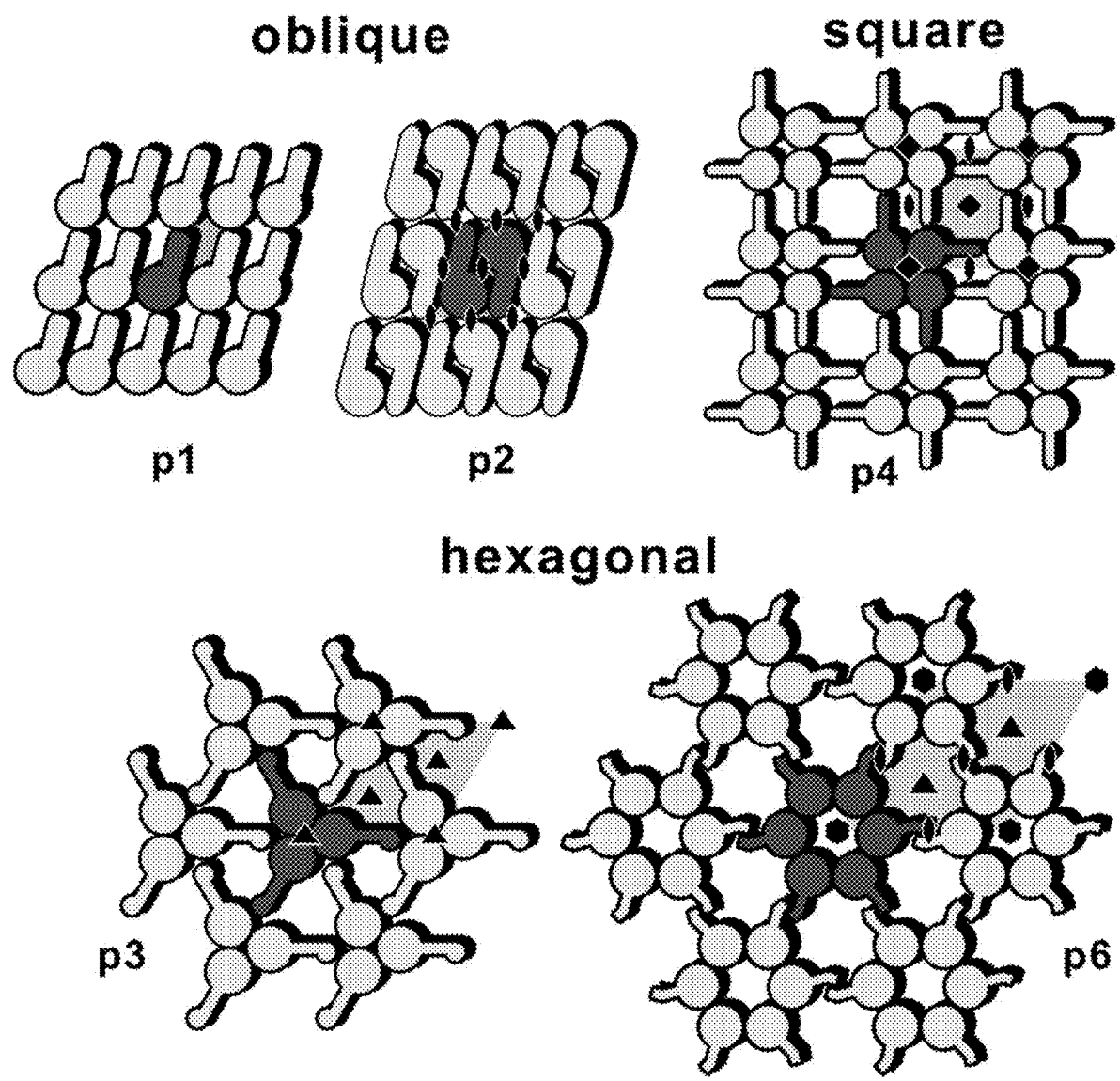
FIG. 2 is a schematic drawing of different S-layer lattice types.

The present invention utilizes bacterial surface layer (S-layer) proteins as a carrier to immobilize GPCRs on the surface of a substrate. Crystalline bacterial cell surface layers (S-layers) are monomolecular arrays of protein or glycoproteins that are found as the outermost cell envelope component of many bacteria and archeae forming a uniform protein sheet fully covering the bacterial cell at all stages of growth [A1], [A2] (reference numbers preceded by "A" correspond to Reference List A below). Their construction principle is based on a single type of protein or glycoprotein assembling into a highly ordered, porous array. An important property of isolated S-layer proteins is their ability to re-assemble into crystalline lattices on various materials and supports (including, for example, hydrophobic, hydrophilic, non-conducting, semi-conducting, and conducting surfaces) with the same physico-chemical properties found originally on the cell, thus forming stable uniform crystalline mono- or double layers. S-layer lattices are composed of identical species of subunits. They exhibit oblique, square, or hexagonal lattice symmetry (See FIG. 2). Unit cell dimensions are about 3 to about 30 nm with a thickness of about 5 to about 20 nm. S-layer proteins by nature carry functional domains in defined position and orientation that enable them to interact with other biomolecules in a highly controlled and well-organized way so that S-layers can be used as carriers for those biomolecules [A3, A4]. Via genetic engineering bioactive coatings based on fusion proteins comprising an S-layer and an introduced moiety with specific biological activity, such as a streptavidin-, Protein A, Protein G, an antibody- or antigen domain can be created [A5] [A6] [A7] [A8].

Figure 1A:
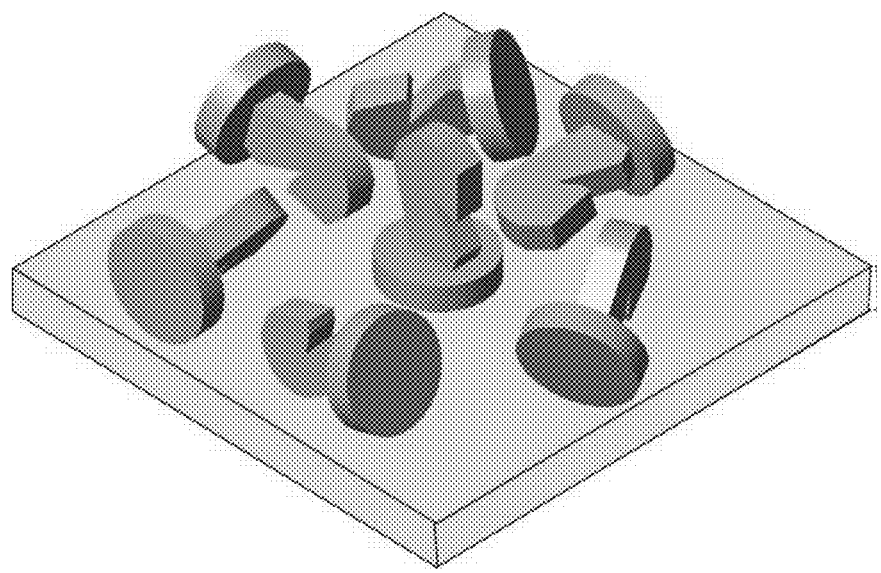
FIG. 1A is a drawing illustrating the deposition of functional molecule onto substrates with random orientation.
Figure 1B:
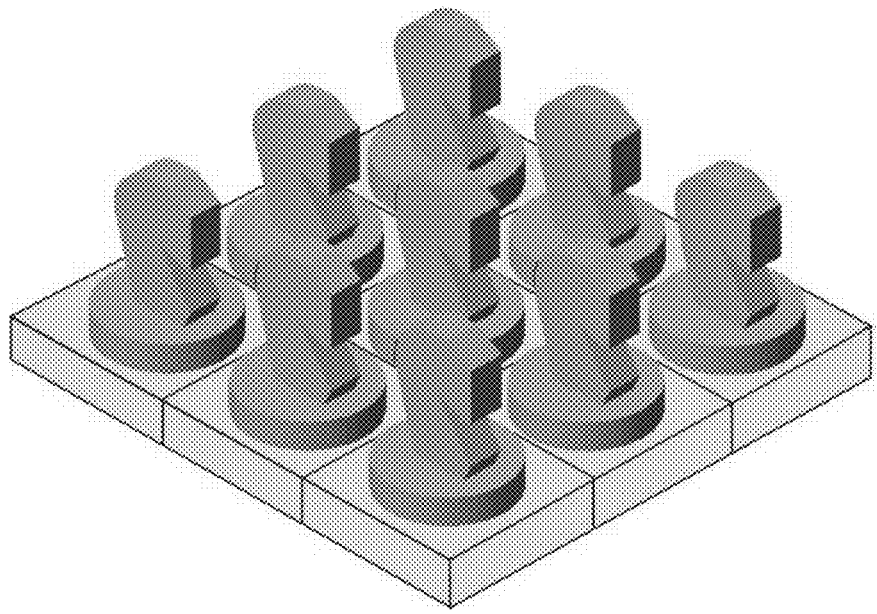
FIG. 1B is a drawing illustrating the orientation of functional molecules fused to S-layer proteins which are self-assembled into ordered crystalline lattice.

After isolation from the cell wall or in the case of recombinant S-layer proteins after extraction out of inclusion bodies, many S-layer proteins maintain the ability to self-assemble in suspension or to recrystallize on solid supports with the same repetitive physicochemical properties found originally on the cell, thus forming a stable uniform crystalline monolayer [A9], [A10], [A11], [A12]. Such crystalline S-layer fusion protein coatings allow for the reproducible, dense, oriented, and uniform presentation of binding sites while at the same time improving signal-to-noise ratios due to the intrinsic anti-fouling properties of the S-layer [A2], [A13, A14] [A15] opening a broad potential for application in biotechnology, molecular nanotechnology and biomimetics [A2]. FIG. 1 is a drawing depicting how S-layer proteins, which self-assemble into an ordered crystal lattice, can be used to guide the orientation of functional molecules, such as GPCR variants.

As used herein, the term "S-layer protein" encompasses polypeptides that are truncated as compared to naturally occurring S-layer proteins but which retain the ability to self-assemble. For example, the C-terminal truncated rSbpA$_{31-1068}$ is a commonly used molecular building block.

S-layer proteins are found in bacteria including, but not limited to, *Bacillus thuringiensis*, *Bacillus cereus*, *Lysiniba-* cillus sphaericus and *Geobacillus stearothermophilus*. In certain aspects, the S-layer protein is SbpA from *Lysinibacillus sphaericus* CCM. Wild-type (wt) SbpA protein can be directly extracted and purified from bacteria *Lysinibacillus sphaericus* (ATCC 4525). The S-layer protein SbpA from *Lysinibacillus sphaericus* CCM 2177 [A16] is an easy to handle coating system as the recrystallization can be induced by the addition of $CaCl_2$ to a monomeric protein solution. Self-assembly of the wtSbpA with long range order can occur on several solid surfaces, for example, silicon wafer, and can have a lattice parameter of about 13 nm. The S-layer protein can also be the S-layer protein from *G. stearothermophilus* PV72/p2. In certain aspects, the S-layer protein can be a recombinant protein. Recombinant S-layer proteins can, for example, be genetically-modified and expressed in a production organism, such as *E. coli*, in different truncated forms. Also, previous studies have demonstrated that domains of the S-layer at the C-terminus can be replaced by other moieties without interfering with the lattice structure. As the S-layer attaches via the N-terminus to the solid phase, the fusion domains remained exposed on the outermost surface of the protein lattice [A16] [A17]. The recombinant S-layer protein $rSbpA_{31-1068}ZZ$ comprising two IgG binding moieties from Protein A [A7] can be used to functionalize solid phases [A18]. Like Protein A, IgGs from distinct species can be bound via the Fc region at neutral or basic pH and subsequently eluted at acidic pH.

S-layer fusion proteins have been described in the literature. Such fusion proteins can comprise the self-assembling S-layer protein and a fused functional sequence (referred to herein as "the fusion domain"). The "fusion domain" of an S-layer fusion protein is a polypeptide that is fused to the S-layer proteins, for example, it can be fused directly to the S-layer protein or fused via a linker sequence to the S-layer protein. For example, the fusion protein comprising recombinant SbpA (rSbpA) can be constructed using rSbpA in its truncated form which retains its recrystallization property. The fusion domain can, for example, be streptavidin, an Fc binding region (for example, an Fc binding region from Protein A or the Fc binding region from Protein G), or antibody or antigen, or any other sequence or moiety that has binding affinity for the binding moiety of the GPCR variant fusion protein described herein. The fusion domain can be fused to an S-layer protein, for example, a C-terminally truncated S-layer protein. The C-terminally truncated S-layer protein can, for example, be the C-terminally truncated form of rSbpA. An S-layer-streptavidin fusion protein has also been described in Moll (2002), PNAS 99(23): 14646-14651. In addition, an exemplary S-layer fusion protein comprising the Fc binding domain of Protein A is the S-layer fusion protein $rSbpA_{31-1068}ZZ$ incorporating 2 copies of the 58 amino acid Fc-binding Z-domain (a synthetic analogue of the IgG binding domain of protein A from *Staphylococcus aureus*) (Völlenkle et al. (2004), Appl Environ Microbiol. 2004; 70:1514-1521. Highlight in Nature Reviews Microbiology 1512(1515), 1353 and Ilk et al. (2011), Curr Opin Biotechnol 22(6): 824-831, the contents of each of which are incorporated by reference herein in). Another exemplary S-layer fusion protein is a fusion protein comprising the Fc binding moiety of Protein G and rSbpA (for example, rSbpA GG described, for example, in Ucisik et al. (2015), Colloids Surf B Biointerfaces 128: 132-139). In certain aspects of the invention, the S-layer fusion protein is $rSbpA_{31-1068}ZZ$. The N-terminus of the S-layer fusion protein can be bound to the surface of the solid substrate and, as such, the fusion domain is fused to the C-terminus of the S-layer protein.

In certain embodiments, the fusion domain is an Fc binding region. An Fc binding region is a polypeptide capable of binding to the Fc of an antibody and includes Protein A, Protein G, Protein A/G, or a combination thereof, as well as a polypeptide comprising the binding regions of Protein A, Protein G, Protein A/G, or a combination thereof. Protein A is a 42 kD surface protein originally found in the cell wall of the bacterium *Staphylococcus aureus*. It contains five high-affinity IgG-binding domains (E, D, A, B, and C) capable of interacting with the Fc region from IgG of many mammalian species such as human, mouse, and rabbit. It binds the heavy chain within the Fc region of most immunoglobulins and also within the Fab region in the case of the human VH3 family. The Z domain of Protein A is an engineered analogue of the IgG-binding domain B. Protein G is an immunoglobulin-binding protein expressed in group C and G Streptococcal bacteria. It is a 65 kD (G148 protein G) and a 58 kD (C40 protein G) cell surface protein. Protein A/G is a recombinant fusion protein that combines IgG binding domains of both Protein A and Protein G. For example, Protein A/G may include four Fc binding domains from Protein A and two from Protein G. Protein A/G binds to all subclasses of human IgG, as well as to IgA, IgE, IgM and exhibiting some binding to IgD. Protein A/G also binds to all subclasses of mouse IgG.

Certain GPCR variants, as well as processes and computer systems for designing the variants have been described in detail in U.S. Patent App. Pub. Nos. 20120252719, 20150370960, and 20150370961, the contents of each of which are expressly incorporated by reference herein. These variants are rendered water-soluble by substituting a plurality of hydrophobic amino acids located in the transmembrane regions with polar amino acids as described more specifically herein. In specific aspects, the water-soluble GPCR variants are prepared by systematically changing a plurality of the seven-transmembrane α-helix hydrophobic residues leucine (L), isoleucine (I), valine (V), and phenylalanine (F) of a native protein to the hydrophilic residues glutamine (Q), threonine (T) and tyrosine (Y) (referred to herein as the "QTY replacement method" and the "QTY code") such that the variant has increased water solubility. In addition, two additional non-ionic amino acids Asn (N) and Ser (S) may also be used for the substitution for L, I and V but not for F. It is to be understood that Asn (N) and Ser (S) are envisioned as being substitutable for Q and T (as a variant is described) or L, I or V (as a native protein is described). Collectively, such variants may be referred to herein as "QTY variants" or "GPCR variants." Specific variants can be characterized by the name of the parent or native protein (e.g., CXCR4) followed by the abbreviation "QTY" (e.g., CXCR4-QTY or CXCR4 QTY or $CXCR4^{QTY}$) or the name of the protein or native protein followed by the word "variant" (e.g., "CXCR4 variant"). The GPCR variants possess the ability to bind the ligand which binds to the wild type or native protein and/or retains the ligand-binding activity of the wild-type or native protein. In addition, the GPCR variants comprise amino acid substitutions (QTY substitutions), as described herein, such that the GPCR variants are soluble in water.

The α-helix of a native GPCR is constructed from its polypeptide backbone with the side chains perpendicular to its axis. It can accommodate any of the amino acid side chains, but its stability depends on the context and nature of each side chain[B13] (reference numbers preceded by the letter "B" correspond to Reference List B below). All 20 amino acids are found in α-helices in the right environment', although some amino acids have higher propensities to form α-helices than others[B13]. Typical α-helices have characteristic traits: 100°, 1.5 Å per amino acid rise; 3.6 residues per 360°, 5.4 Å per α-helical turn[B13-14]. There are 3 types of α-helical backbone structures that are nearly identical according to crystallography data[B14]: 1) those comprised of mostly hydrophobic amino acids commonly found in transmembrane segments, as in GPCRs; 2) those comprised of both hydrophobic and hydrophilic amino acids, sometimes partitioned into two faces; and 3) those comprised of mostly hydrophilic amino acids, as in hemoglobin. Both hemoglobin and GPCRs are comprised of a high percentage of α-helices. Hemoglobin's structure is known to be comprised of ~80% α-helices[B15] and it is one of the most water-soluble proteins, at ~30% (~300 mg/ml) in red blood cells[B16]. However, without detergents GPCRs with 7 transmembrane (7TM) α-helices, are water-insoluble. Without wishing to be bound by theory, the QTY replacement method aims to convert water-insoluble α-helices (as in GPCRs) to water-soluble ones (as in hemoglobin) without significantly changing their structural properties or altering their surface charges.

Figure 6:
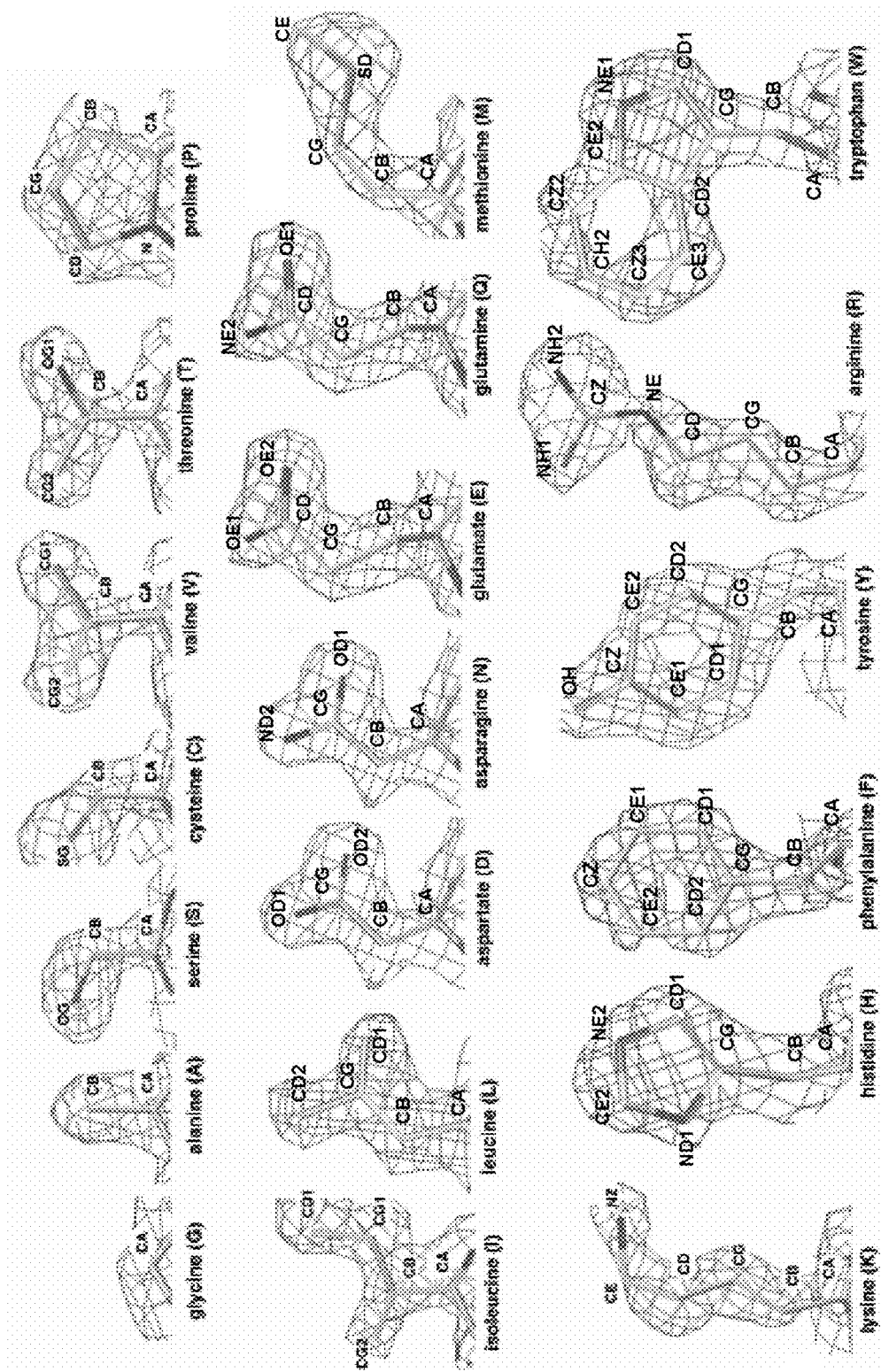
FIG. 6 shows experimental X-ray electron density maps (~1.5 Å) of the 20 amino acids. (people.mbi.ucla.edu/sawaya/m230d/Modelbuilding/modelbuilding.html. Courtesy of Dr. Michael R. Sawaya of University of California, Los Angeles, Calif., USA). The density maps clearly show the similarities between V and T; between L, D, N, E and Q; and between F and Y. In fact, the similarity between V and T is so striking that valine tRNA synthetase (ValRS) mischarges isoleucine and threonine at a rate of one per 200-400[B19-20]. These mistakes can later be corrected[B18].
Figure 7A:
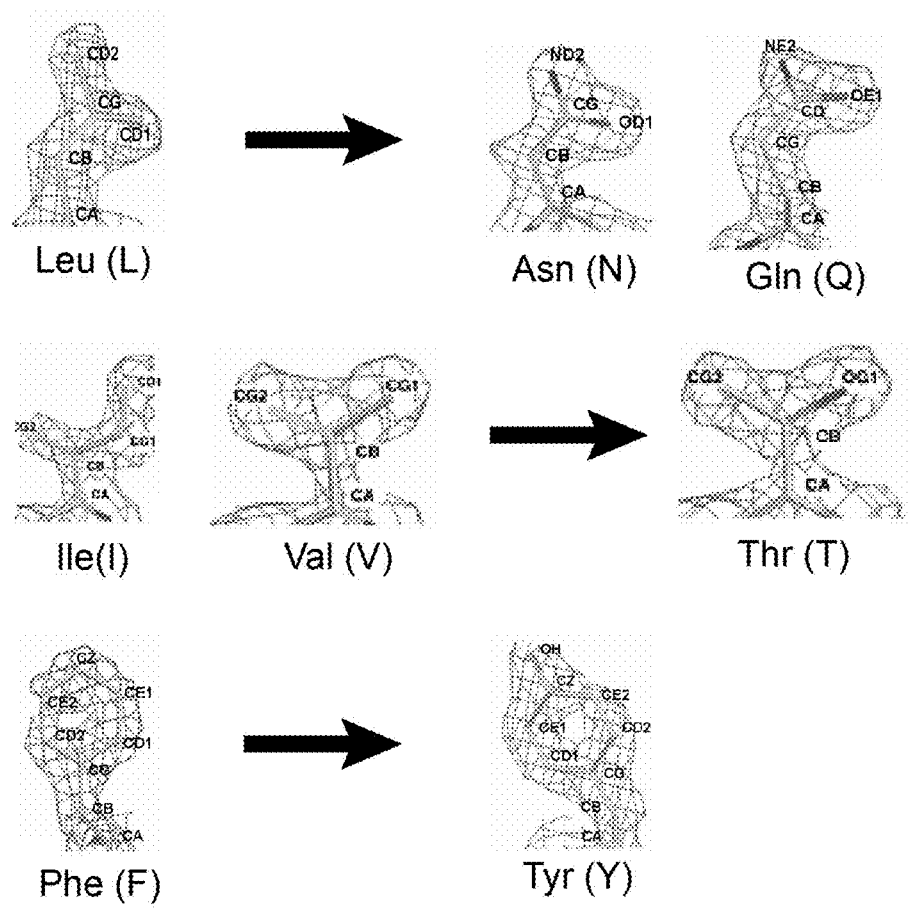
FIGS. 7A to 7D show how the QTY Code replaces L, V, I and F with Q, T and Y.
Figure 7B:
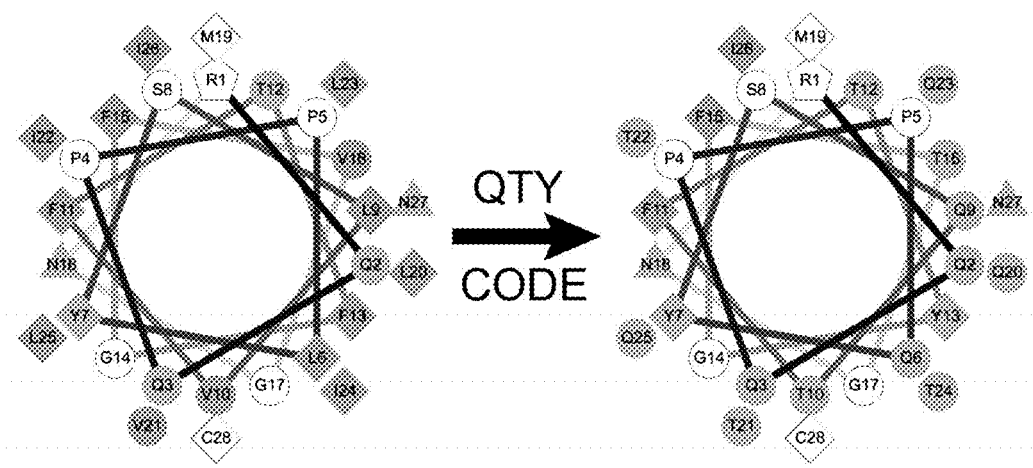
Figure 7C:
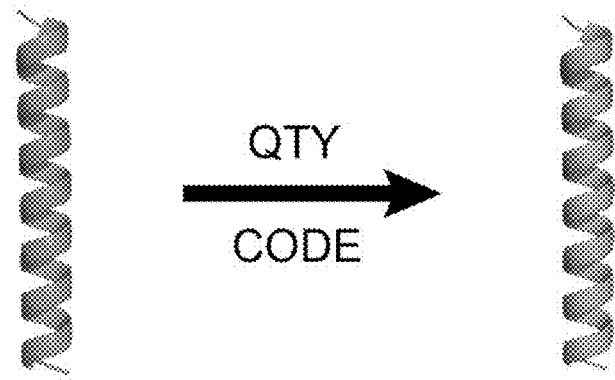
Figure 7D:
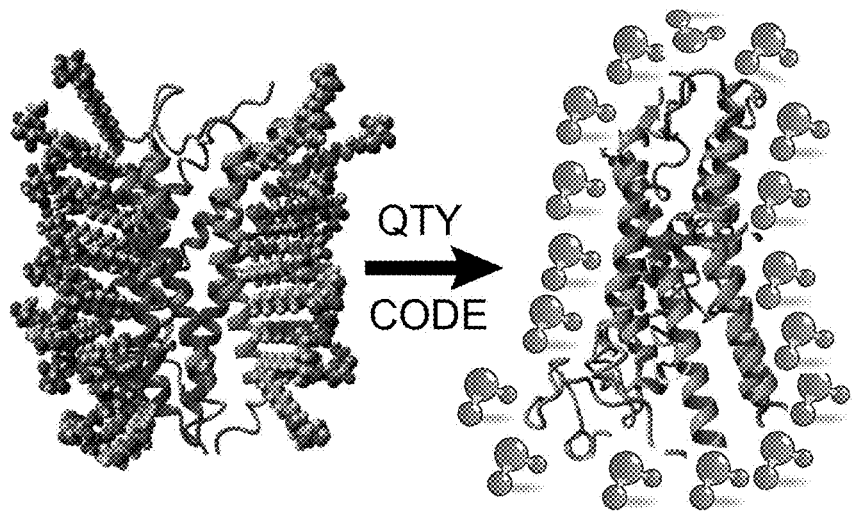
Figure 13:
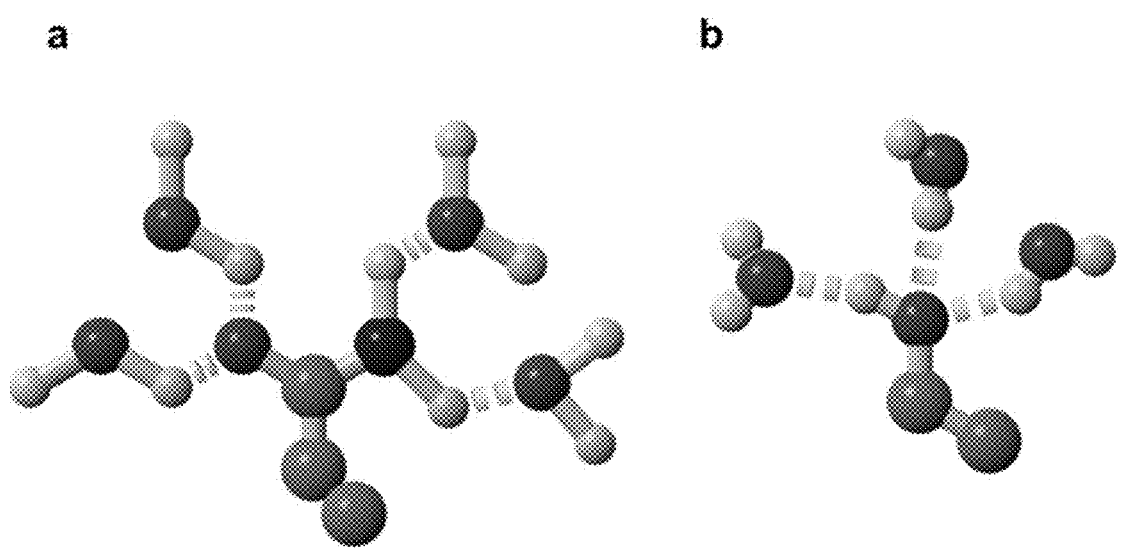
Figure 14A:
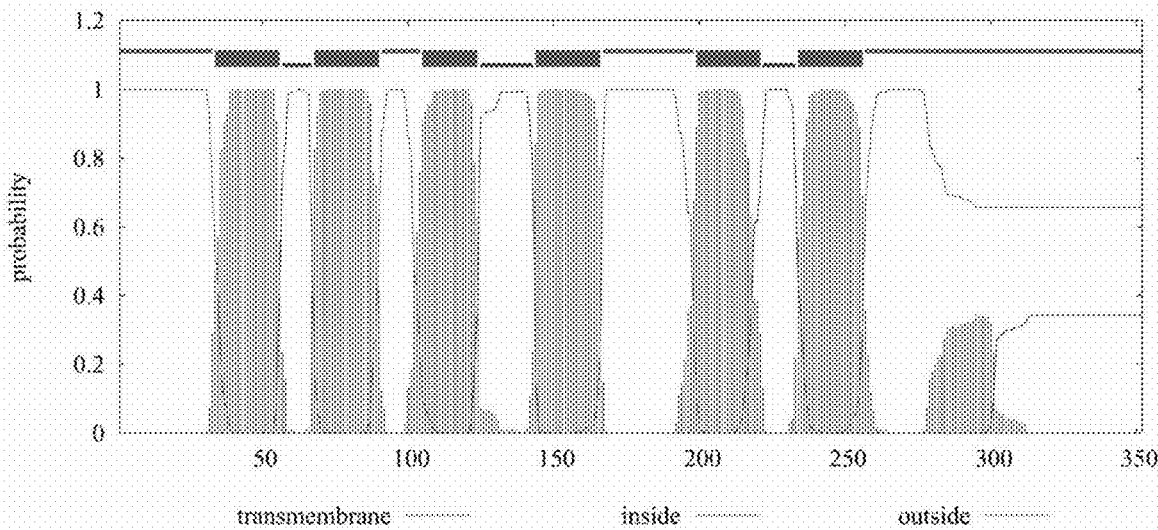
Figure 14B:
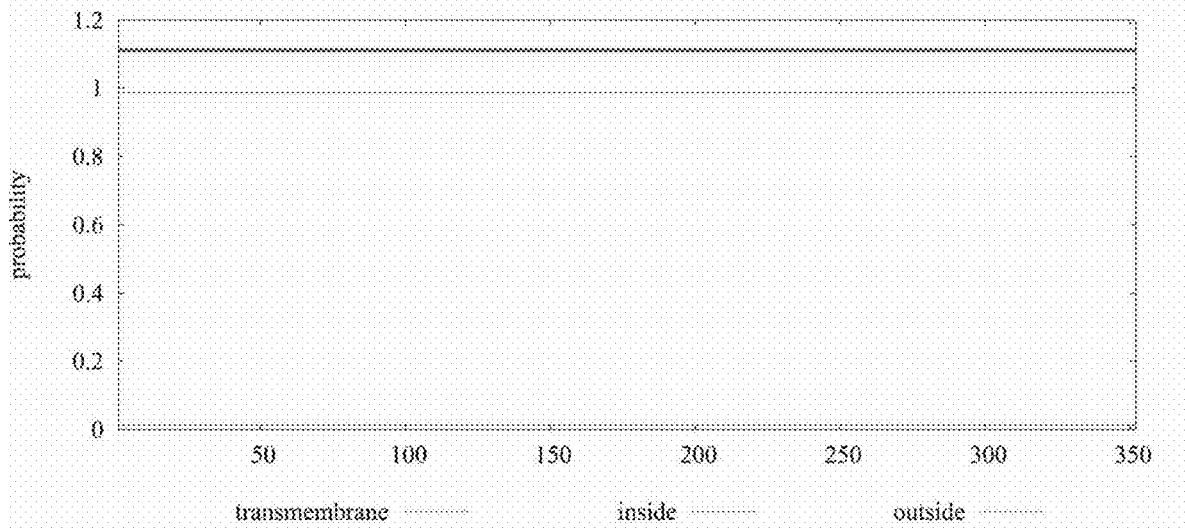
Figure 14C:
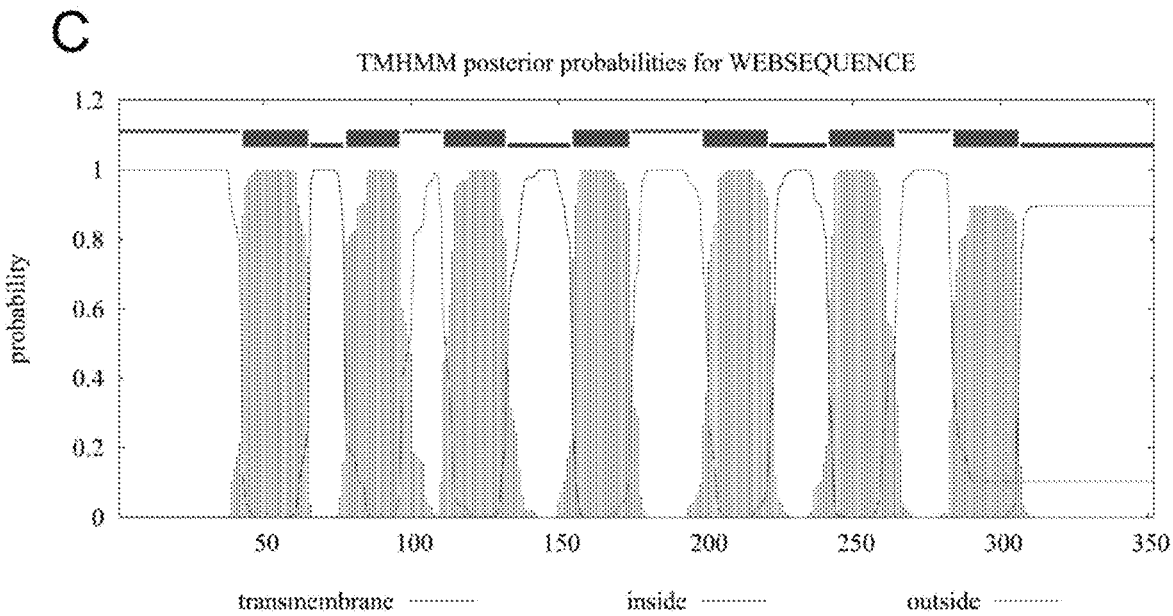
Figure 14D:
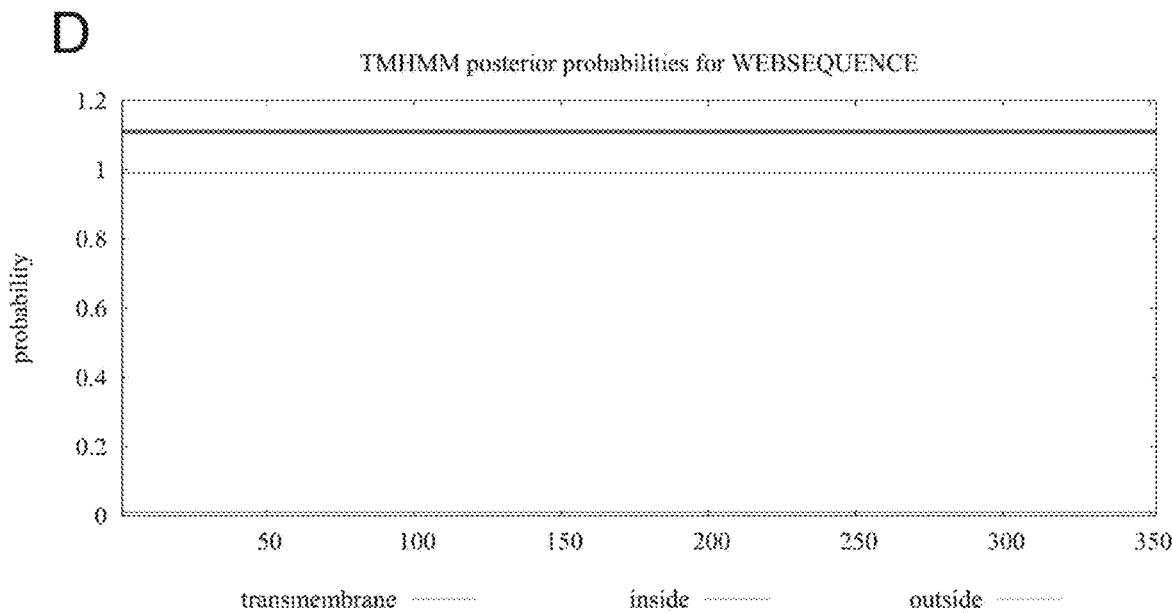
Figure 14E:
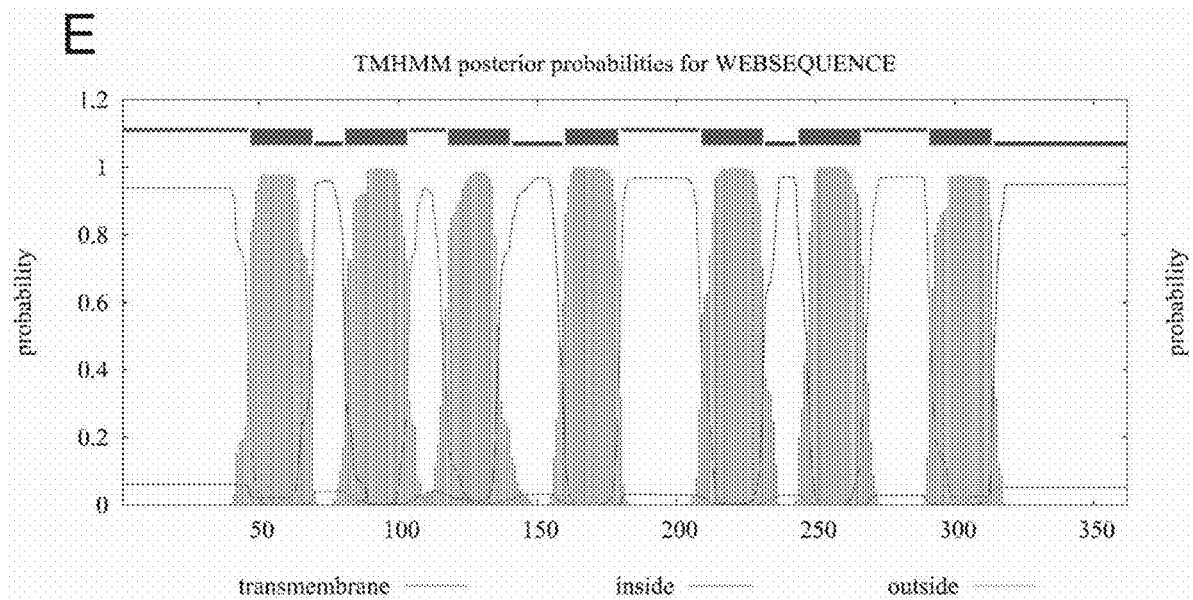
Figure 14F:
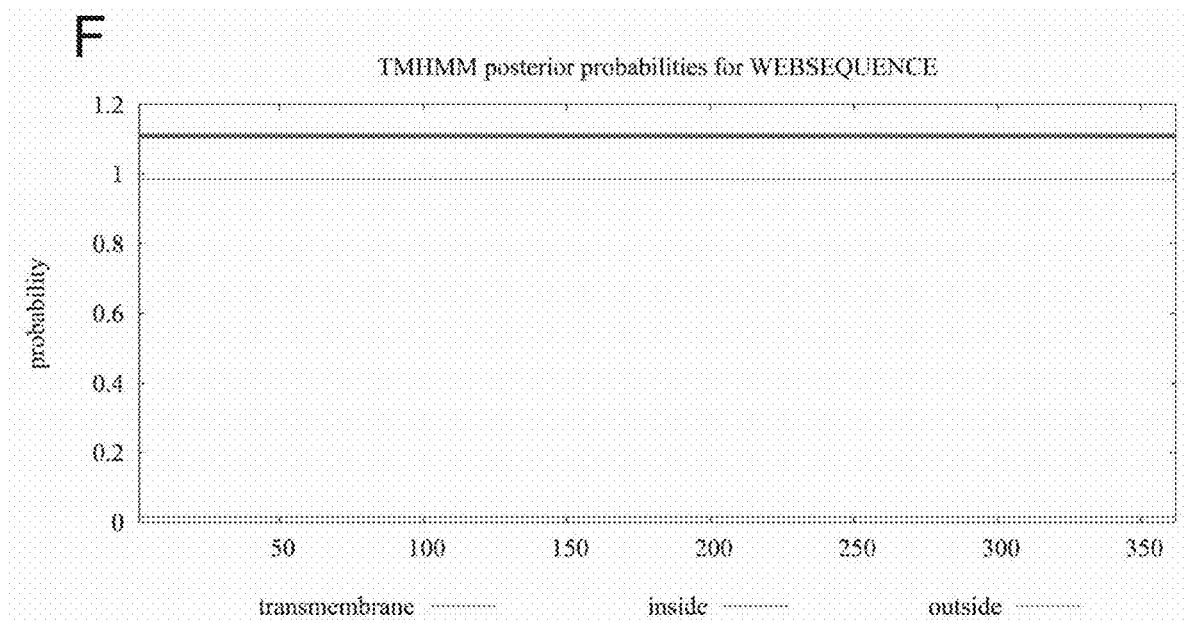
Figure 14G:
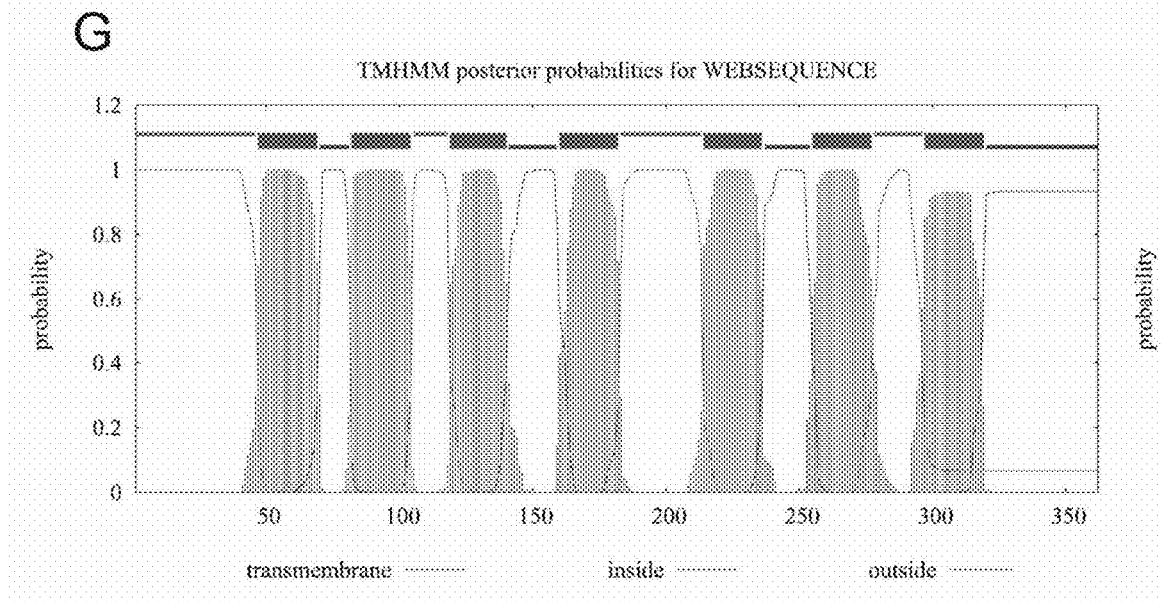
Figure 14H:
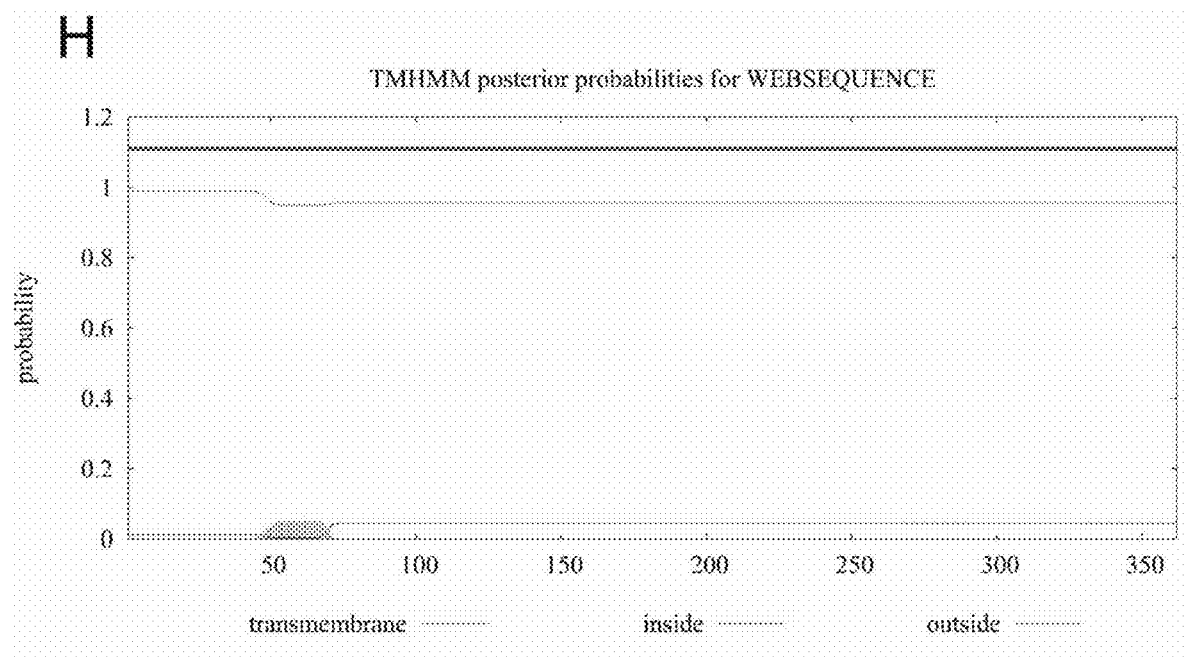

Several amino acid structures share strikingly similar crystallographic electronic density maps (FIG. 6 and FIG. 7A), but have very different chemical properties. For example, the density map of the hydrophobic leucine (L) is similar to the density maps of the hydrophilic asparagine (N) and glutamine (Q); the density map of the hydrophobic isoleucine (I) and valine (V) are similar to the density map of the hydrophilic threonine (T); and the density map of the hydrophobic phenylalanine (F) is similar to the density map of the hydrophilic tyrosine (Y). This similarity in density maps can lead to natural "amino acid confusion." For example, the valine (V) tRNA synthetase (ValRS)[B17] mischarges threonine (T) and isoleucine (I) at a rate of one per 200-400[18-19]. This similarity in electron density maps forms the basis of the QTY Code which involves the following substitutions: L→Q, I & V→T, and F→Y (FIG. 7A). These residue substitutions are made in order to increase receptor water-solubility while minimally affecting structural properties. The side chains of L, V, I and F cannot form any hydrogen bonds with water, which renders them water-insoluble. On the other hand, Q can form 4 hydrogen bonds with 4 water molecules (2 as hydrogen donors and 2 as hydrogen acceptors). Likewise, the —OH groups of T and of Y can form 3 hydrogen bonds with 3 water molecules (2 H-acceptors and 1 H-donor) (FIG. 13). Because Q is water soluble, it is the choice to replace L. Furthermore, both L and Q have high tendencies to form α-helices and can stabilize the same structure[20]. Although N has similar properties to Q, it prefers turns and is involved in glycosylations in eukaryotes. Thus Q, but not N, is preferred to replace L. Similarly, because T and Y are water-soluble, they are used to replace I, V and F.

As discussed above, in certain aspects, the hydrophilic residues (which replace a plurality of hydrophobic residues in the α-helical domain of a native membrane protein) are selected from the group consisting of glutamine (Q), threonine (T), tyrosine (Y) and any combination thereof. In additional aspects, the hydrophobic residues selected from leucine (L), isoleucine (I), valine (V) and phenylalanine (F) are replaced. Specifically, the phenylalanine residues of the α-helical domain of the protein are replaced with tyrosine; the isoleucine and/or valine residues of the α-helical domain of the protein are replaced with threonine; and/or the leucine residues of the α-helical domain of the protein are replaced with glutamine.

As described herein, the water-soluble polypeptides of the invention possess the ability to bind the ligand which normally binds to the wild type or native GPCR. In preferred embodiments, the amino acids within potential ligand binding sites of the native GPCR are not replaced and/or the sequences of the extracellular and/or intracellular domains of the native protein are identical to those of the GPCR variant. In another embodiment, the water-soluble polypeptide retains at least some of the ligand-binding activity of the GPCR. In a further embodiment, one or more amino acids within potential ligand binding sites of the native membrane protein are not replaced. In some embodiments, the native GPCR (upon which the GPCR variant is based) is mammalian.

The variants comprise a modified α-helical domain, wherein the modified α-helical domain comprises an amino acid sequence in which a plurality of hydrophobic amino acid residues within a α-helical domain of a native membrane protein is replaced with hydrophilic amino acid residues thus rendering the variant water-soluble, as described herein. In certain aspects, key residues at the α-helical positions b, c, f that usually face the hydrophilic surface are replaced, while maintaining the hydrophobic residues at α-helical positions a, d, e, g. An exemplary GPCR variant is a variant where residues Leucine (L), isoleucine (I), valine (V), and phenylalanine (F) in hydrophilic surface α-helical positions b, c and f but not positions a, d, e, and g within the seven-transmembrane α-helical domain of the GPCR with glutamine (Q), threonine (T), threonine (T), and tyrosine (Y). In additional aspects, the variant GPCR is a GPCR wherein a plurality of hydrophobic amino acids in the transmembrane (TM) domain α-helical segments of the GPCR are substituted, wherein:

(a) said hydrophobic amino acids are selected from the group consisting of Leucine (L), Isoleucine (I), Valine (V), and Phenylalanine (F);

(b) each said Leucine (L) is independently substituted by Glutamine (Q), Asparagine (N), or Serine (S); preferably, Glutamine (Q);

(c) each said Isoleucine (I) and said Valine (V) are independently substituted by Threonine (T), Asparagine (N), or Serine (S); preferably, Threonine (T); and, (d) each said Phenylalanine is substituted by Tyrosine (Y).

In an additional example, the GPCR variant comprises a modified α-helical domain, wherein:

(a) the modified α-helical domain comprises an amino acid sequence in which a plurality of hydrophobic amino acid residues within the α-helical domain of a G-protein coupled receptor (GPCR) selected from the group consisting of phenylalanine, isoleucine, valine and leucine are replaced with hydrophilic, non-ionic amino acid residues, and wherein (b) the pI of the GPCR variant is substantially the same as the pI of the corresponding native GPCR polypeptide. In certain embodiments, the pI of the GPCR variant is substantially the same as the corresponding native GPCR when any difference in pI (between the native GPCR and the GPCR variant) is less than about 7%, less than about 6%, less than about 5%, less than about 4%, or less than about 3%.

In yet a further aspect, the majority (greater than about 50%) of hydrophobic residues, phenylalanine, isoleucine, valine and leucine, within the seven-transmembrane domain, are replaced with the hydrophilic, non-ionic amino acid residues. In a further aspect, at least about 60%, at least about 65%, at least about 70%, at least about 75%, at least about 80%, at least about 85%, at least about 90%, at least about 95%, at least about 98%, at least about 99%, or all of the hydrophobic residues, phenylalanine, isoleucine, valine and leucine, within the seven-transmembrane domains are replaced with hydrophilic, non-ionic amino acid residues. In certain embodiments, the variant GPCR is a variant chemokine receptor wherein at least about 90%, at least about 95%, at least about 98%, at least about 99%, or all of the hydrophobic residues, in the native chemokine receptor are replaced using the QTY code as described herein.

In a further embodiment, the GPCR (in other words, the native GPCR which is modified to form the variant GPCR) is selected from the group comprising purinergic receptors ($P2Y_1$, $P2Y_2$, $P2Y_4$, $P2Y_6$), $M_1$ and $M_3$ muscarinic acetylcholine receptors, receptors for thrombin [protease-activated receptor (PAR)-1, PAR-2], thromboxane (TXA2), sphingosine 1-phosphate ($S1P_2$, $S1P_3$, $S1P_4$ and $S1P_5$), lysophosphatidic acid ($LPA_1$, $LPA_2$, $LPA_3$), angiotensin II ($AT_1$), serotonin (5-$HT_{2c}$ and 5-$HT_4$), somatostatin (ssts), endothelin (ETA and ETB), cholecystokinin ($CCK_1$), $V_{1a}$ vasopressin receptors, $D_5$ dopamine receptors, fMLP formyl peptide receptors, $GAL_2$ galanin receptors, EP3 prostanoid receptors, $A_1$ adenosine receptors, cu adrenergic receptors, $BB_2$ bombesin receptors, $B_2$ bradykinin receptors, calcium-sensing receptors, chemokine receptors, KSHV-ORF74 chemokine receptors, $NK_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4. In certain aspects, the GPCR is a chemokine receptor, including, for example, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2.

In certain additional aspects, the GPCR is an olfactory receptor. Olfactory receptor neurons (olfactory cells) are bipolar nerve cells that densely line the olfactory membrane in the recess of the nose, wherein odor receptor proteins that respond to odor molecules are expressed at high density. In olfactory cells, the chemical substances diffusing in the air from the stimulus source are detected by olfactory receptors and converted to neural signals. The interaction of odorants with olfactory receptors on the apical cilia of olfactory neurons is the first step in the perception of smell. The large number (e.g., approximately ~380 in human and ~1200 in dog) and structural diversity of the opsin-like GPCRs that function as olfactory receptors underlies the ability to detect and discriminate a vast number of volatile compounds (Buck, L. and Axel, R., *Cell* 65: 175-187, 1991; Fuchs, T. et al., *Hum. Genet.* 108: 1-13, 2001). Olfactory receptors interact with a diverse array of volatile molecules. It is widely accepted that every odorous molecule binds to several ORs and vice versa. This binding pattern generates a unique combinatorial code that generates a specific aroma for each odorant and enables the organism to distinguish it from other molecules. In some embodiments, the GPCR is a mammalian olfactory receptor. In another embodiment, the olfactory receptor is selected from the group consisting of OR17-4, OR23 and S51. In another embodiment, the olfactory receptor is selected form the group consisting of hOR17-4 (human), mOR23 (mouse), mS51. In yet another embodiment, the olfactory receptor is hOR17-4.

As described above, the variant GPCR fusion protein comprises variant GPCR as described herein fused to a binding moiety. The binding moiety is a polypeptide sequence that is fused to the variant GPCR, for example, it can be fused directly to the variant GPCR or is fused via a linker to the variant GPCR. The binding moiety is a polypeptide that is capable of binding to the S-layer fusion protein (more specifically, the fusion domain of the S-layer fusion protein). Thus, where the S-layer fusion protein comprises an Fc-binding region, the variant GPCR is modified with an Fc region. In another example, where the S-layer fusion protein comprises streptavidin, the GPCR variant fusion protein comprises streptavidin binding peptide, optionally biotin. In yet further aspects, when the S-layer fusion protein comprises an antibody or an antigen-binding portion thereof, the binding moiety of the GPCR variant fusion protein is an antigen that binds to the antibody or the antigen-binding portion thereof. In yet a further aspect, the fusion domain of the S-layer protein is an antigen and the binding moiety of the GPCR variant is an antibody or antigen-binding portion thereof that binds to the antigen. Because the ligand binding domain of the GPCR is at the N-terminal portion of the GPCR, the binding moiety can be fused at the C-terminus of the GPCR variant.

In certain aspects, the binding domain is an Fc. An "Fc" is an Fc region or a polypeptide that corresponds to the portion of an antibody or immunoglobulin molecule that interacts with effector molecules and cells and/or corresponds to the crystallizable fragment obtained by papain digestion of an IgG. As used herein, the term "Fc region" also encompasses polypeptide or amino acid sequences comprising an Fc. The term "Fc region" can also include a fragment of the Fc domain or a polypeptide or amino acid sequence comprising the fragment, wherein the fragment has one or more biological activity of the full Fc. In certain aspects, of the present invention the Fc region is a human Fc region or has an amino acid sequence of a human Fc region. In yet additional aspects, the Fc region is a human IgG1 Fc domain.

The self-assembling unit comprising the GPCR variant fusion protein bound to the S-layer fusion protein is formed as a result of the binding affinity between the fusion domain of the S-layer fusion protein for the binding moiety of the GPCR variant. The N-terminus of the S-layer fusion protein binds to the solid substrate or support. Thus, the self-assembling unit bound to the surface of the substrate can comprise elements arranged as follows:

Substrate Surface—[N—S-layer protein-C-Fusion Domain]—[Binding Moiety-C-GPCR variant-N];
wherein "N" and "C" indicate the N and C-termini, respectively, and wherein—represents attachment of the S-layer fusion protein to the substrate surface and binding of the fusion domain of the S-layer fusion protein to the binding moiety of GPCR variant fusion protein. The elements of the self-assembling units and the formation of the two-dimensional pattern is described in more detail in FIGS. 20 to 23.

Figure 21:
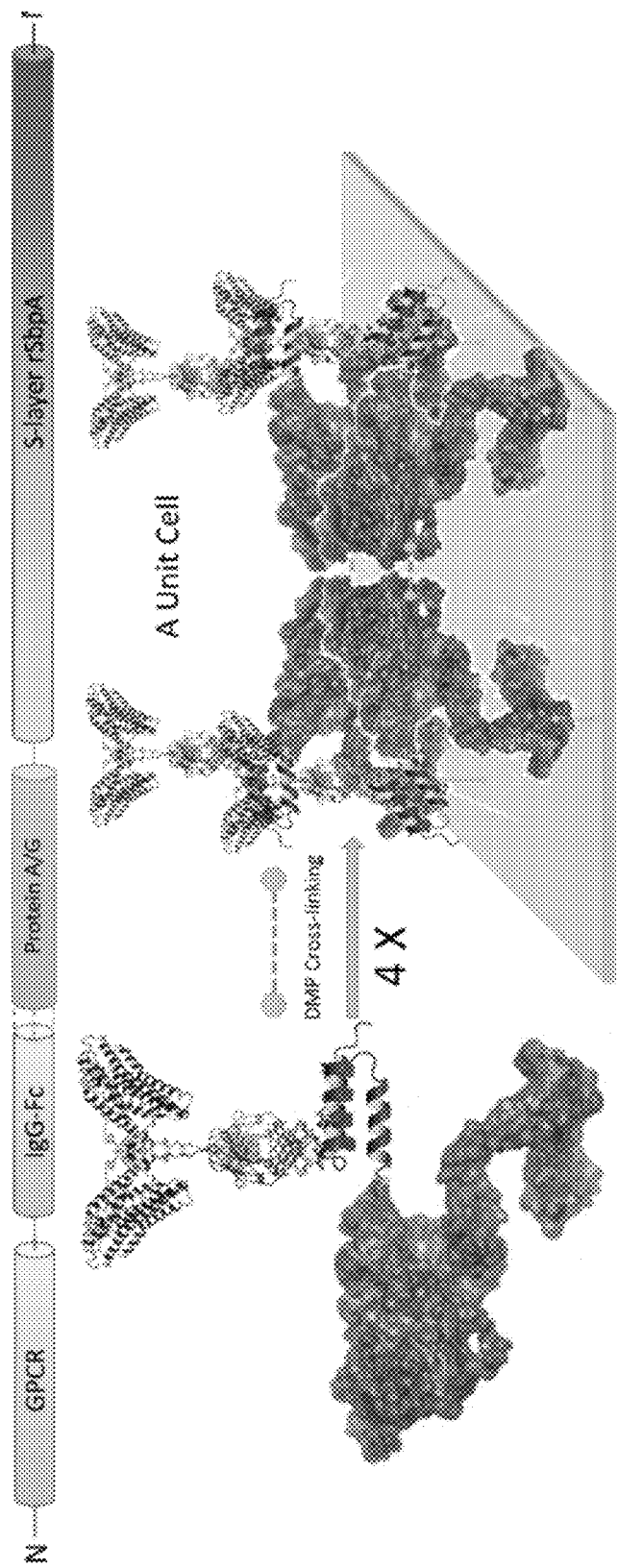
FIG. 21 shows the functional block that forms the two-dimensional pattern on the surface. Specifically, a single unit cell of a self-assembled GPCR-Fc binded rSbpA-Protein A/G two-dimensional lattice is shown.
Figure 22:
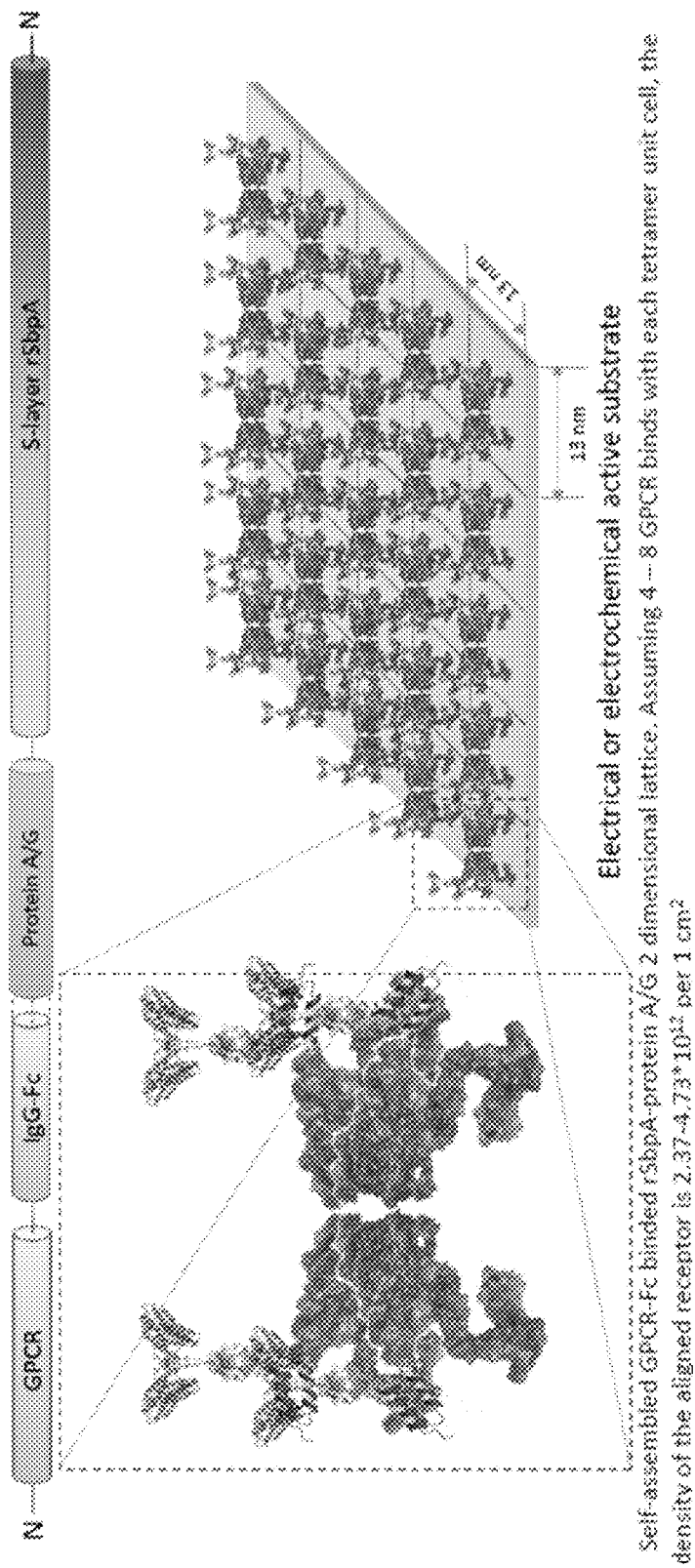
FIG. 22 shows the two-dimensional lattice of functional protein arrays. The figure shows the self-assembled GPCR-Fc binded rSbpA-protein A/G two-dimensional lattice. Assuming 4-8 GPCR bind with each tetramer unit cell, then the density of the aligned receptor is 2.37 to 4.73×10$^{12}$ per 1 cm$^2$.
Figure 23:
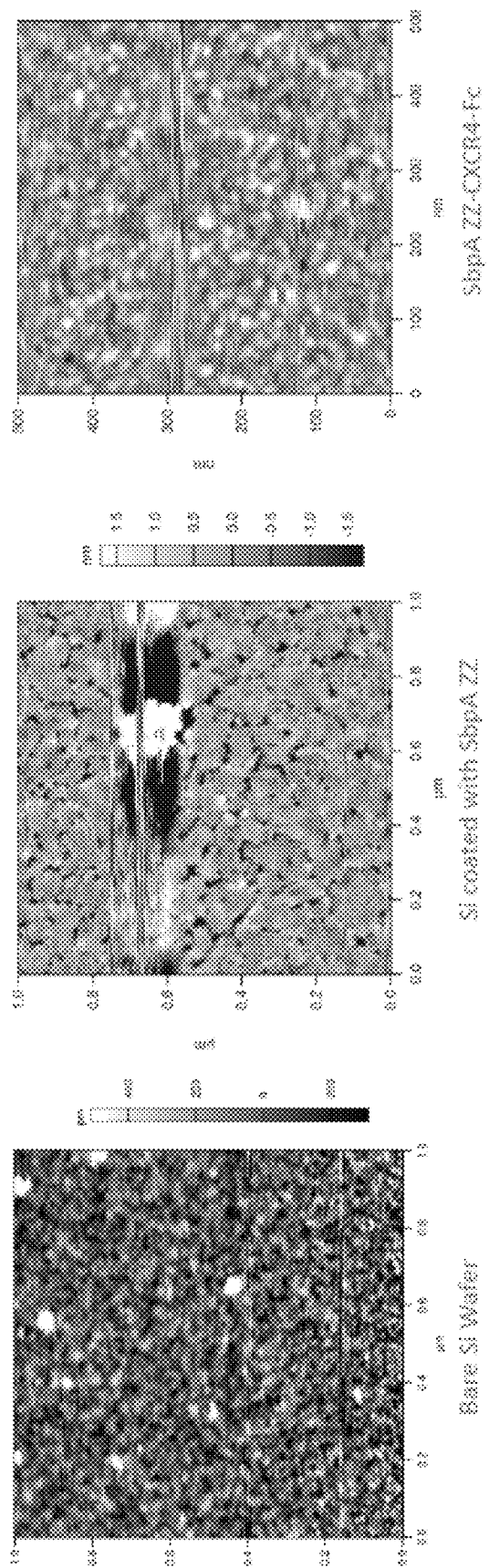
FIG. 23 shows atomic force microscopy (AFM) images of the double layer coated surface. Using the Cypher AFM system, the surface morphology of the coated proteins on Si wafer was determined. This system is formed to two monolayers of fusion proteins.

The self-assembling units or S-layer proteins can be attached to the solid substrates, for example, contacting the substrate with the self-assembling units followed by cross-linking the self-assembling units described herein. Alternatively, the surface of the substrate is first functionalized with the S-layer fusion proteins and then contacted with the GPCR variant fusion protein which binds to the S-layer fusion protein (thus forming the self-assembling unit after attachment of the S-layer protein to the surface). Certain S-layer proteins fold into tetramers which form the crystalline lattice. The S-layer tetramer can have a dimension of about 13 $nm^2$ per 2D unit. If 4 to 8 GPCR variant proteins bind with each tetramer unit cell, then the density of the receptor on the surface is about 2.37 to about $4.37 \times 10^{12}$ per 1 $cm^2$. For example, for a conducting surface of about 13 $mm^2$ (about 1.3 $cm^2$), for example, a chip, the density would be about 8×10² molecules/13 mm². The N-terminus of the S-layer protein fusion protein can bind to a substrate surface thus immobilizing the GPCR variant on the substrate surface and orienting the GPCR variant fusion protein in a position where it is capable of binding to a ligand, for example, the GPCR variant fusion protein is the outermost layer on the substrate (FIG. 21).

The S-layer protein can also be attached to a surface using a bonding agent such as secondary cell wall polymers (SCWP) of prokaryotic microorganisms as described, for example, in U.S. Pat. No. 7,125,707, the contents of which are expressly incorporated by reference herein.

Cross linking of recrystallized S-layer self-assembling units on a substrate will result in increased stability as the cross-linking will occur within the S-layer subunits (inter- and intra-molecular) and in the presence of amino-groups on the surface also between the S-layer protein coating and the substrate. Dependent upon the application, cross-linking is not necessary; but if desired or needed (applying a pH shift; stability issues), cross-linking can be performed after the coating process when the S-layer fusion proteins are in a binding active state; or after the binding of the GPCR fusion protein to covalently link the GPCR fusion protein to the S-layer fusionprotein.

Methods of depositing S-layer proteins on a carrier surface or on a solid support are described in detail in U.S. Patent App. Pub. No. 2004/0137527 A1, the contents of which are expressly incorporated by reference herein. In order to deposit S-layer proteins or the self-assembling unit comprising the S-layer protein on a solid substrate, a solution comprising monomers or oligomers of the S-layer protein or the self-assembling units is brought into contact with the solid support or carrier surface resulting in the formation of a two-dimensional crystalline lattice on the surface of the substrate in the presence of $CaCl_2$. The S-layer proteins self-assemble into a 2D crystalline layer. The stability of S-layers can be enhanced with the use of cross-linkers, for example, dimethyl pimelimidate. In addition, the stability of the crystalline protein layers on silicon supports has been shown to be increased by using amino-amino group directed cross-linkers, such as glutaraldehyde and bis(sulfosuccinimidyl)superat, amino-carboxyl group directed cross-linkers including, for example, 1-ethyl-3-(3-dimethylaminopropyl)carbodiimide (Gyorvary et al., 2003. Journal of Microscopy 212(3): 300-306).

The ability of S-layer proteins to self-assemble on a variety of surfaces has been described in the art (See, for example, Ilk et al. (2008), Colloids and Surfaces 321: 163-167, U.S. Pat. App. Pub. No. 2004/0137527, and U.S. Pat. No. 7,262,281, the contents of each of which are expressly incorporated by reference herein). S-layer proteins and the self-assembling units can self-assemble on surfaces including, for example, polystyrene surfaces, silicon wafers (SiO2, Si3N4, hydrophilic, and/or hydrophobic), gold wafers, glass, metal oxide surfaces (for exmaple, aluminum oxide, indium tin oxide), stainless steel, modified graphene, carbon nanotubes, and poly-lysine modified surfaces. A solid substrate is a solid carrier or solid support having a surface to which the S-layer protein can bind. In some aspects, the surface is an inorganic surface. In additional aspects, the surface is hydrophobic or hydrophilic. Non-limiting examples of solid substrates, and more specifically, diagnostic tools that can be coated with S-layer proteins as described herein, include magnetic beads with various surface modifications, ELISA plates, silica beads, filling materials for column chromatography, coating resins for blood purification, and polyamide membranes. In addition, the S-layer proteins can be recrystallized as a layer on single- and multi-walled carbon nanotubes using methods similar to those used for flat solid supports or nanoparticles. Using the coated carbon nanotubes to build a hierarchical 3D matrix can result in an increase in the number of binding sites per unit area and can potentially improve signal to noise ratio. As shown in Table A below, after crosslinking very stable coatings can be achieved; e.g., rSbpA ZZ (S-layer fusion protein comprising the IgG binding domain of Protein A) coated surfaces: The percentage of retained IgG binding activity is shown after exposure to high temperature or various chemical solutions:

TABLE A

| 20 min treatment | Silicon wafer | Glass slides | Epoxy glass slides | Polystyrene slabs |
| --- | --- | --- | --- | --- |
| 95° C. | 84 | 66 | 87 | 98 |
| 0.1M NaOH | 55 | 82 | 86 | 96 |
| DMSO | 87 | 83 | 87 | 93 |
| THF | 88 | 77 | 96 | 100 |
| 2M GHCL | 83 | 79 | 91 | 100 |
| 5M GHCL | 81 | 94 | 95 | 90 |
| 3.0M Urea | 87 | 95 | 93 | 98 |
| 6.5M Urea | 76 | 96 | 95 | 100 |

In certain specific aspects, the surface is a semi-conducting or conducting surface, including, but not limited to, silicon, gold, conducting polymers, carbon nanotubes, and graphene. For example, rSbpA recrystallizes on many semi-conductive surfaces widely used as substrates in the semiconductor industry. The surface can, for example, be a silicon wafer, a silicon dioxide-coated silicon wafer, indium tin oxide (ITO) coated glass, or $TiO_2$—$SiO_2$ hybrid sol-gel coated glass. In an additional example, the substrate can be surface-treated with poly-l-lysine, for example, poly-l-lysine-treated gold. In certain additional aspects, the substrate can be flexible plastic, for example, ITO coated plastic film, graphene coated film, or $TiO_2$—$SiO_2$ hybrid sol-gel coated film. In certain additional aspects, the solid support is a sensor chip of a surface plasmon resonance system.

In certain aspects, the modified substrates or bioelectronic interfaces described herein, for example, a chip or a wafer, can be dried (for example, with or without trehalose) without disrupting the two-dimensional lattice structure. The S-layer proteins function as a "polymer cushion" delaying or preventing denaturation of the functional domain. In certain cases, the substrate or interface can be used up to at least up to about 1 month, at least up to about 2 months, at least up to about 3 months, at least up to about 6 months, at least up to about 1 year, or at least up to about 2 years after manufacturing.

The invention permits fabrication of a surface with a high density of GPCRs. For example, as described above, the density of GPCRs on the surface can be about 2.37 to about 4.37×10¹² per 1 cm². In certain embodiments, at least two different GPCR variants are immobilized on the substrate. For example, at least two different chemokine receptor variants (for example, CXCR4 and CCR5 variants) can be immobilized on the surface. Alternatively, at least two different olfactory receptors can be immobilized on the substrate. In certain embodiments, at least five, or at least ten, or at least twenty different GPCR variants are immobilized on the substrate. The presence of at least two different GPCR variants allow a potential ligand to be screened for binding to the at least two different GPCRs and/or allowing a sample to be screened for the presence of different ligands that bind to the at least two different GPCRs.

The bioelectronic interface, surface-modified substrate, and devices described herein can be used to detect the binding of a potential ligand to the variant GPCR. In addition, the invention encompasses a method for screening for a ligand of a G-protein coupled receptor (GPCR) comprising the steps of contacting a potential ligand with a variant GPCR immobilized on a solid substrate, wherein the variant GPCR is part of a self-assembling unit that comprises a variant GPCR fusion protein bound to an S-layer fusion protein; and measuring the binding of the potential ligand to the variant GPCR, wherein the binding of the potential ligand to the variant GPCR is indicative of binding to the native GPCR. The potential ligand can, for example, be a small molecule. In some aspects, potential ligand is a compound from a chemical library and/or a combinatorial library. In additional aspects, the potential ligand is selected from the group consisting of a small molecule, an ion, a polypeptide, a polynucleotide, a lipid, a hormone analog, a peptide, a peptide-like molecule (peptidomimetic), an antibody, an antibody fragment, and an antibody conjugate.

The bioelectronic interface, surface-modified substrate, and devices described herein can be used to detect the presence of a GPCR ligand in a sample. In addition, the invention encompasses a method for detecting the presence of a GPCR ligand in a sample comprising the steps of contacting the sample with a variant GPCR immobilized on a solid substrate, wherein the variant GPCR is part of a self-assembling unit that comprises a variant GPCR fusion protein bound to an S-layer fusion protein; and measuring the binding of the ligand to the variant GPCR, wherein the binding of the potential ligand to the variant GPCR is indicative of binding to the native GPCR. In certain aspects, the sample can be screened against multiple different GPCRs. Such a method would allow the sample to be screened for the presence of a ligand of any of the multiple different GPCRs and/or permit detection of more than one GPCR ligand in the sample. Non-limiting examples of samples that can be screened include, air samples, gas samples, liquid samples, biological samples including biological fluid samples, and soil samples. In certain aspects, the sample is an air sample and the GPCR variant is an olfactory receptor or multiple olfactory receptors. In yet additional aspects, the sample is a biological sample, including, for example, blood, blood plasma, blood serum, saliva, sweat, tears, urine, feces, breath or breath condensate. The biological sample can, for example, be obtained from a human patient or an animal subject.

Figure 24:
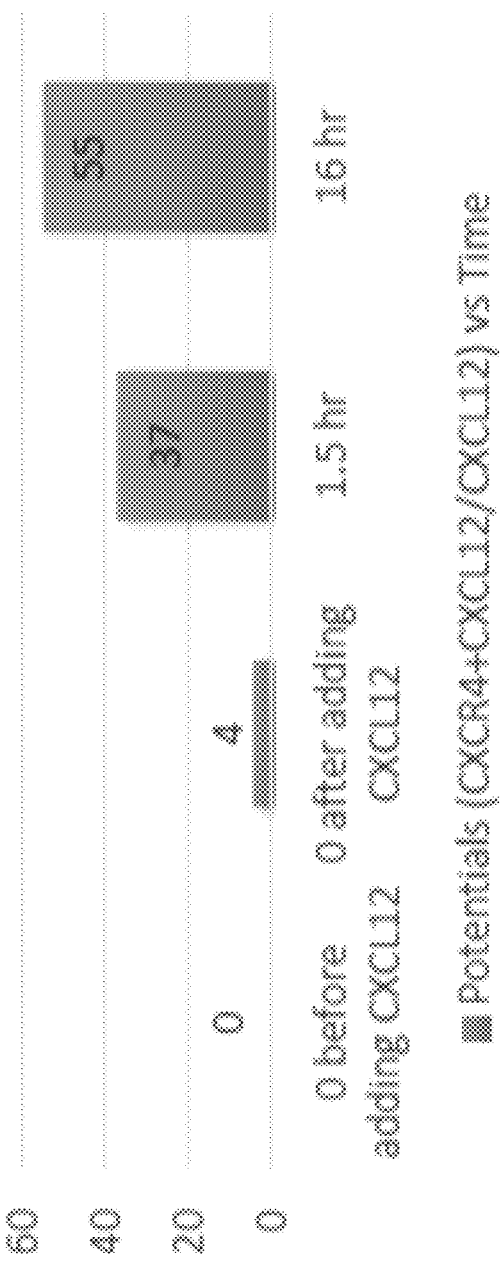
FIG. 24 is a graph showing the relative potential change of (CXCR4+CXCR12 versus CXCL12) as a function of time.
Figure 25B:
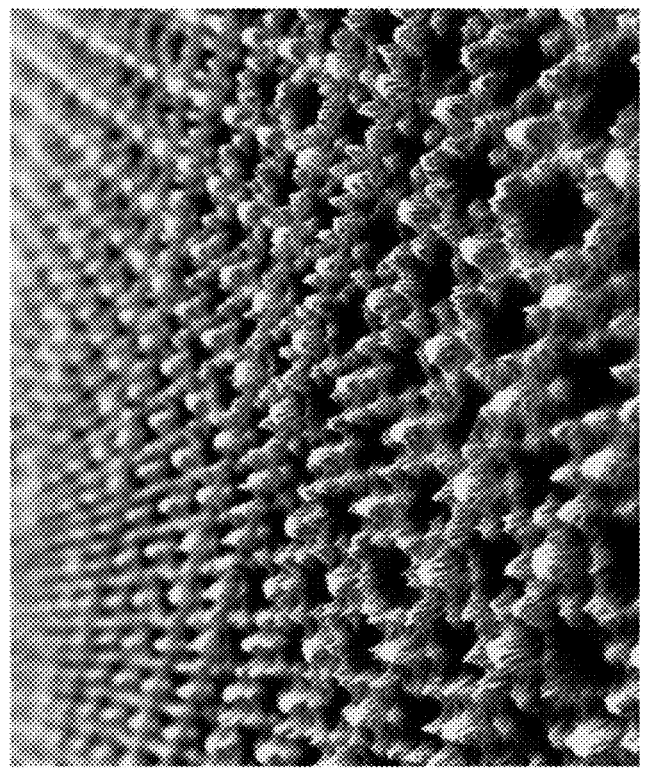
FIGS. 25A and 25B are high-resolution images of a S-layer protein.
Figure 25A:
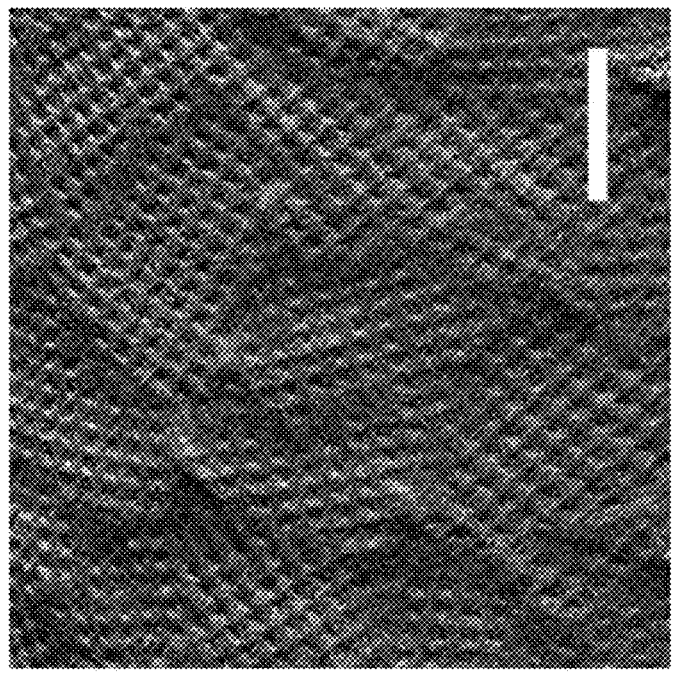

As described above, the self-assembling unit or the bioelectronic interface can be utilized in a biosensor to detect the binding of a potential ligand to the variant GPCR, wherein the binding of the potential ligand to the variant GPCR produces a detectable signal. In certain aspects, the biosensor is in the form of a chip or a bead. A non-limiting example of a chip is the CM5 chip (Biacore). The binding of the ligand to the variant GPCR can be detected, for example, by an electrical, electrochemical, dielectric or fluorescence signal. With respect to electrical signals, protein coated on an electronic surface can provide a slight current change during the binding process which can be measured. One challenge with respect to monitoring current is that the noise created by flow through of ligands would need to be eliminated. With respect to electrochemical signals, proteins exhibit static electrochemical potential/voltage that changes during ligand binding. The potential change is induced by a complex conformational change of state or change of chemical state for amino acids rather than a simple redox reaction. FIG. 24 shows the relative electrochemical potential change over time after adding CXCL12 to a substrate coated with CXCR4 versus solution with only CXCL12. With respect to polarization, GPCRs have a characteristic frequency response. The conformation change induced by ligand binding will change polarization of protein bonding that can provide a detectable change in RF frequency response. In addition, with respect to fluorescence spectroscopy, three amino acids, phenylalanine, tyrosine and tryptophan have intrinsic fluorescence. Fluorescence Lifetime Imaging (FLIM) produces an image based on the differences in the excited state from a fluorescent sample. The binding of the ligand can also be detected, for example, using surface plasmon resonance. The detectable signal can, for example, be a change in color, fluorescence, evanescence, surface plasmon resonance, electrical conductance or charge separation, ultraviolet, visible or infrared absorption, luminescence, chemiluminescence, electrochemiluminescence, fluorescence anisotropy, fluorescence intensity, fluorescence lifetime, fluorescence polarization, fluorescence energy transfer, molecular mass, electron spin resonance, nuclear magnetic resonance, hydrodynamic volume or radius, specific gravity, scintillation, field effect resistance, electrical impedance, acoustic impedance, quantum evanescence, resonant scattering, fluorescent quenching, fluorescence correlation spectroscopy, acoustic load, acoustic shear wave velocity, binding force, and interfacial stress.

The invention will be better understood in connection with the following example, which is intended as an illustration only and not limiting of the scope of the invention. Various changes and modifications to the disclosed embodiments will be apparent to those skilled in the art and such changes and may be made without departing from the spirit of the invention and the scope of the appended claims.

EXAMPLES

Example 1

Recombinant S-Layer Potein SbpA31-1068ZZ Bnds CXCR4QTY-Fc Materials and Mthods 2.1 Production of S-Layer Protein The chimeric gene encoding a C-terminally-truncated form of the S-layer protein SbpA from *Lysinibacillus sphaericus* CCM 2177 and two copies of the Fc-binding Z-domain was constructed, cloned, and heterologously expressed in Escherichia coli HMS174(DE3) as described in [A7] [A19]. The recombinant S-layer protein was over-expressed in *E. coli* and accumulated in inclusion body like structures which were stored after a downstream processing including a homogenization step at −20° C. [A20] [A16].

2.2 Production of a Monomeric S-Layer Protein Solution

The starting point for the production of a monomeric protein solution of the S-layer fusion protein $rSbpA_{31-1068}ZZ$ which recrystallization properties can be started with the addition of $CaCl_2$ ions were inclusion body extracts purified by gel chromatography as described previously [20]. Briefly, 5M GHC1 (Gerbu Nr. 1057; in 50 mM Tris/HCl, pH 7.2) was used to dissolve/denature the fully washed inclusion bodies. The retrieved protein solution was centrifuged at 14000 rpm (20,000 g) for 20 min to remove precipitations. The supernatant was filtered using a 0.2 μm syringe filter to remove potential aggregates and subsequently applied to a Superdex 200 column in order to purify the sample. After the chromatographic run the pooled fraction containing the S-layer protein was dialysed (membrane Biomol cut-off: 12-16 kD; pore size 25 A) against 3 L reverse osmosis (RO) water (water was changed at 30, 60 and 90 minutes and then dialyzed overnight at 4° C.). After the dialyses step the protein solution was filtrated through a 0.2 μm syringe filter. To determine the protein concentration of the protein solution UV measurements were performed at 280 nm using a spectrometer and a quartz cuvette. The protein concentration was adjusted to 1mg/ml using ice-cold Milli-Q water using the absorbance coefficient for rSbpA$_{31-1068}$ZZ (absorbance at 280 nm×1,6529=concentration in mg/ml). The so obtained monomeric protein solution was quality controlled to confirm the recrystallization properties onto solid surfaces using AFM (=atomic force microscopy) as described previously [21] (FIG. 1A). For further use the protein solution was stored at 4° C. for a maximum of 2 weeks. For recrystallization of rSbpA$_{31-1068}$ZZ onto solid substrates the monomeric protein solution was diluted with crystallization buffer containing 0.1M CaCl$_2$ to a final concentration of 100 μg/ml and applied to the substrates overnight.

2.3 Quartz Crystal Microbalance with Dissipation (QCM-D) Measurements

Prior to their use in the experiments, Silicon dioxide coated quartz sensors were sonicated in 2% (w/w) SDS solution for 20 minutes and rinsed with ultrapure water and ethanol. The crystals were dried under N2 stream, treated with UV/Ozone for 30 minutes and left overnight under saturated atmosphere of 1H, 1H, 2H, 2H-perfluorodecyl-trichlorosilane in a vacuum chamber, to ensure their hydrophobicity. Afterwards, silanized sensors were sonicated in ultrapure water and ethanol and finally mounted into the QCM-D chamber. Experiments were performed at 25° C. Real time variations of Frequency ($\Delta f$) and dissipation ($\Delta D$) parameters were observed at several overtones (n=3, 5, 7 . . . 13) throughout the experiment. Injection of the S-layer proteins (50 pg/ml applied in recrystallization buffer 10 mM CaCl$_2$ in 5 mM Tris, pH=9.0) were performed for 60 min allowing the formation of a closed monolayer. After washing with crystallization buffer CXCR4QTY-Fc was applied in 0.1 M glycine buffer pH 9.0 (50 μg/ml) onto the wtSbpA and the rSbpA$_{31-1068}$ZZ coated wafers at a constant flow rate for 55 minutes.

Incubation with CXCR4-Fc all washing steps as well as the addition of the different buffers, was performed by means of a peristaltic pump (Ismatec, Switzerland) operating at a flow rate of 0.3 ml/min. After a washing step a pH shift (0.1 M glycine buffer pH 3.0) was applied to elute the CXCR4QTY-Fc.

3. RESULTS AND SUMMARY

The S-layer fusion protein rSbpA31-1o68ZZ comprising two IgG-binding domains of Protein A can be used to functionalize various solid supports by the formation of a closed crystalline monolayer. The construction principle of this fusion protein result in a binding of the S-layer proteins via their N-terminus leaving the C terminal fused Fc binding moieties exposed.

Figure 4:
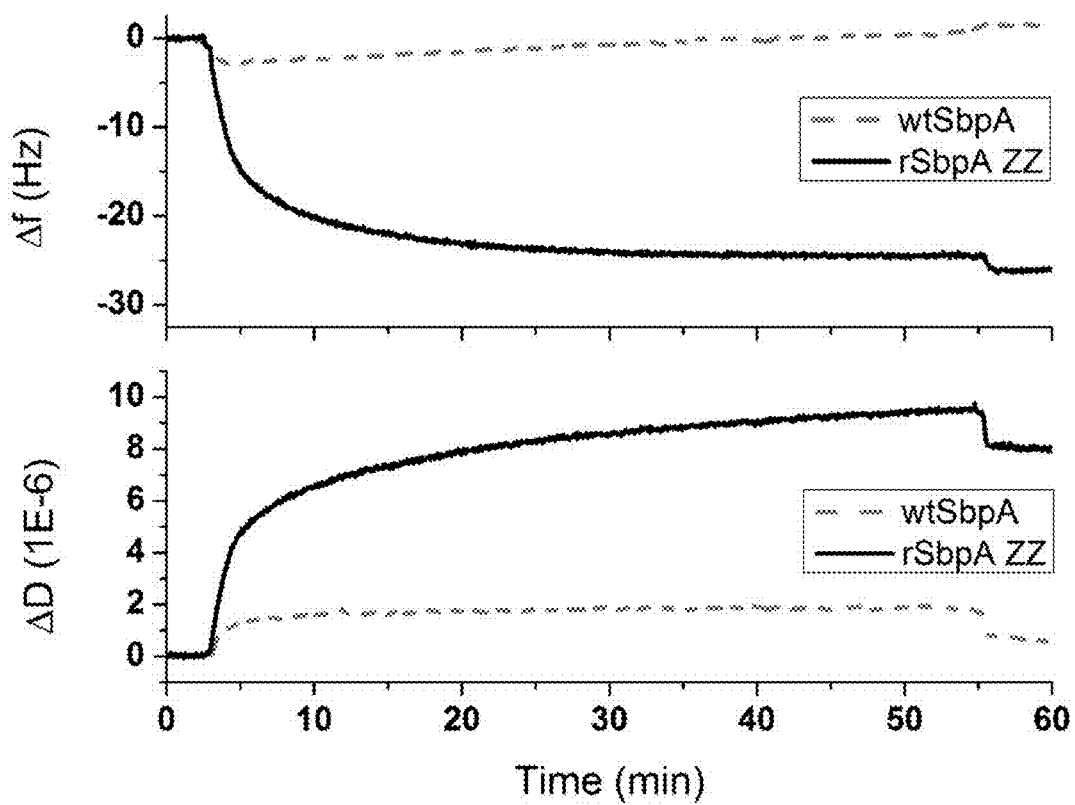
FIG. 4 is a graph of real-time monitoring of CXCR4QTY-Fc binding to rSbpA$_{31-1068}$ZZ (recombinant) and wtSbpA (wild type) coated hydrophobic silicon QCM-D chips as recorded for frequency (top) and dissipation (bottom). CXCR4QTY-Fc was applied in 0.1M glycine buffer (50 µg/ml); pH 9.0) at a constant flow rate. A decrease in frequency indicating increased mass adsorption and therefore binding could only be detected for the rSbpA$_{31-1068}$ZZ coated wafers. No binding could be seen with the wtSbpA (negative control) coated wafers confirming the specific binding of CXCR4QTY-Fc to the IgG binding moiety of rSbpA$_{31-1068}$ZZ. Within 20 min binding of CXCR4QTY-Fc was almost complete and no loss of proteins, either rSbpA$_{31-1068}$ZZ or CXCR4QTY-Fc could be observed until the incubation was ended after 55 min.
Figure 5:
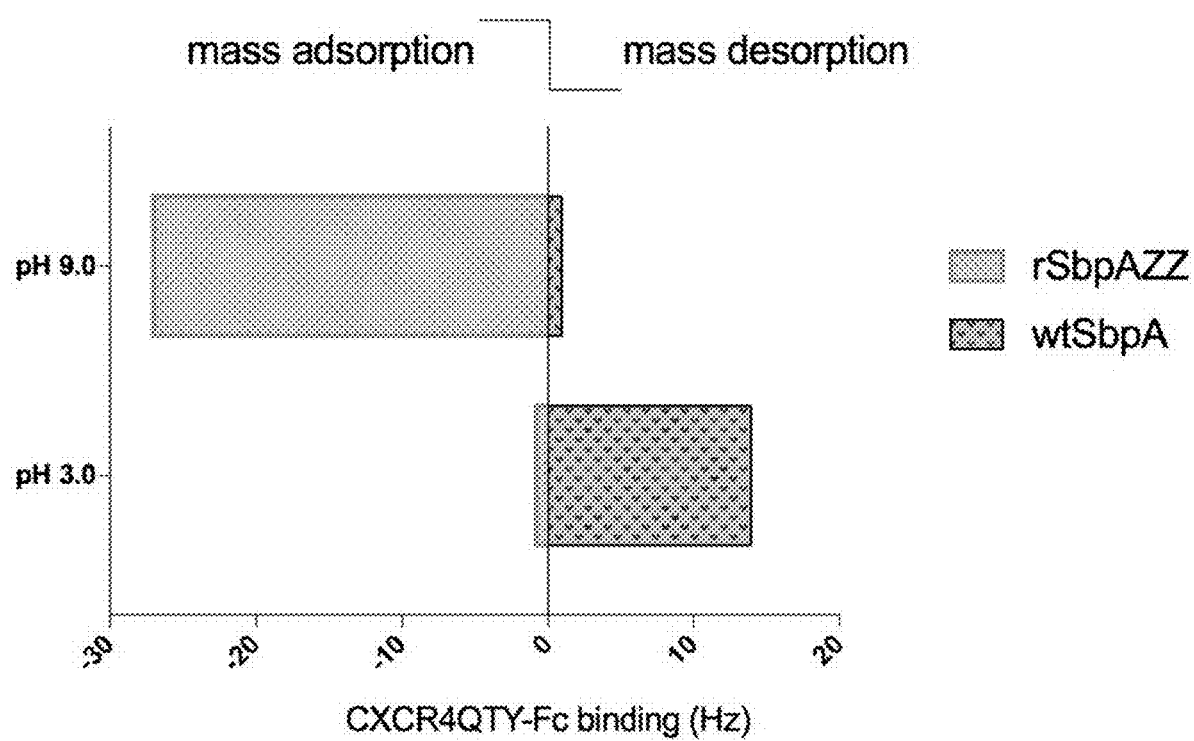
FIG. 5 shows the binding of CXCR4QTY-Fc at basic and elution at acidic pH from S-layer coated silicon wafers obtained with QCMD measurements. Graph showing adsorption of CXCR4QTY-Fc at basic pH (pH 9.0) to and desorption/elution at acidic pH (pH=3.0) from rSbpA$_{31-1068}$ZZ coated silicon wafers. As negative control, wtSbpA coated chips with no binding region for Fc fragments were used. CXCR4QTY-Fc was applied at 50 µg/ml glycine buffer pH 9.0. Here, CXCR4QTY-Fc binds only to the rSbpA$_{31-1068}$ZZ coated solid phase (decrease in frequency), not to the wtSbpA coated ones. After washing the bound CXCR4QTY-Fc could be completely eluted by applying a pH shift to pH 3.0.

Here, the potential of recombinant S-layer protein rSbpA$_{31-1068}$ZZ to bind CXCR4QTY-Fc was investigated. Real-time monitoring of CXCR4QTY-Fc binding to rSbpA$_{31-1068}$ZZ and wtSbpA coated hydrophobic silicon wafers were investigated with QCM-D. After coating QCM-D chips with rSbpA$_{31-1068}$ZZ (and wtSbpA as blank) CXCR4QTY-FC was applied in 0.1M glycine buffer (50 μg/ml); pH 9.0) at a constant flow rate. A decrease in frequency indicating increased mass adsorption and therefore binding of the CXCR4QTY-FC was observed only to the rSbpA$_{31-1068}$ZZ coated wafers (FIG. 4). No binding could be seen to the wtSbpA (negative control) coated ones confirming the specific binding of CXCR4QTY-Fc to the IgG binding moiety of rSbpA$_{31-1068}$ZZ. Within 20 min incubation with CXCR4QTY-Fc binding was almost complete and no loss of proteins, either rSbpA$_{31-1068}$ZZ or CXCR4QTY-Fc could be observed until the incubation was ended after 55 min. By applying a pH shift down to pH 3.0 (0.1M glycine buffer pH 3.0) a loss of mass down to the starting level could be observed indicating a pH dependent binding and eluting behavior of the rSbpA$_{31-1068}$ZZ coated Si wafers confirming the specific intrinsic binding of the CXCR4QTY-Fc via the Fc part to recrystallized rSbpA$_{31-1068}$ZZ (FIG. 5).

REFERENCE LIST A

1. Sleytr, U. B. & Glauert, A. M. (1975) Analysis of regular arrays of subunits on bacterial surfaces: evidence for a dynamic process of assembly, *J Ultrastruct Res.* 50, 103-116.
2. Sleytr, U. B., Schuster, B., Egelseer, E. M. & Pum, D. (2014) S-layers: principles and applications, *FEMS Microbiol Rev.* 38, 823-64.
3. Sleytr, U. B., Huber, C., Ilk, N., Pum, D., Schuster, B. & Egelseer, E. M. (2007) S-Layers as a tool kit for nanobiotechnological applications, *FEMS Microbiol Lett.* 267, 131-144.
4. Sleytr, U. B., Egelseer, E. M., Ilk, N., Pum, D. & Schuster, B. (2007) S-layers as a Basic Building Block in a Molecular Construction Kit, *FEBS J.* 274, 323-334.
5. Moll, D., Huber, C., Schlegel, B., Pum, D., Sleytr, U. B. & Sara, M. (2002) S-layer-streptavidin fusion proteins as template for nanopatterned molecular arrays, *Proc Natl Acad Sci USA.* 99, 14646-51.
6. Huber, C., Egelseer, E. M., Ilk, N., Sleytr, U. B. & Sara, M. (2006) S-layer-streptavidin fusion proteins and S-layer-specific heteropolysaccharides as part of a biomolecular construction kit for application in nanobiotechnology, *Microelectron Eng.* 83, 1589-1593.
7. Völlenkle, C., Weigert, S., Ilk, N., Egelseer, E., Weber, V., Loth, F., Falkenhagen, D., Sleytr, U. B. & Sára, M. (2004) Construction of a functional S-layer fusion protein comprising an immunoglobulin G-binding domain for development of specific adsorbents for extracorporeal blood purification, *Appl Environ Microbiol.* 70, 1514-21.
8. Breitwieser, A., Egelseer, E. M., Moll, D., Ilk, N., Hotzy, C., Bohle, B., Ebner, C., Sleytr, U. B. & Sára, M. (2002) A recombinant bacterial cell surface (S-layer)-major birch pollen allergen-fusion protein (rSbsC/Bet v1) maintains the ability to self-assemble into regularly structured monomolecular lattices and the functionality of the allergen, *Protein Eng.* 15, 243-9.
9. Sleytr, U. B. & Beveridge, T. J. (1999) Bacterial S-layers, *Trends Microbiol.* 7, 253-60.
10. Sleytr, U. B., Sara, M., Pum, D. & Schuster, B. (2005) Crystalline bacterial cell surface layers (S-layers): A versatile self-assembly system in *Supramolecular Polymers* (Ciferri, A., ed) pp. 583-612, Boca Raton.
11. Sára, M., Pum, D., Huber, C., Ilk, N., Pleschberger, M. & Sleytr, U. B. (2006) Nanoscale patterning of S-layer proteins as a natural self-assembly system in *Biological* and *Pharmaceutical Nanomaterials Nanotechnologies for the Life Sciences* (Kumar, C., ed) pp. 219-252, Wiley-VCH, Weinheim, Germany.
12. Pum, D. & Sleytr, U. B. (1995) Monomolecular reassembly of a crystalline bacterial cell surface layer (S layer) on untreated and modified silicon surfaces, *Supramol Sci.* 2, 193-197.
13. Picher, M. M., Kupcu, S., Huang, C. J., Dostalek, J., Pum, D., Sleytr, U. B. & Ertl, P. (2013) Nanobiotechnology advanced antifouling surfaces for the continuous electrochemical monitoring of glucose in whole blood using a lab-on-a-chip, *Lab Chip.* 13, 1780-9.
14. Rothbauer, M., Kupcu, S., Sticker, D., Sleytr, U. B. & Ertl, P. (2013) Exploitation of S-layer anisotropy: pH-dependent nanolayer orientation for cellular micropatterning, *ACS Nano.* 7, 8020-30.
15. Sára, M. & Sleytr, U. B. (1987) Production and characteristics of ultrafiltration membranes with uniform pores from two-dimensional arrays of proteins, *J Membr Sci.* 33, 27-49.
16. Ilk, N., Völlenkle, C., Egelseer, E. M., Breitwieser, A., Sleytr, U. B. & Sára, M. (2002) Molecular characterization of the S-layer gene, sbpA, of *Bacillus sphaericus* CCM 2177 and production of a functional S-layer fusion protein with the ability to recrystallize in a defined orientation while presenting the fused allergen, *Appl Environ Microbiol.* 68, 3251-60.
17. Ilk, N., Egelseer, E. M. & Sleytr, U. B. (2011) S-layer fusion proteins—construction principles and applications, *Curr Opin Biotechnol.* 22, 824-831.
18. Breitwieser, A., Pum, D., Toca-Herrera, J.L. Sleytr, U.B (2016) Magnetic beads functionalized with recombinant S-layer protein exhibit high human IgG-binding and antifouling properties, *Current Topics in Peptide & Protein Research.* 17, 45-55.
19. Huber, C., J. Liu, E. M. Egelseer, D. Moll, W. Knoll, U. B. Sleytr & Sára., M. (2006) Heterotetramers formed by an S-layer-streptavidin fusion protein and core-streptavidin as nanoarrayed template for biochip development., *Small.* 2, 142-150.
20. Ucisik, M. H., Kupcu, S., Breitwieser, A., Gelbmann, N., Schuster, B. & Sleytr, U. B. (2015) S-layer fusion protein as a tool functionalizing emulsomes and CurcuEmulsomes for antibody binding and targeting, *Colloids Surf B Biointerfaces.* 128, 132-9.
21. Gyorvary, E. S., Stein, O., Pum, D. & Sleytr, U. B. (2003) Self-assembly and recrystallization of bacterial S-layer proteins at silicon supports imaged in real time by atomic force microscopy, *J. Microsc.* 212, 300-6.

Example 2

The QTY Code: A Tool for Engineering Detergent-Free Chemokine Receptors CCR5, CXCR4, CCR10 and CXCR7 that Retain Ligand-Binding Activities Structure and function studies of membrane proteins, particularly G protein-coupled receptors (GPCRs) and multiple segment transmembrane proteins, require detergents. Without detergents these integral membrane proteins aggregate and are nearly impossible to analyze. We have devised a useful tool, the QTY Code, for engineering hydrophobic domains to become detergent-free, namely water-soluble, without significantly altering protein structure and function. Here we report using the QTY Code (glutamine, threonine and tyrosine) to systematically replace the hydrophobic amino acids leucine, valine, isoleucine and phenylalanine in the four chemokine receptors CCR5, CXCR4, CCR10 and CXCR7. By introducing ~19%-29% systematic QTY changes in these receptors (~47% to ~58% in the transmembrane helices), we were able to engineer receptors that become water-soluble in the absence of detergents. Using the yeast 2-hybrid system, we confirmed that variants with QTY changes still retain their ligand-binding function. The detergent-free variants also retain their stable α-helical structures (Tm 52.7° C. for CCR5QTY, Tm 63.5° C. for CXCR4QTY, Tm 54.8° C. for CCR10QTY and Tm 52.3° C. for CXCR7QTY). They bind their natural chemokine ligands in buffer: CCL5 KD ~34 nM for CCR5QTY, CXCL12 KD ~11 nM for CXCR4QTY, CCL27 KD ~3.1 nM for CCR10QTY, CCL28 KD ~9.3 nM for CCR10QTY, and CXCL11 KD ~16 nM for CXCR7QTY and CXCL12 KD ~2.2 nM for CXCR7QTY. Additionally they do not bind to human insulin used as a negative control. CCR5QTY, CXCR4QTY and CXCR7QTY also bind to HIV coat proteins gp41-120 with affinities of ~3 nM ~117 nM and ~1.2 nM, respectively. These engineered receptors also bind their ligands in 50% human serum with 2-4 times lower affinities. Our results suggest that despite the significant number of QTY changes, these detergent-free variants still maintain their stable structures and ligand-binding activities. Our simple QTY Code is a useful tool and has implications for engineering water-soluble variants of previously water-insoluble and perhaps aggregated proteins including amyloids.

Introduction

The structure and function of membrane proteins, particularly G protein-coupled receptors (GPCRs), are notoriously difficult to study[1-2]. In order to solubilize and stabilize membrane proteins outside of cellular lipid membranes, laborious, time-consuming and costly detergent optimizations are required. Recently, various methods of solubilizing membrane proteins with non-traditional detergents have been developed[3-4]. A few methods without detergents or lipid re-constitution have also been reported. For example, a method called SIMPLEx involves directly fusing a membrane protein to the C-terminus of a truncated apolipoprotein A-1[5]. This truncated protein serves as a shield that prevents direct exposure of the membrane protein to water[5]. However, the membrane proteins need to remain with the shields for all subsequent uses. In order to accelerate membrane protein studies, additional simple and robust methods are needed.

Computer calculations have been used to make specific changes in the transmembrane segments of 3 membrane proteins to make them water-soluble[6-10]. However, these amino acid substitutions are not systematic; there are no apparent rules or codes to follow (Supplementary Table S1). For example, Slovic et al made many changes in the transmembrane helices of phospholamban (a designed 31-residue synthetic peptide) to render it water-soluble. However, there was no consistent pattern to the substitutions: F was replaced by Y at position 35, but by R at position 38. L was replaced by E at positions 39 and 43, by Q at position 42, and by K at position 52[6, 8]. A similar approach was used to make changes in the potassium channel KcsA[7]. Likewise, Perez-Aguilar et al and Zhao et al made changes in the Mu opioid receptor in a non-systematic manne[9-10]. Engineered water-soluble α-helical bundles or barrels with di-, tri-, tetra-, penta-, hexa-, or hepta- α-helices have also been reported[11-12]. Such designed α-helices fold correctly. Again, each of these was developed individually, one sequence at a time, without any apparent governing rule. In all of these examples, no obvious foundational rules govern the choice of amino acid substitutions[6-12]. Because of its simplicity and systematic nature, we hypothesize that the QTY Code is likely to be more widely applicable.

The α-helix is constructed from its polypeptide backbone with the side chains perpendicular to its axis. It can accommodate any of the amino acid side chains, but its stability depends on the context and nature of each side chain[13]. All 20 amino acids are found in α-helices in the right environment[14], although some amino acids have higher propensities to form α-helices than others[13]. Typical α-helices have characteristic traits: 100°, 1.5 Å per amino acid rise; 3.6 residues per 360°, 5.4 Å per α-helical turn[13-14].

There are 3 types of α-helical backbone structures that are nearly identical according to crystallography data[14]: 1) those comprised of mostly hydrophobic amino acids commonly found in transmembrane segments, as in GPCRs; 2) those comprised of both hydrophobic and hydrophilic amino acids, sometimes partitioned into two faces; and 3) those comprised of mostly hydrophilic amino acids, as in hemoglobin. Both hemoglobin and GPCRs are comprised of a high percentage of α-helices. Hemoglobin's structure is known to be comprised of ~80% α-helices[15] and it is one of the most water-soluble proteins, at ~30% (~300 mg/ml) in red blood cells[16]. However, without detergents GPCRs with 7 transmembrane (7TM) α-helices, are water-insoluble. We asked if we could convert water-insoluble α-helices (as in GPCRs) to water-soluble ones (as in hemoglobin) without significantly changing their structural properties or altering their surface charges.

Several amino acid structures share strikingly similar crystallographic electronic density maps (FIG. 6 and FIG. 7), but have very different chemical properties. For example, the density map of the hydrophobic leucine (L) is similar to the density maps of the hydrophilic asparagine (N) and glutamine (Q); the density map of the hydrophobic isoleucine (I) and valine (V) are similar to the density map of the hydrophilic threonine (T); and the density map of the hydrophobic phenylalanine (F) is similar to the density map of the hydrophilic tyrosine (Y). This similarity in density maps can lead to natural "amino acid confusion." For example, the valine (V) tRNA synthetase (ValRS)[17] mischarges threonine (T) and isoleucine (I) at a rate of one per 200-400[18-19].

This similarity in electron density maps forms the basis of the QTY Code reported here, which involves the following substitutions: L→Q, I & V→T, and F→Y (FIG. 7A). These residue substitutions are made in order to increase receptor water-solubility while minimally affecting structural properties. The side chains of L, V, I and F cannot form any hydrogen bonds with water, which renders them water-insoluble. On the other hand, Q can form 4 hydrogen bonds with 4 water molecules (2 as hydrogen donors and 2 as hydrogen acceptors). Likewise, the —OH groups of T and of Y can form 3 hydrogen bonds with 3 water molecules (2 H-acceptors and 1 H-donor) (FIG. 13). Because Q is water soluble, it is the choice to replace L. Furthermore, both L and Q have high tendencies to form α-helices and can stabilize the same structure[20]. Although N has similar properties to Q, it prefers turns and is involved in glycosylations in eukaryotes. Thus Q, but not N, was chosen to replace L. Similarly, because T and Y are water-soluble, they were chosen to replace I, V and F.

Although water also forms hydrogen bonds with aspartic acid (-), glutamic acid (-), lysine (+) and arginine (+), these residues introduce charges, thereby altering the surface property of proteins. They were thus not introduced in the QTY Code.

Chemokine receptors belong to members of the GPCR family. They are comprised of 7 transmembrane (7TM) α-helical segments, which in turn are comprised of large numbers of the hydrophobic residues L, I, V and F. These receptors are involved in a number of crucial cellular signaling events, including cancer metastasis and those that maintain health[21-23].

The QTY code was applied to the chemokine receptors CCR5, CXCR4, CCR10 and CXCR7. These receptors were chosen because they play critical roles in diseases, and because they have been well characterized. CCR5, CXCR4 and CXCR7 are co-receptors for HIV entry into T cells[29-30]. CCR5's natural ligand is the chemokines $CCL5_{26-91}$ (also called Rantes), and CXCR4 and CXCR7's natural ligand is $CXCL12_{24-88}$ (also called SDF1α[24-28]. Moreover, crystal structures of CCR5 and CXCR4 are available[31-32], allowing direct comparison with the QTY variants $CCR5^{QTY}$ and $CXCR4^{QTY}$ after those structures become available in future studies. CCR10 and CXCR7 currently have no crystal structures yet. Finally, human CCR5 and CXCR4 have polymorphisms with 37 and 16 natural amino acid mutations among their 352 amino acids, respectively, which may allow them to better tolerate systematic protein engineering.

A yeast 2-hybrid system[33-34] was used to verify in vivo experiments if the QTY variants are able to activate gene transcription in yeast cells where both receptor and ligand genes are expressed at the same time.

After the yeast 2-hybrid interaction tests, the QTY variant sequences were re-coded with codons for optimal expression in baculovirus insect SF9 cell or in *E. coli* for protein expression and affinity purification without detergents. The purified detergent-free forms of $CCR5^{QTY}$, $CXCR4^{QTY}$, $CCR10^{QTY}$ and $CXCR7^{QTY}$ were used for ligand-binding studies. In order to perform the ligand-binding studies in buffers and in human serum, surface-free Microscale Thermophoresis[36-44] was used.

Our results show that despite ~22% changes for $CCR5^{QTY}$, ~29% changes for $CXCR4^{QTY}$, ~19% changes for $CCR10^{QTY}$ and ~23% changes for $CXCR7^{QTY}$, the receptors maintain their overall structures. Moreover, they bind their respective ligands in buffer and in 50% human serum. $CCR5^{QTY}$, $CXCR4^{QTY}$, and $CXCR7^{QTY}$ also bind to HIV surface protein gp41-120 at affinities similar to those reported in the literature[24-29]. The receptors do not bind human insulin, which was used as a control.

Since we have not yet obtained high-resolution structures of the detergent-free variants, $CCR5^{QTY}$, $CXCR4^{QTY}$, $CCR10^{QTY}$ and $CXCR7^{QTY}$ were simulated in an explicit water environment using 3 different computer programs[45-48]. These simulated structures were directly compared with the known crystal structures of natural CCR5[31] and CXCR4[32]. The structural folds are very similar and can be superimposed, suggesting that the QTY variants retain a natural overall structure despite substantial sequence changes.

Results

CCR5, CXCR4, CCR10 and CXCR7 Bioinformatics

Figure 15:
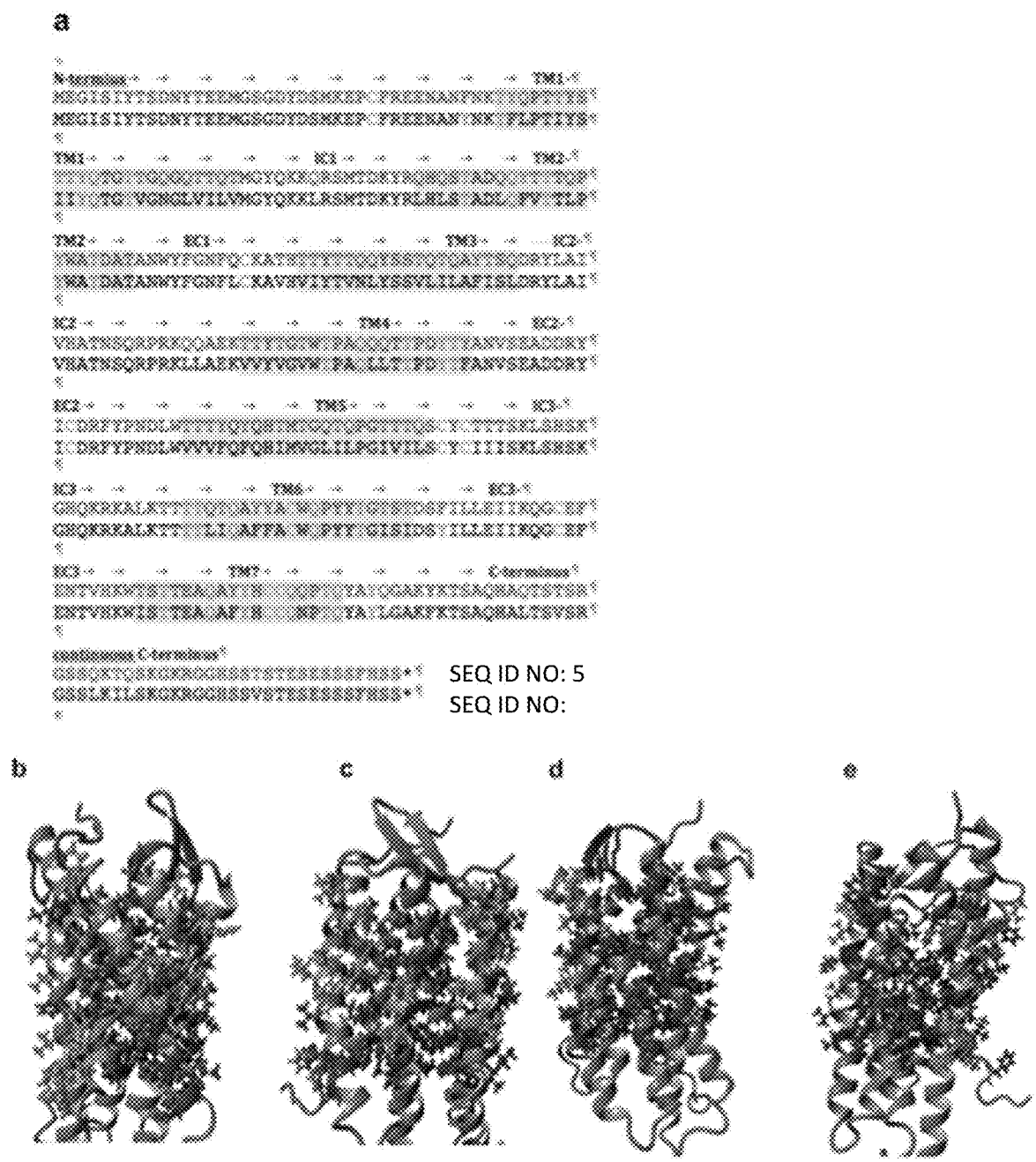
Figure 16A:
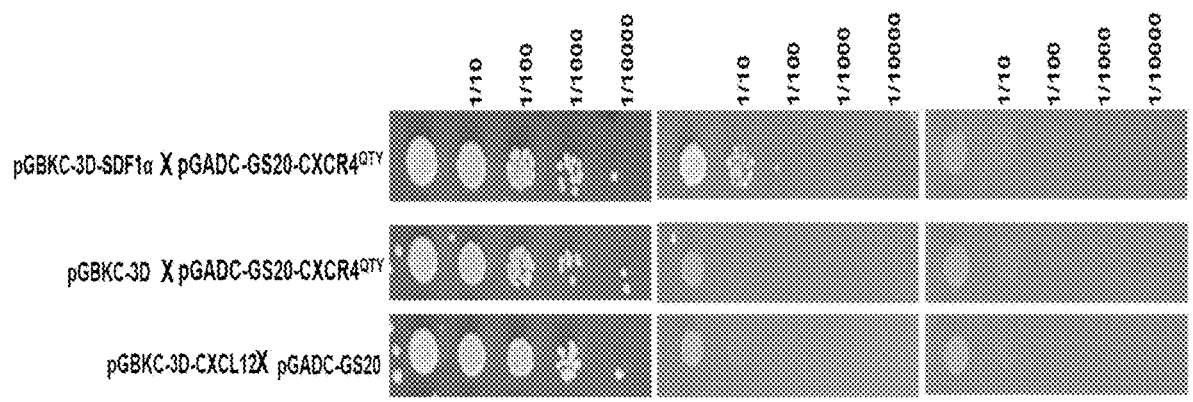
Figure 16B:
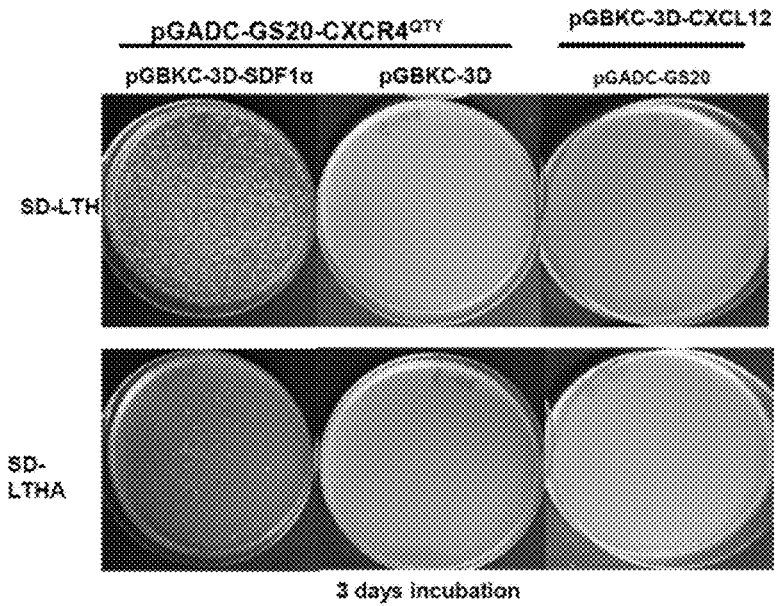
Figure 16C:
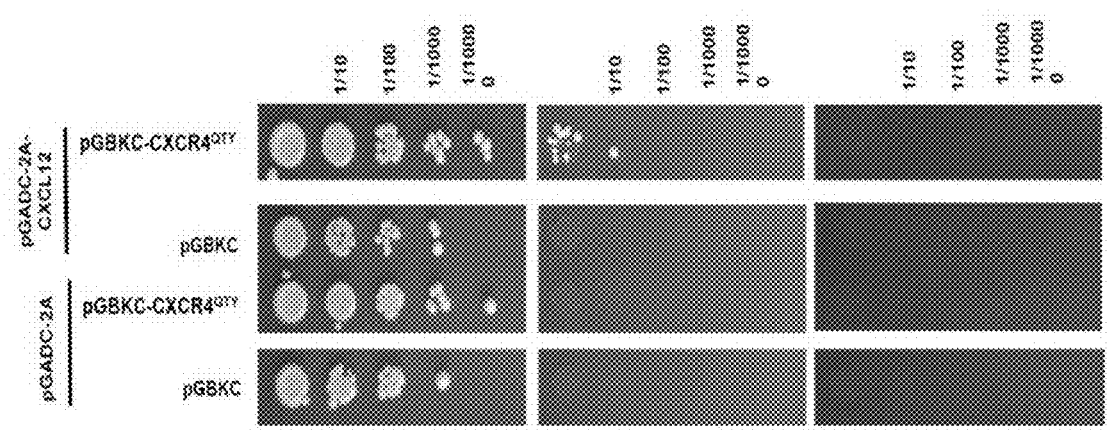
Figure 16D:
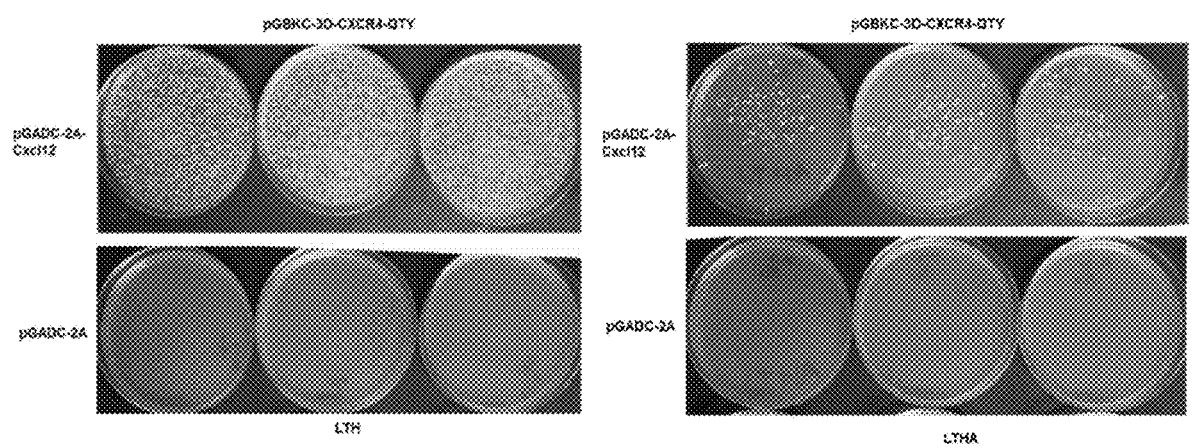

Alignments were performed for CCR5 vs $CCR5^{QTY}$, CXCR4 vs $CXCR4^{QTY}$, CCR10 vs $CCR10^{QTY}$, and CXCR7 vs $CXCR7^{QTY}$. FIG. 8 shows the transmembrane (TM) α-helical segments before and after applying the QTY Code. For example, natural CCR5 has 14 hydrophobic amino acids in TM1, 9 in TM2, 14 in TM3, 14 in TM4, 10 in TM5, 12 in TM6 and 4 in TM7 (total 77 among 352 amino acids, 21.88%). Likewise, CXCR4 has 16 hydrophobic amino acids in TM1, 12 in TM2, 13 in TM3, 12 in TM4, 14 in TM5, 11 in TM6 and 9 in TM7 (total 87 among 352 amino acids, 24.71%+16 amino acids from C-terminal and internal loops 4.54%). After applying the QTY Code, the hydrophobic amino acid numbers are significantly reduced (FIG. 8, FIG. 14, and FIG. 15). In spite of these changes, the location of the helical regions is predicted to remain the same. These substitutions render the seven-transmembrane α-helical segments water-soluble without detergents.

Yeast 2-Hybrid Verification

We used a yeast two-hybrid assay (FIG. 16) in order to study the interactions between QTY variants and their respective ligands. We used the yeast two-hybrid system as an in vivo assay to test QTY variants for ligand binding. If the variants interact with their respective ligands, the receptor-ligand pairs activate gene transcription, thus enabling yeast cell growth. The variants were further subjected to control assays to eliminate false positives.

In the yeast 2-hybrid experiments, in order to allow maximal ligand-receptor interactions in the Y2H fusion proteins, the ligands and receptors were cloned into custom-made Y2H bait and prey vectors. Yeast GAL4 activation and DNA binding domains are at the C-terminus of the fusion proteins, leaving both free receptor and chemokine N-termini. Only those variants that are folded properly in the intracellular milieu and transported into yeast nucleus are able to activate gene transcription of the Y2H reporters. Yeast cells harboring QTY variants not folding properly cannot activate gene transcription in nucleus, thus cells cannot grow.

For example, the interaction between the CXCR4$^{QTY}$ receptor and CXCL12 ligand was confirmed both when CXCR4$^{QTY}$ bait was paired with CXCL12 as the prey, and also when CXCL12 served as the bait and CXCR4$^{QTY}$ as the prey (FIG. 16). These results showed binding activity of the CXCR4$^{QTY}$ receptor with its natural ligand CXCL12 in the intracellular environment, where such ligand-receptor interactions normally do not occur. CXCR4$^{QTY}$ C-terminus was not included to avoid possible interference in this Y2H assay. After the Y2H test and mating, the C-terminal sequence was subsequently added back for making the full-length synthetic CXCR4$^{QTY}$ for gene expression and protein purification.

Protein Expression and Purification in SF9 Insect Cells and in *E. coli* Cells

After the variants were confirmed through the yeast mating tests, we re-synthesized the genes with organism-specified codons. We then expressed CCR5$^{QTY}$, CCR10$^{QTY}$ and CXCR7$^{QTY}$ in SF9 insect cells and CXCR4$^{QTY}$ in *E. coli* inclusion bodies. Each receptor carried a C-terminal His tag.

For each protein, a two-step purification strategy of affinity chromatography combined with size exclusion chromatography was applied. Since the amount of protein binding to the affinity chromatography resin was initially low, we screened for different additives to improve the purification yields. Among them, ammonium sulfate, 10 mM DTT and 0.5M L-Arginine were very important, but no detergents were needed at all. Purification in the presence of an additional 10 mM DTT resulted in a higher amount of purified protein since CCR5$^{QTY}$, CXCR4$^{QTY}$, CCR10$^{QTY}$ and CXCR7$^{QTY}$ have 12, 9, 10 and 14 cysteines, respectively. We also used a material based on a different chelator than nitrilotriacetic acid (NTA) with a higher stability against reduction. No detergents were used during purification or subsequent measurements.

The purified protein yields from insect SF9 cells were low and inadequate for structural analysis and other uses. In order to obtain large amount of protein for structural studies, CXCR4$^{QTY}$ was expressed in *E.coli* inclusion bodies at ~10 mg/liter. The protein was extensively washed and denatured in 6M Guanidine HCl. It was then re-refolded in a re-naturation buffer containing 0.5M L-Arginine, which is a key ingredient required for correct refolding. CXCR4$^{QTY}$ was then purified by His-tag purification and gel filtration. It should be noted that CCR5$^{QTY}$ and CXCR4$^{QTY}$ were independently purified twice for ligand-binding studies. The results were reproducible.

Ligand Binding Measurements

We used MicroScale Thermophoresis (MST)[36-44] to carry out ligand-binding measurements in both buffer and 50% human serum. Each sample was independently measured 3 times in duplicate (a total of 6 measurements) in order to obtain unambiguous ligand-binding results. These results suggest that the purified detergent-free forms of CCR5$^{QTY}$, CXCR4$^{QTY}$, CCR10$^{QTY}$ and CXCR7$^{QTY}$ retain their ligand-binding activities despite substantial QTY amino acid changes. We also measured binding to human insulin to rule out non-specific binding (Table 1, FIG. 9). Furthermore, since it is known that natural CCR5, CXCR4 and CXCR7 bind to HIV1 coat protein gp41-120, we also carried out binding measurements between CCR5$^{QTY}$, CXCR4$^{QTY}$ and CXCR7$^{QTY}$ with gp41-120 (Table 1 and FIG. 9*e*).

Figure 9A:
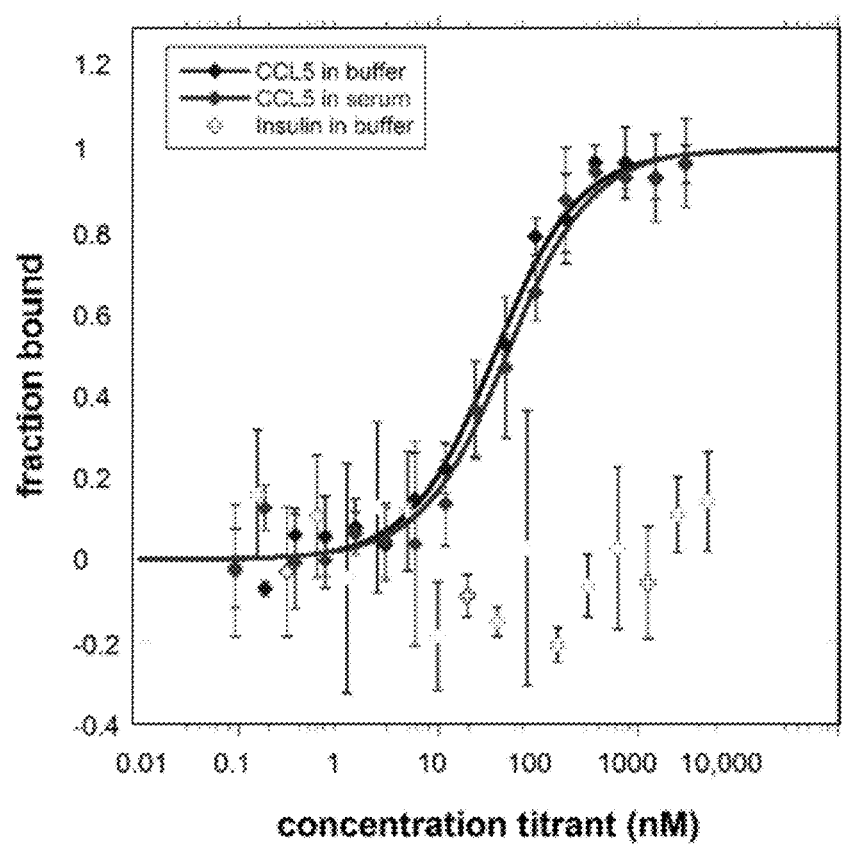
Figure 9B:
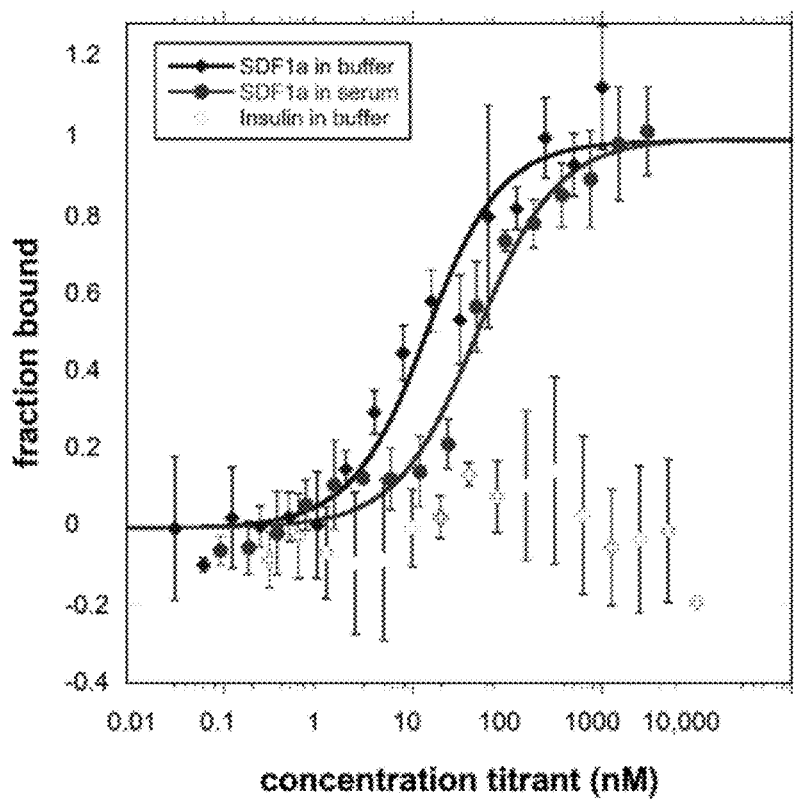
Figure 9C:
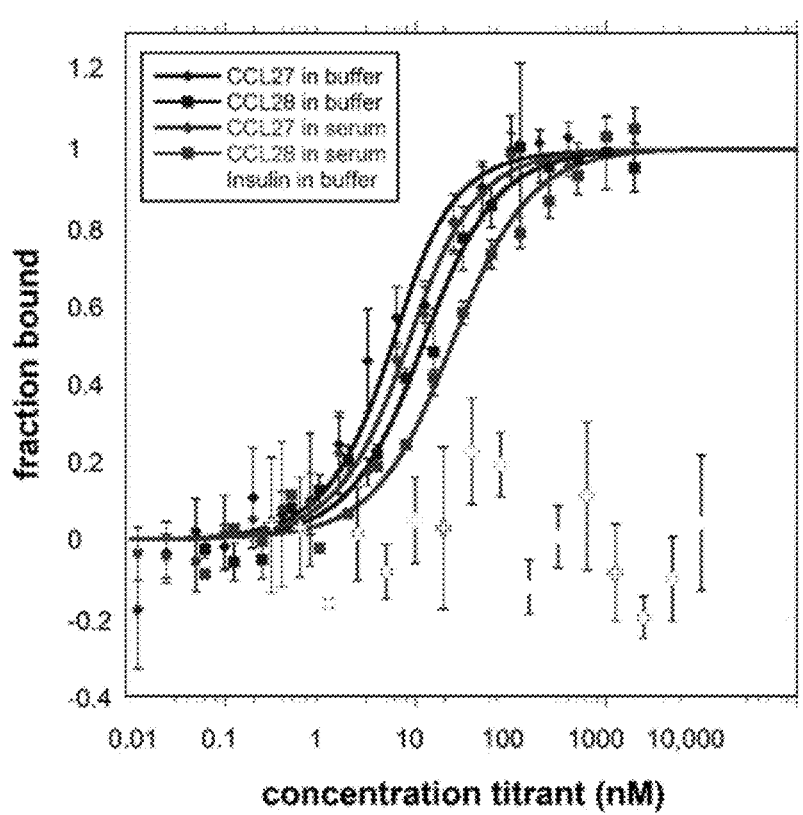
Figure 9D:
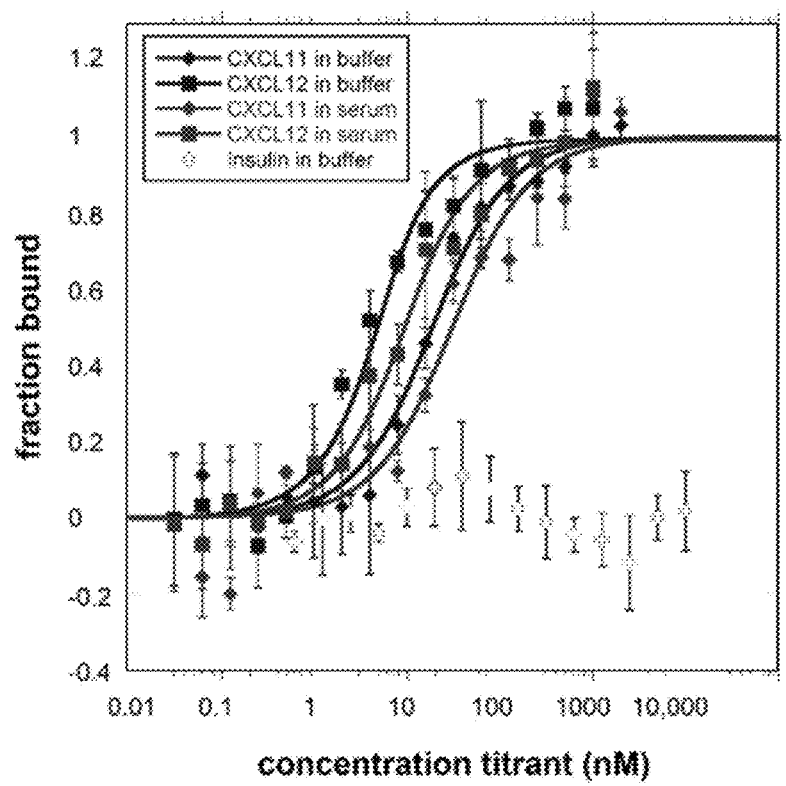
Figure 9E:
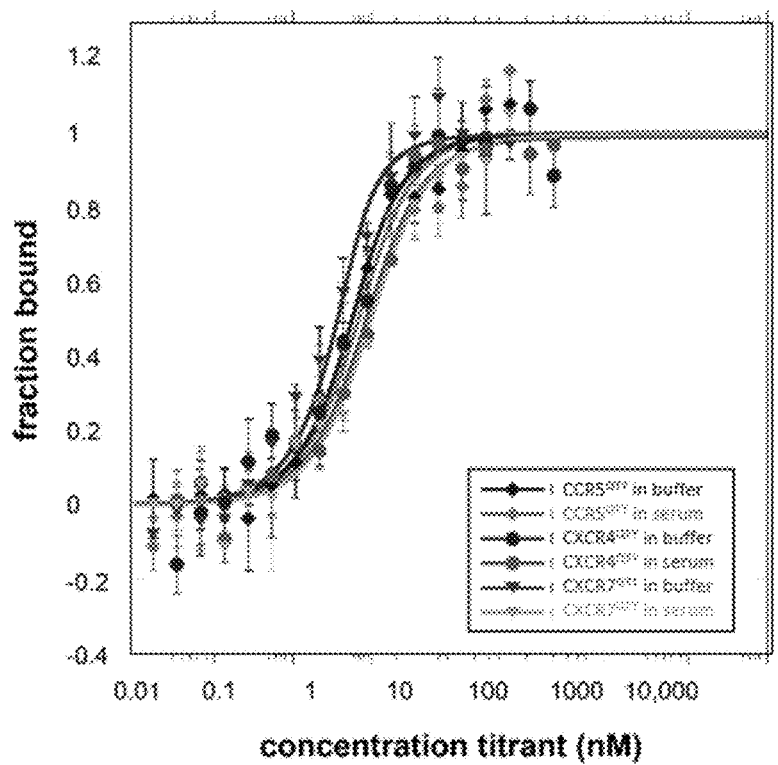
Figure 10A:
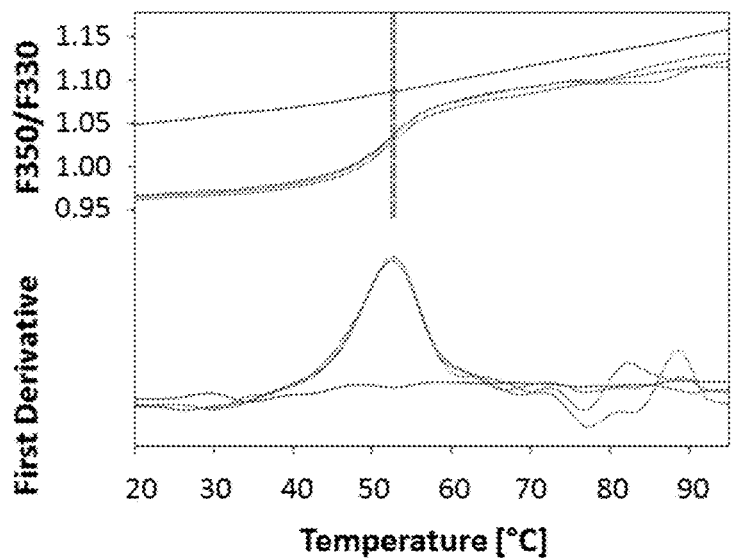
Figure 10B:
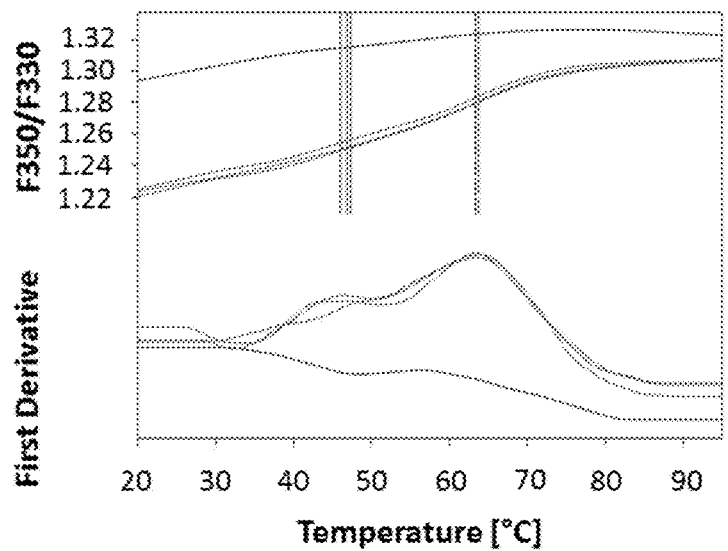
Figure 10C:
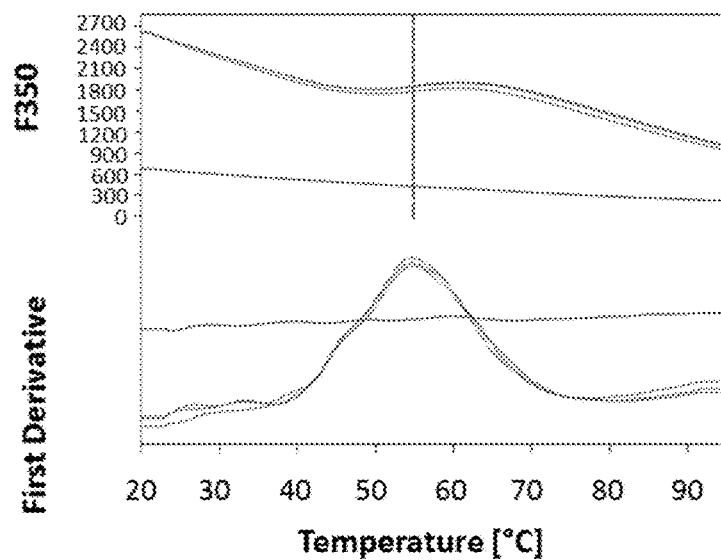
Figure 10D:
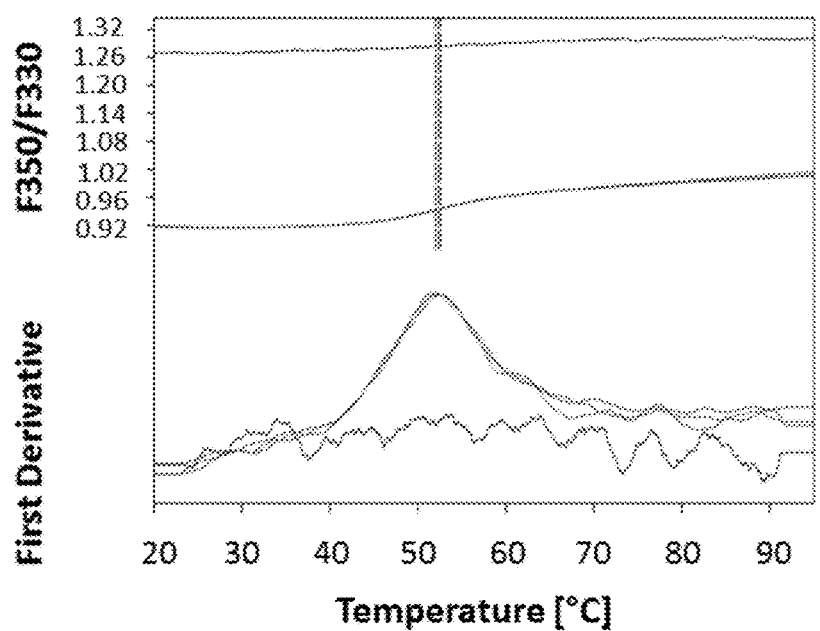

The binding affinities of the purified proteins to their respective ligands were determined using the MST Monolith NT.115 Pico instrument. Since the ligands CCL5$_{24-91}$, CXCL12$_{22-93}$, CCL27$_{25-112}$, CCL28$_{20-127}$ and gp41-120 contain tryptophan (W), the receptors used in the binding assays were fluorescently labeled. Constant concentrations of CCR5$^{QTY}$, CXCR4$^{QTY}$ CCR10$^{QTY}$ and CXCR7$^{QTY}$ were titrated against successive ligand dilutions in either buffer (1× PBS pH7.4, 5 mM DTT) or 50% human serum (Table 1, FIG. 9) and analyzed. The binding affinity of CCR5$^{QTY}$ to CCL5 was determined to be $K_D$ ~34 nM in buffer and ~46 nM in 50% human serum (FIG. 9*a*). The affinity of CXCR4$^{QTY}$ for CXCL12 was determined to be $K_D$ ~11 nM in buffer and $K_D$ ~45 nM in 50% human serum (FIG. 9*b*). The affinity of CCR10$^{QTY}$ for CCL27 was $K_D$ ~3.1 nM and for CCL28 was $K_D$ ~9.3 nM in buffer; and the affinity for CCL27 was ~5.6 nM, and the affinity for CCL28 was ~21 nM in 50% human serum (FIG. 9*c*). The affinity of CXCR7$^{QTY}$ for CXCL11 was $K_D$ ~16 nM, and for CXCL12 was $K_D$ ~2.2 nM in buffer (FIG. 9*e*); and the affinity for CXCL11 was $K_D$ ~28 nM, and the affinity for CXCL12 $K_D$ ~6.6 nM in 50% human serum. For gp41-120, the affinities for CCR5$^{QTY}$, CXCR4$^{QTY}$ and CXCR7$^{QTY}$ were ~3.1 nM, 117 nM and ~1.2 nM, respectively in buffer. In 50% human serum, the affinities were ~4.3 nM, ~185 nM and ~7 nM, respectively (FIG. 9E, Table 1).

In order to rule out the possibility of non-specific binding, we also measured the affinity of human insulin for CCR5$^{QTY}$, CXCR4$^{QTY}$, CCR10$^{QTY}$ and CXCR7$^{QTY}$. The reproducible measurements conclusively demonstrate that the detergent-free variants do not bind human insulin (FIGS. 9*c* and *d*), thus suggesting that these QTY variant receptors bind to their ligands with specificity.

Thermostability of CCR5$^{QTY}$, CXCR4$^{QTY}$, CCR10$^{QTY}$ and CXCR7$^{QTY}$

In order to determine the thermostability of the QTY variants, 3 independent nanoDSF measurements were carried out. The results show that CCR5$^{QTY}$, CXCR4$^{QTY}$, CCR10$^{QTY}$ and CXCR7$^{QTY}$ have average melting temperatures of Tm ~52.7° C., 63.5° C., 54.8° C. and 52.3° C., respectively (FIG. 10). Controls were carried out by heating the same proteins to 90° C. for 15 minutes before taking 3 independent measurements. The proteins were fully denatured and produced no measurable Tm (FIG. 10). These results suggest that despite significant QTY amino acids changes, the detergent-free CCR5$^{QTY}$, CXCR4$^{QTY}$, CCR10$^{QTY}$ and CXCR7$^{QTY}$ still remain relatively thermostable. It is likely that such thermal stabilities are not due to hydrophobic interactions, but are perhaps due to internal hydrogen bond network interactions as well as water molecule-bridged hydrogen bonds, similar to the water-bridged hydrogen bond interactions found in collagen structures.

Figure 17A:
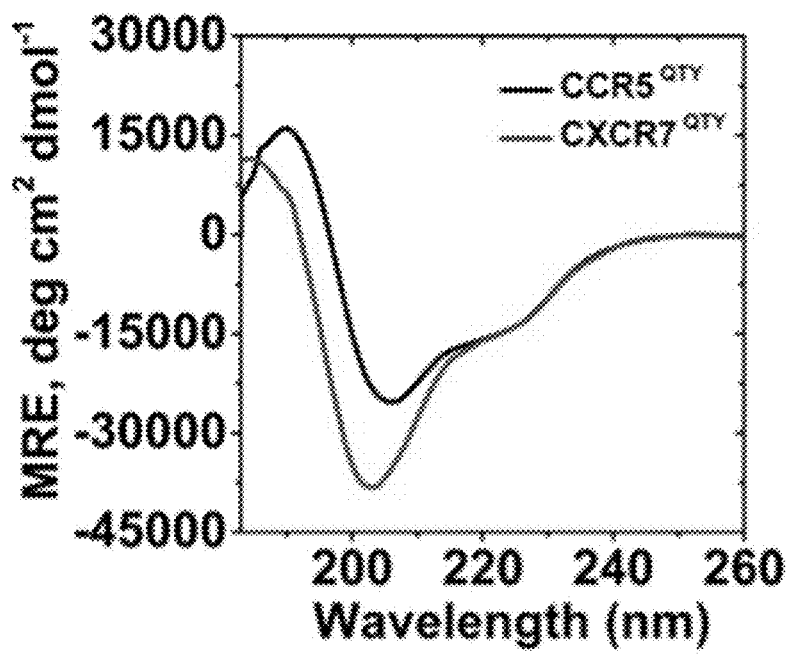
Figure 17B:
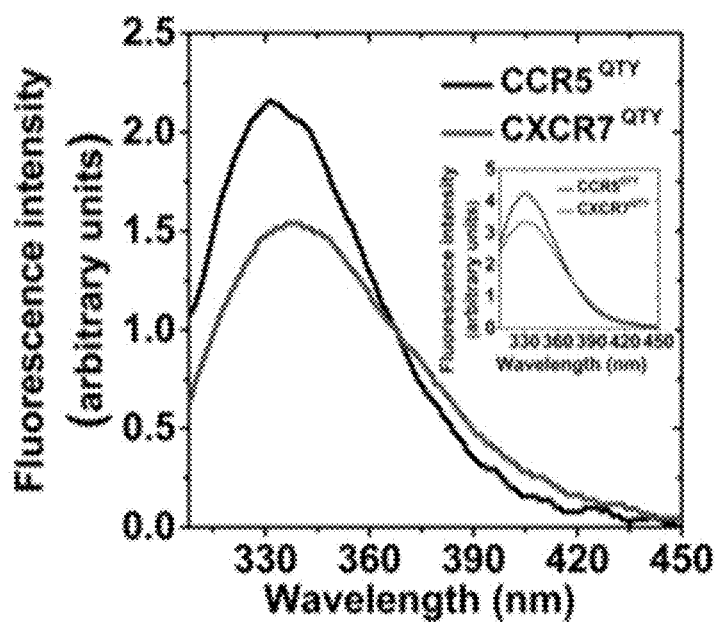
Figure 18:
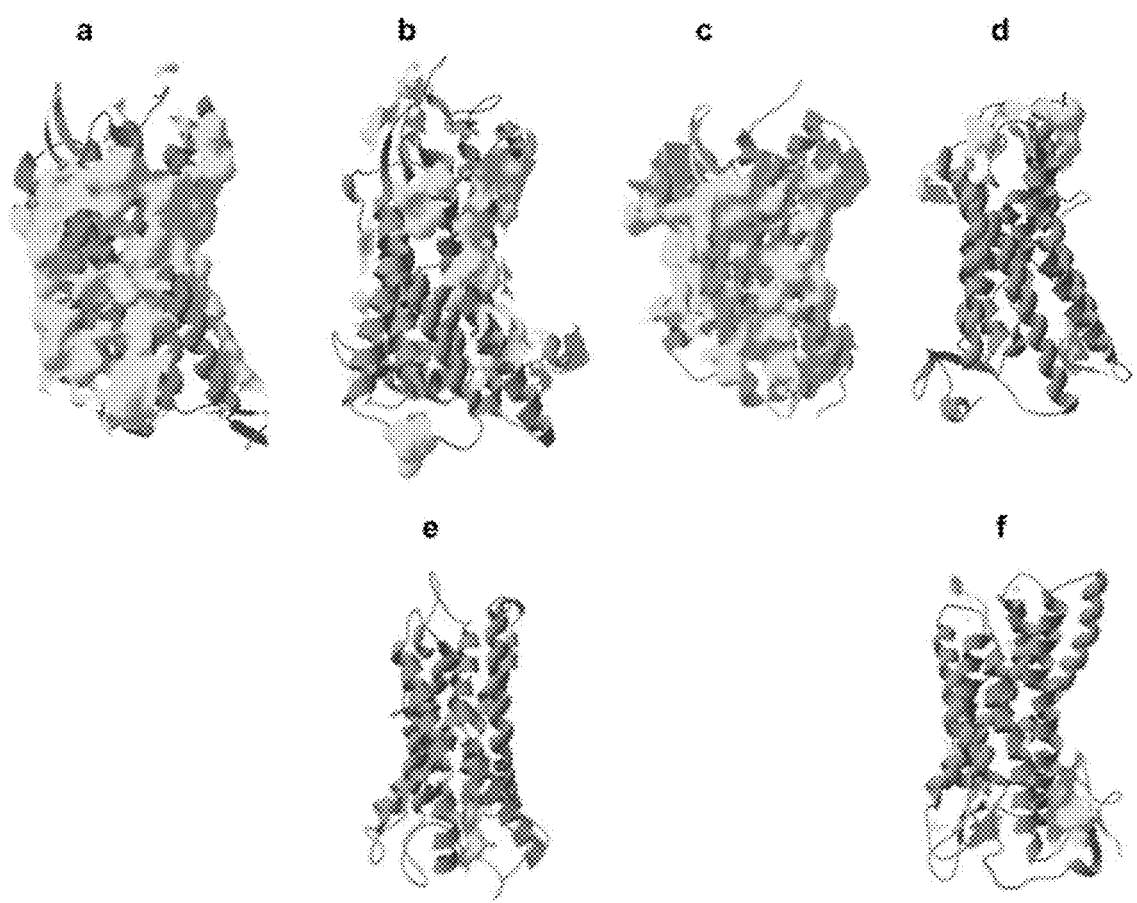
Figure 19:
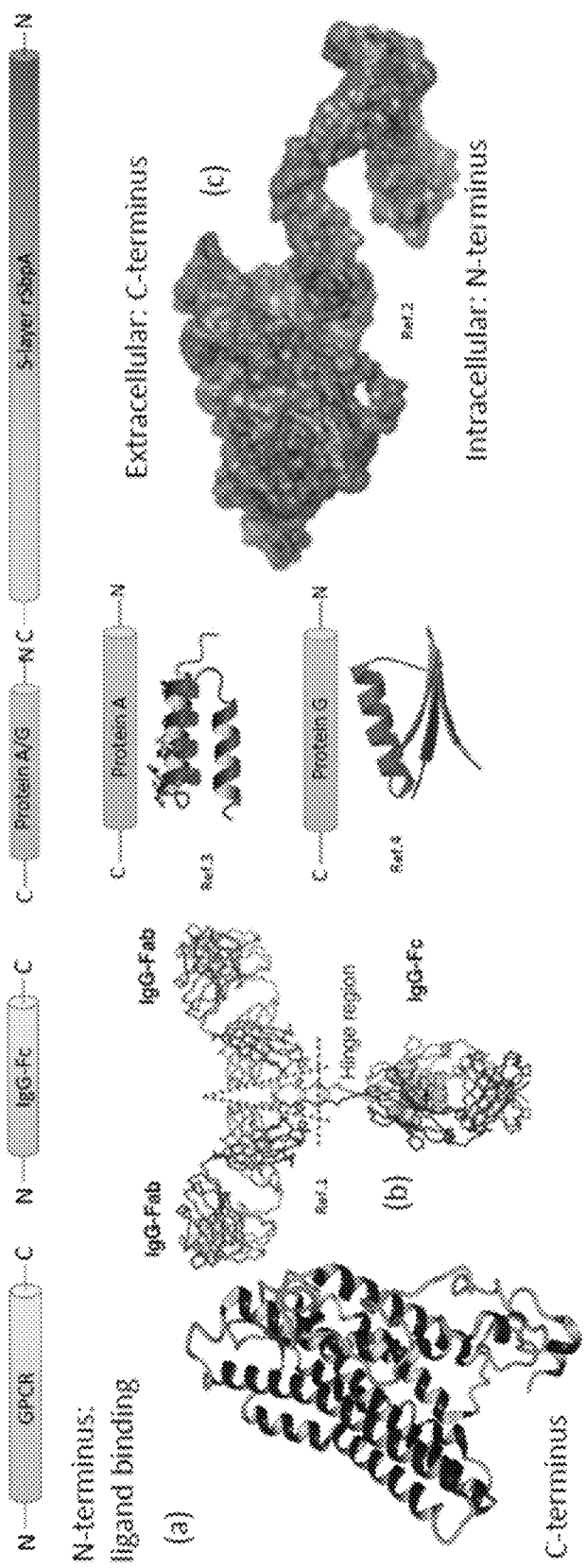
FIG. 19 is a drawing illustrating the elements of the GPCR variant fusion protein (GPCR-IgG Fc fusion) and the elements of the S-layer fusion protein (S-layer rSbpA-Protein A/G fusion) to be "installed" on the substrate.
Figure 20:
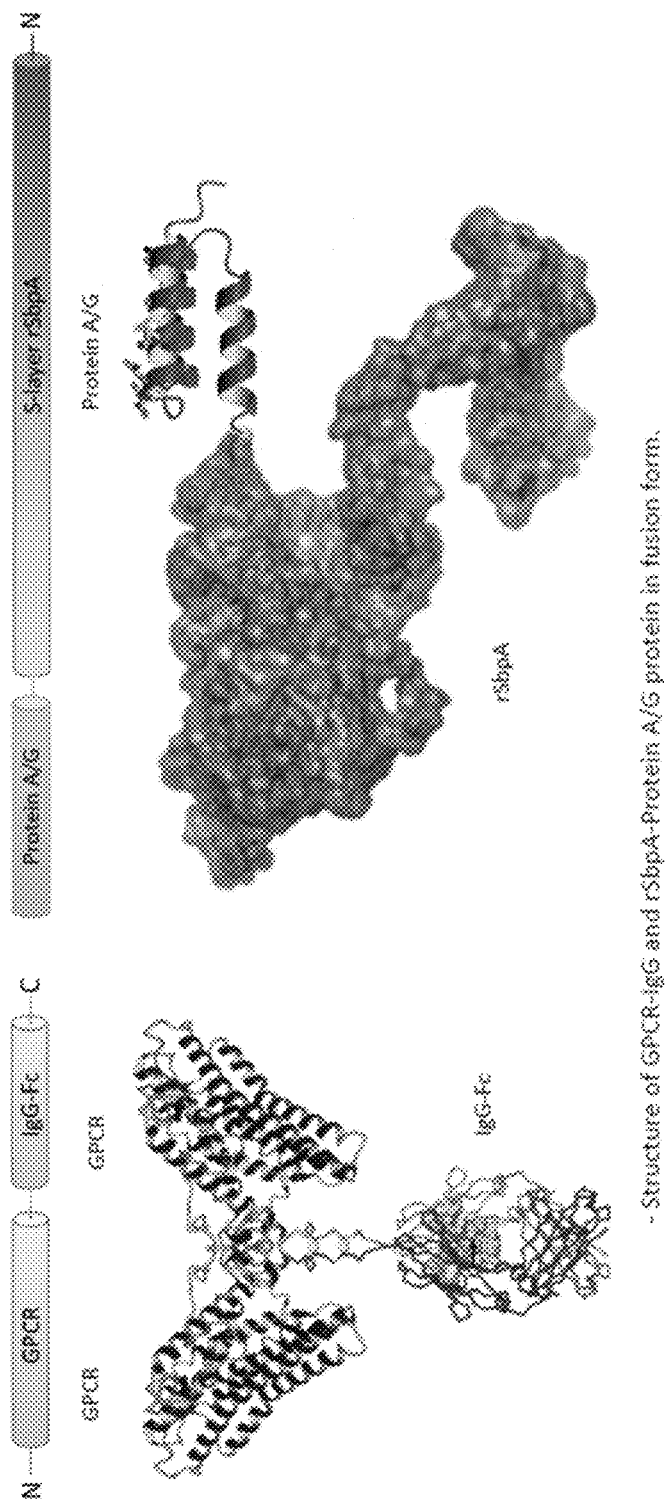
FIG. 20 is a drawing illustrating the two fusion proteins.

Circular Dichroism and Fluorescence Studies of Structures of QTY Variant Proteins The seven α-helical transmembrane segments of GPCRs can be studied using circular dichroism (CD), which detects a distinctive α-helical spectra. We used the purified CCR5$^{QTY}$ and CXCR7$^{QTY}$ in buffer containing 150 mM NaF, 5 mM DTT to carry out the study. Far UV spectra between 183 nm to 260 nm confirm the typical α-helical secondary structure of CCR5$^{QTY}$ and CXCR7$^{QTY}$. Furthermore, the α-helical content of CCR5$^{QTY}$ (~55%) and CXCR7$^{QTY}$ (~60%) are similar to the content in wild type CCR5 (59%)[20] and from secondary structural prediction of CXCR7 (64%) (FIG. 17 and Table 2).

The pure tryptophan fluorescence spectra with 295 nm excitation of CCR5$^{QTY}$ and CXCR7$^{QTY}$ displayed maximum emission at ~334 nm and ~338 nm, respectively (FIG. 17) suggesting the mean hydrophobic microenvironment of the tryptophan side chains is neither completely hydrophilic nor hydrophobic as expected for a folded QTY protein[49]. When both tryptophan and tyrosine are excited at 275 nm, the maxima of the fluorescence emission spectra shifted to ~332 nm for both CCR5$^{QTY}$ and CXCR7$^{QTY}$, which indicates weak emission by tyrosines (FIG. 17 inset), despite the high number of tyrosines in the QTY proteins (42 tyrosine and 5 tryptophan in CCR5$^{QTY}$, 31 tyrosine and 8 tryptophan in CCR5$^{QTY}$). The weakening of tyrosine fluorescence centered at 303 nm is due to the F~rster energy transfer from tyrosine to nearby tryptophan residues[50]. This indicates that the QTY proteins fold into a compact tertiary structure with the expected content of secondary structure.

Computer Simulation of CCR5QTY and CXCR4QTY in Explicit Water Environment

Figure 11:
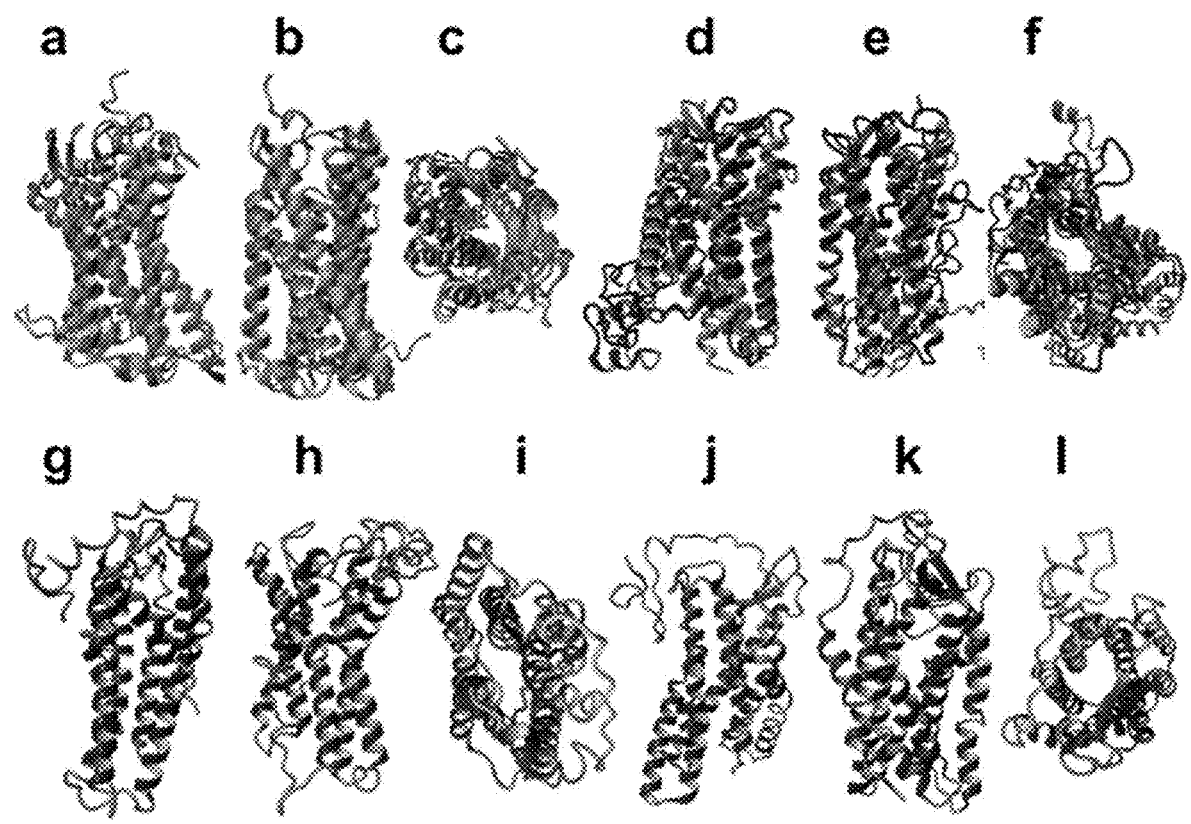

Recent advances in computer simulations of protein sequences make it possible to predict reasonably realistic structural data. We tested whether the CCR5$^{QTY}$, CXCR4$^{QTY}$, CCR10$^{QTY}$ and CXCR7$^{QTY}$ are stable by simulating them in explicit water for 1 μ second (FIG. 5). If they are not stable, these structures should not fold correctly. After an initial 0.3 μ seconds of simulations using the AMBER14 force field software[45], the overall structures were already formed and seemed to be stable; additional 0.7 μ-second simulations did not further stabilize these structures. After the simulations, CCR5$^{QTY}$ and CXCR4$^{QTY}$ were superimposed with crystal structures of the natural and detergent-bearing CCR5 (4MBS)[31] and CXCR4 (3ODU)[32], respectively. The natural CCR5 and CCR5$^{QTY}$ as well as natural CXCR4 and CXCR4$^{QTY}$ superimposed well for the 7 transmembrane segments (FIG. 11), suggesting their folded structures are similar. Currently there are no structures of CCR10 and CXCR7 available. We only simulated CCR10$^{QTY}$ and CXCR7$^{QTY}$ as working models.

Discussion

Based on the available X-ray crystal structure of CXCR4 dimmer[31], we initially applied the QTY Code and changed 28 positions (CXCR4$^{QTY}$-v28) (FIG. 15) only on the exterior surface of TM1, TM2, TM4, TM6 and TM7, but not on the interior and the dimmer interface positions. But the protein could not be expressed and purified without detergent. We then altered 56 QTY positions (CXCR4$^{QTY}$-v56) in 7TM using a random library approach. When we tried to express it in both *E. coli* and yeast, but it failed to express in the soluble fractions. We thus abandoned the random library approach. In our current experiments, we changed 85 positions in all 7TMs of CXCR4 (CXCR4$^{QTY}$-v85). This time, the protein became water-soluble without any detergents; it folded into a compact structure and retained its ligand-binding activities for CXCL12 and HIV1 gp41-120. Because of these results, additional QTY substitutions were introduced to CCR5$^{QTY}$, CXCR4$^{QTY}$, CCR10$^{QTY}$ and CXCR7$^{QTY}$ that are reported here.

CCR5$^{QTY}$, CXCR4$^{QTY}$, CCR1 (M$^{Y}$ and CXCR7$^{QTY}$ were expressed in SF9 insect cells. Although protein yields were sufficient for ligand-binding, thermostability and circular dichroism studies, the yields were not high enough to undertake structural studies and other uses. We thus expressed CXCR4$^{QTY}$ in *E. coli* cells in order to evaluate whether we could obtain enough protein. The protein was expressed in inclusion bodies at yields over 10 mg per liter. We extracted the proteins from the inclusion bodies, which itself is a significant enrichment, and further purified them via a his-tag and gel filtration column, in denatured condition. We re-folded the protein in the presence of 0.5M L-arginine. The re-folded and purified CXCR4$^{QTY}$ retained its ligand-binding activity (FIG. 9*b*), and thermostability (FIG. 10*b*).

The key scientific basis of the QTY Code is the fact that all 20 amino acids are found in ~-helices[13'], [14] though some residues like Leu (L) and Gln(Q)[13, 20] are preferred. Despite differences in their chemical properties, amino acid structures may determine protein structure in the QTY Code (FIG. 7*a*, FIG. 6) (FIG. 8, FIG. 5, FIG. 11 and FIG. 17). Our results show that despite over 20% overall protein changes, and ~50% changes in TM segments, the QTY Code-engineered CCR5$^{QTY}$, CXCR4$^{QTY}$, CCR10$^{QTY}$ and CXCR7$^{QTY}$ not only maintain their overall structure, but also bind their respective ligands.

Computer-simulations[45'] of CCR5$^{QTY}$, CXCR4$^{QTY}$, CCR10$^{QTY}$ and CXCR7$^{QTY}$ in an explicit water environment (1μ second each) show that they fold properly with 7 transmembrane α-helices that can be superimposed on the X-ray crystal structures of natural detergent-stabilized CXCR4[31] and CCR5[32], despite significant QTY substitutions (~22% for CCR5$^{QTY}$, ~29% for CXCR4$^{QTY}$). CCR10$^{QTY}$ (~19% QTY substitutions) and CXCR7$^{QTY}$ (~23% QTY substitutions) cannot be compared with native CCR10 and CXCR7 since there are no determined CCR10 and CXCR7 structures available.

We measured the ligand binding of the QTY Code-engineered chemokine receptors in both buffer and 50% human serum. The receptors have ~2-4 times lower affinity in serum than in buffer (Table 1, FIG. 9). These differences are expected since human serum is very complex and contains numerous substances, including small molecular compounds, the 20 amino acids, metabolic intermediates, peptides, proteins and more, perhaps even the same ligands. However, the affinities measured in serum are perhaps closer to real-life since the receptors are always exposed to a serum environment.

TABLE 1

The QTY engineered chemokine receptor ligand-binding measurements (nM)

| | CCL5* | | CXCL11 | | CXCL12* | | CCL27 | | CCL28 | | gp41-120 | |
|---|---|---|---|---|---|---|---|---|---|---|---|---|
| | Buffer | Serum | Buffer | Serum | Buffer | Serum | Buffer | Serum | Buffer | Serum | buffer | Serum |
| CCR5$^{QTY}$ | 33.9 ± 4.8. | 45.9 ± 7.9 | | | | | | | | | 3.1 ± 0.7, | 4.3 ± 1.5 |
| ¶CXCR4$^{QTY}$ | | | | | 11.2 ± 3.4, | 44.7 ± 8.9 | | | | | 117 ± 26, | 185 ± 25 |
| CCR10$^{QTY}$ | | | | | | | 3.1 ± 1.2, | 5.6 ± 1.1 | 9.3 ± 1.8, | 21 ± 4 | | |
| CXCR7$^{QTY}$ | | | 16 ± 3, | 28 ± 11 | 2.2 ± 0.7, | 6.6 ± 1.7 | | | | | 1.2 ± 0.4, | 7 ± 1.5 |

*CCL5 is also called RanTes and CXCL12 is also called SDF1α in the literature.
¶CXCR4$^{QTY}$ was purified from E. coli inclusion bodies.
The natural ligand affinities are known for CCR5 vs CCL5 (~4 nM), CXCR4 vs. CXCL12 (~5 nM), CCR10 vs CCL27 (~5.6 nM), CCR10 vs CCL28 (38 nM), CXCR7 vs CXCL11 (~8 nM) and CXCR7 vs CXCL12 (~4.5 nM), CCR5 vs gp120 (~10 nM), CXCR4 vs gp120 (~200 nM).
The purified chemokine receptors were subjected to ligand-binding studies with their known ligands in buffer and in 50% human serum in red (1:1 dilution, namely 1 part protein in buffer:1 part of 100% human serum). Each sample was independently measured 3 times in duplicates; total 6 measurements were carried out for each sample. The measured affinity numbers are indicated in nM. CCR5$^{QTY}$, CXCR4$^{QTY}$ and CXCR7$^{QTY}$ were also assayed for their binding to HIV coat protein gp41-120. All receptors were also measured if they bind to human Insulin as a negative control, they did not bind to human Insulin at the concentration measured (see FIG. 3). The binding affinity is lower in 50% human serum than the affinity in the pure buffer, which is anticipated due to the complexity of human serum, which contain numerous components. The ligand-binding results in serum suggest the binding specificity because human serum comprises of a complex of numerous substances that interfere the ligand-binding. It is important to carry out ligand-binding assays in human serum to be truly relevant since the proteins and their ligands do not exist in the pure buffer environment. Such assays in serum also represent more realistic conditions. But few examples of ligand binding studies were carried out in serum. CCR5$^{QTY}$ from SF9 cells was independently purified twice in ~6 months and the ligand-binding was also independently measured twice. The early purified CCR5$^{QTY}$ had $K_D$ ~42 nM and the late CCR5$^{QTY}$ had $K_D$ ~34 nM. Likewise, CXCR4$^{QTY}$ from E. coli inclusion body purification and refolding was independently purified twice in ~1 month and the ligand-binding was also Independently measured 3 times. The early purified CXCR4$^{QTY}$ had $K_D$ ~17 nM and the late CXCR4$^{QTY}$ had $K_D$ ~13 nM.

Figure 3:
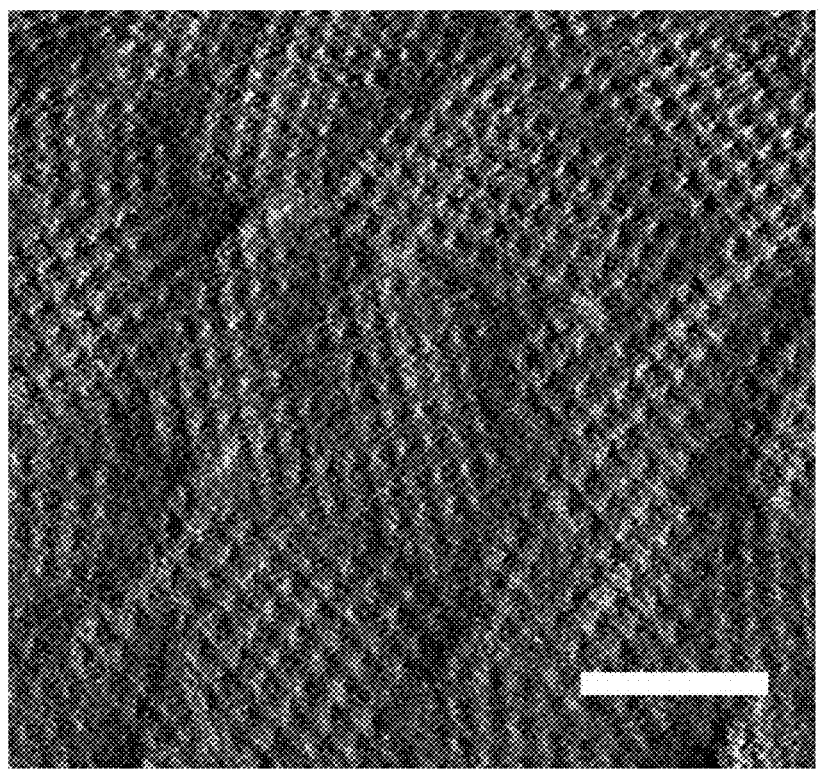
FIG. 3 is an AFM image of rSbpA$_{31-1068}$ZZ recrystallized on silicon wafer. The crystalline S-layer showing square (p4) lattice symmetry is clearly visible. Bar 100 nm.

It is interesting to observe that CXCR7$^{QTY}$ has a lower KD for CXCL12 and HIV gp41-120 than CXCR4$^{QTY}$ (FIG. 3 and Table 1). It is known that CXCR7 (also called RDC1, AKCR3, CMKOR1 and GPR159) is an atypical chemokine receptor that does not activate G-protein-mediated signal transduction. Instead, it recruits b-arrestin and functions as a scavenger for the ligands CXCL11 and CXCL12. CXCR7 can heterodimerize with CXCR4 in order to modulate CXCR4 activities[51-52]. CXCR7 can be activated by CXCL11 in malignant cells, leading to enhanced cell adhesion and migration. Elevated levels of CXCR7 expression are correlated with aggressive human prostate, breast and lung cancers, and promote growth and metastasis of various tumors[53]. Thus the higher affinity of CXCR7$^{QTY}$ for CXCL12 than CXCR4$^{QTY}$ is reasonable in such context. CCR10 and its ligands CCL27 and CCL28 are uniquely involved in the epithelial immunity and CCR10 is expressed in subsets of innate-like T cells, which are localize to the skin during their developmental processes in the thymus[54].

Figure 12:
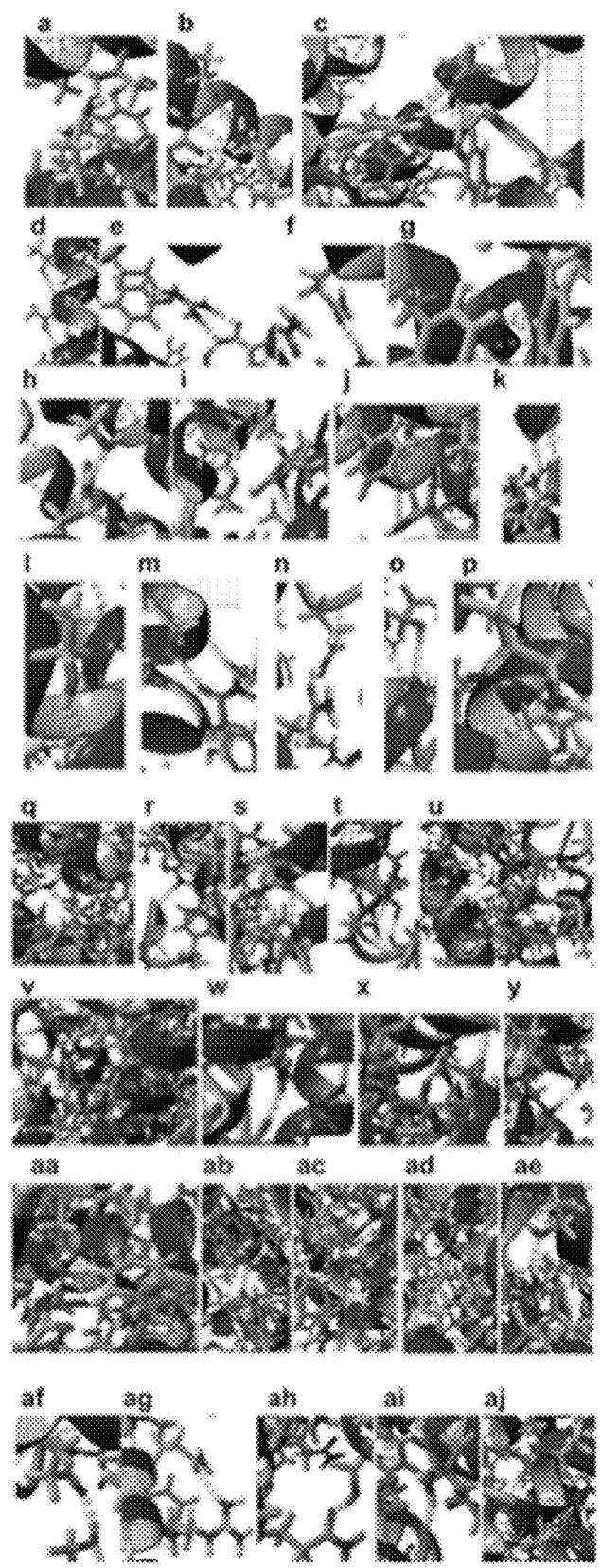

We asked why the protein structures remain stable and retain ligand-binding activity even after substantial replacement of the hydrophobic residues L, I, V and F with Q, T, and Y. We found that three types of internal hydrogen bonds formed in the simulated QTY variants that can stabilize the detergent-free protein structures: i) hydrogen bonds between side chains, ii) hydrogen bonds between side chains and backbones, and iii) hydrogen bonds within networks of side-chains with side-chains and with backbones (FIG. 12). These hydrogen bonds not only form inter-helical bonds, but also intra-helical bonds. Thus these hydrogen bonds can stabilize both individual helices and adjacent helices. It is believed that these additional internal hydrogen bonds may stabilize the structures of the QTY variants.

FIG. 12 illustrates the likely hydrogen bonds within intra- and inter-helices. In the example of Q121s-T152s-T148b: 's' denotes a side chain bond and 'b' denotes a backbone bond. The side chain of Q at location 121 forms a hydrogen bond with the side chain of T at location 152, which forms a hydrogen bond with the backbone of T at 148. For example, i) in CCR5$^{QTY}$: (a) Q121s-T152s-T148b, (b) Q252s-Q256s-T199s-T195b, (c) Y118s-E283s-R247s, (d) T143b-T147s,b-T150s,b-T154s, where 4 consecutive T form hydrogen bonds on their side chains in addition to the intra-helical hydrogen bonds, likely further stabilizing the structure, (e) Q33s-Q277s, (f) Q68s-D125s-R140s, (g) Y79s-Y108s; ii) in CXCR4$^{QTY}$: (h) Q260s-S260s-Y256b, (i) T215b-Q216s-Q246s, (j) Y249s-Q253, (k) Q167s-H203b, (l) T169s-Q165b, (m) T204s-Q208s, (n) Q78s-Q69s-Q69b, (o) T112s-Q108b, (p) Q290s-T287b; iii) in CCR10$^{QTY}$: (q) D35s-R192s-D289s, (r) Y14s-Q172-Q214/Q172-S106b, (s) Q63s-Q82s, (t) Q167s-T163s-H159b, (u) Q54s-Q305s-Y256b-Q252s-Q81s-T308s, (v) H66s-Q63s-Q82/Q63s-N306b, (w) Q259s-Q298s, (x) Y263s-Q211s-S207b, (y) D270s-Q292s, iv) in CXCR7$^{QTY}$: (aa) Y257s-Q86s-S131s, (ab) Y124s-Y268s, (ac) Y315s-N69s-H80s, (ad) Y232s-T259s, (ae) T260s-H307s, (af) Q273-S15s, (ag) Q234s-R237s, (ah) Q314s-S256s, (ai) Q297s-A271b, (aj) T310-T306b, T313s-C309b.

These additional hydrogen bonds are the direct result of introducing QTY variants. In the native CCR5, CXCR4, CCR10 and CXCR7, these hydrogen bonds cannot form since the side chains of L, V, I and F do not have —OH and $H_2N$—CH—C=O groups, and therefore do not have hydrogen bond forming capabilities. Numerous additional internal hydrogen bonds may stabilize the structures of the QTY variants, as shown by their Tm.

For comparison, the natural ligand affinities are known for CCR5 vs CCL5 (~4 nM)[27], CXCR4 vs CXCL12 (~5 nM)[27], CCR10 vs CCL27 (~5.6 nM)[55], CCR10 vs CCL28 (~38 nM)[56], CXCR7 vs CXCL11 (~8 nM)[57], CXCR7 vs CXCL12 (~4.5 nM)[57], CCR5 vs gp120 (~10 nM)[58] and CXCR4 vs gp120 (~200 nM)[24]. However, since the natural ligand-binding studies were carried out in various conditions, often in cell-based assays, it is difficult to compare them directly. These natural affinities show that the QTY engineered variants have similar ligand affinities, further suggesting they retained ligand-binding activities.

In humans, chemokine receptors CCR5, CXCR4 and CXCR7 are used by AIDS viruses as entrances into T cells for the widely spread infections[28-30]. Since detergent-free variants CCR5$^{QTY}$ (~4.3 nM) and CXCR7$^{QTY}$ (~7 nM) in 50% human serum have high affinities to HIV coat proteins gp41-120 (Table 1, FIG. 9), CCR5$^{QTY}$ and CXCR7$^{QTY}$ may be further engineered as possible decoy therapies for prevention and treatment of AIDS, and to design a sensitive and rapid sensing device in order to detect AIDS viruses early.

The QTY Code will likely allow systematic engineering of a variety of proteins through simple, specific amino acids substitutions (FIG. 7A). The QTY Code is perhaps also reversible if one desires to engineer a water-soluble protein to anchor it to the lipid membrane. The QTY Code is analogous to the nucleic acid code in DNA, where A pairs with T, G pairs with C, and vice versa.

CCR5$^{QTY}$, CXCR4$^{QTY}$, CCR10$^{QTY}$, CSCR7$^{QTY}$ and QTY Code engineered additional detergent-free chemokine receptors, as well as other GPCRs, may find many applications in biotechnology. It may be possible to use QTY-altered receptors in a manner similar to water-soluble kinases and proteases in drug discoveries. They may potentially be used as reagents in deorphanization studies. It may even be possible to use them as decoys to treat autoimmune diseases and other diseases.

The QTY Code is not only robust and straightforward, it is the simplest tool to carry out membrane protein engineering. It is also a significant improvement over previous attempts using non-systematic mutations[6-10]. Our simple QTY Code will likely have significant implications for engineering water-insoluble proteins since it can be applied to many proteins in addition to GPCRs and other membrane proteins. For example, it may be useful in studies of many other water-insoluble and aggregated proteins[59], including α-amyloid peptides, islet amyloid polypeptide, b2-microglobulin, Medin, Calcitonin, Serum amyloid A, and monoclonal antibodies.

Methods

Yeast 2-Hybrid Assays

We tested Y2H interactions in Saccharomyces cerevisiae selection strain Y187 (MATa, ura3-52, his3-200, ade2-101, trp1-901, leu2-3, 112, gal4Δ, met-, gal80Δ, MEL1, URA3::GAL1uas-GAL$_{TATA}$-lacZ) containing the library (either CCR5$^{QTY}$ and CXCR4$^{QTY}$) with mating partner Y2HGold (MATa, trp1-901, leu2-3, 112, ura3-52, his3-200, gal4Δ, gal80Δ, LYS2:: GAL1UAS~Gal1TATA~His3, GAL2UAS~Gal2TATA~Ade2, URA3 ~MEL1UAS-Mel1TATA, AUR1-C MEL1). Ligands and receptors were expressed in both strains for interaction testing in different orientations. These strains are effective in minimizing false positive protein interactions and background during a typical GAL4 based 2-hybrid screen.

We deleted the intracellular C-terminal domains of the QTY variants for better expression and to avoid non-specific protein interactions in the Y2H fusion proteins. The CXCR4$^{QTY}$ DNA was amplified and cloned into the bait vector pGBKC-20GS and the prey vector pGADC-20GS with the corresponding flanking sequences. The bait and prey inserts were amplified with Phusion enzyme, and purified PCR products were cloned into the bait vector pGBKC-GS20 and the prey vector pGADC-2A. Ligands were cloned by yeast in vivo recombination or by Gibson cloning into EcoRI-BamHI linearized bait and prey vectors. All bait and prey inserts and customized vector elements were synthesized by Integrated DNA Technologies or Quintara Biosciences. After cloning into the vectors, bait and prey constructs were confirmed by DNA sequencing and tested for toxicity and self-activation before the assays.

In our custom made Y2H vectors, the DNA binding and activation domains are at the C-termini of the Y2H fusion proteins. In pGADC-2A, the insert is separated by a multiple cloning site (MCS) and an HA-tag from the C-terminal GAL4 activation domain (GAL4-AD), while in pGADC-GS20, the insert is separated from the GAL4-AD by a 20 amino acid polylinker (GS20) enriched in Serine and glycine (SGGGSGGGASSGGGAGGGAS (SEQ ID NO: 1)). Likewise, in the bait vector pGBKC-3C, the insert is separated by a MCS and a Myc-tag from the C-terminal GAL4 DNA binding domain (GAL4-DBD), while pGADC-GS20 contains the GS20 polylinker instead. Fusion protein expression in Y2H vectors is driven by ADH1 promoters. All bait and prey coding sequences are codon optimized for expression in S. cerevisiae and preceded by a Kozak sequence. Bait vectors contain the TRP1 gene and prey vectors the LEU2 for auxotrophic selection.

Bioinformatics of the QTY Variants

The variant protein sequences were first evaluated to determine if transmembrane segments still exist using a web-based tool TMHMM Server v. 2.0 that predicts of transmembrane helices: www.cbs.dtu.dk/services/TMHMM-2.0/ (FIG. 15). In order to assess solubility before these proteins were produced and purified, the variant protein sequences were placed through the solubility website pepcale.com/peptide-solubility-calculator.php. Additional QTY changes were introduced into the 7 transmembrane segments. In CXCR4QTY case, additional QTY amino acids were also introduced into the intracellular loops and C-terminus since these parts most likely do not bind to the chemokine ligands.

Protein Expression Using the Baculovirus System/SF9 Insect Cells

CCR5$^{QTY}$ variant gene sequences selected in the yeast 2-hybrid screen were synthesized with a C-terminal His-tag (Biomatik). Sequences were cloned into a pOET2 transfer vector (Oxford Expression Technologies). Resulting baculovirus preparations were generated using the FlashBacUltra Kit (Oxford Expression Technologies) and amplified to high titer virus stocks.

SF9 insect cells (Oxford Expression Technologies) were infected and cultured in 2 liter aerated spinner flasks in serum-free medium (Lonza) for 48 hours post infection at 27° C. Cells were collected by centrifugation at 1,500 rpm and the cell pellet was stored at −80° C.

His-tag Affinity and Gel Filtration Purification of QTY Variants

SF9 Cells were lysed by sonication in PBS buffer, pH7.5, containing 10 mM DTT. No detergent was used. The cells were centrifuged at 20,000X g and the supernatant was subjected to batch binding for 2 hours using a DTT stable Ni-Agarose resin (PureCube 100 INDIGO, Cube Biotech). The bound His-tagged protein was washed extensively using PBS, pH7.5, with 20 mM imidazole. Protein was eluted with PBS, pH7.5, 250 mM imidazole. Elution fractions were concentrated with Amicon centrifugal filter units (Merck Millipore) and loaded onto a Superdex200 10/300 GL gel filtration column (GE Healthcare). The final protein was eluted in PBS, pH7.5, and was concentrated using Amicon centrifugal filter units (Merck Millipore) to 0.5 mg/ml.

Protein Expression and Purification from E. coli Inclusion Bodies and Refolding

Plasmids containing the CXCR4$^{QTY}$ gene with E.coli codon optimization were obtained from Genscript and transformed into BL21 (DE3) E. coli. Transformants were selected on LB medium plates with 100 µg/ml Carbenicillin resistance. E. coli cultures were grown at 37° C. until the OD$_{600}$ reached 0.4-0.8, after which IPTG (isopropyl-D-thiogalactoside) was added to a final concentration of 1 mM followed by 4 hour expression. Cells were collected and lysed by sonication in B-PER protein extraction agent (Thermos-Fisher). Lysate was centrifuged (23,000×g, 40 min, 4° C.), and the pellet were subsequently washed and was sonicated twice in buffer 1 (50 mM Tris.HCl pH7.4, 50 mM NaCl, 10 mM $CaCl_2$, 0.1% v/v Trition X100, 2M Urea, 0.2 μm filtered), once in buffer 2 (50 mM Tris.HCl pH7.4, 1M NaCl, 10 mM $CaCl_2$, 0.1% v/v Trition X100, 2M Urea, 0.2 μm filtered) and again in buffer 1. Pellets from each washing step and the final inclusion body (IB) were collected by centrifugation (23,000×g, 25 min, 4° C.).

After the inclusion bodies were washed extensively, they were solubilized in denaturation buffer (6M guanidine hydrochloride, 1xPBS, 10 mM DTT) at room temperature for 1 hour with magnetic stirring. The solution was centrifuged at 23,000xg for 40 min at 4° C. The supernatant with proteins were purified by Qiagen Ni-NTA beads (His-tag) followed by gel-filtration chromatography using a AKTA Purifier system and a GE healthcare Superdex 200 HiLoad 16/600 column. Samples were 0.2 μm filtered before they were applied to the column. Portions with purified protein were collected and dialyzed against re-naturation buffer (50 mM Tris.HCl pH9.0, 3 mM reduced glutathione, 1 mM oxidized glutathione, 5 mM EDTA, and 0.5M Arginine which is the key ingredient). Following an overnight refolding process, the re-natured protein solution was dialyzed against 50 mM Tris.HCl, pH 9.0, and centrifuged (23,000×g, 30 min, 4° C.) to remove potential protein aggregates from the refolding process. Arginine can be added to the final solution to regulate the solubility of the protein. The protein fractions were run on SDS PAGE.

Receptor Protein Labeling

Since $CCR5^{QTY}$, $CXCR4^{QTY}$, $CXCR7^{QTY}$, $CCR10^{QTY}$ receptors and their respective ligands (CCL5, CXCL12, CCL27 and CCL28) contain tryptophans, the receptors need to be labeled with NT647 in 1XPBS pH7.4 in order to reduce noise and obtain unique fluorescent signals. These receptors were labeled according to the instructions of the Monolith NT™ Protein Labeling Kit RED—NHS (NanoTemper Technologies, Munich, Germany). The concentration of labeled proteins was determined using NanoDrop and Bradford assays.

MicroScale Thermophoresis Measurements

MicroScale Thermophoresis (MST) binding experiments were carried out with 5 nM NT64seven-labeled protein ($CCR5^{QTY}$, $CXCR4^{QTY}$, $CCR10^{QTY}$ or $CXCR7^{QTY}$) in binding buffer (1× PBS, 5 mM DTT) with 0.0916 nM-3000 nM of the respective ligand (Rantes and/or SDF1a), 0.153 nM-5,000 nM insulin, 0.0651 nM-2,000 nM CCL28 and CXCL11, 0.012 nM-400 nM for CCL27 and 0.0153 nM-500 nM gp41-120 at 80% MST power, 15% LED power in premium capillaries on a Monolith NT.115 pico instrument at 25° C. (NanoTemper Technologies, Munich, Germany). MST time traces were recorded and the TJump+Thermophoresis or respectively Thermophoresis was analyzed. The recorded fluorescence was plotted against the concentration of ligand and curve fitting was performed with Kaleida-Graph 4.5 using the KD fit formula derived from the law of mass action. For clarity, binding graphs of each independent experiment were normalized to fraction bound (0=unbound, 1=bound). Prior to each measurement, protein concentrations were precisely measured by a Bradford assay, Nano-Drop and Qbit. An average of the fraction-bound normalized data for 3 independent experiments is shown in FIG. 9 and Table 1.

nanoDSF Determination of the Thermal Stability of the QTY Variants

For thermal unfolding experiments, $CCR5^{QTY}$, $CXCR4^{QTY}$, $CCR10^{QTY}$ or $CXCR7^{QTY}$ were diluted to a final concentration of 5 μM in PBS+5 mM DTT. For each condition, 10 μl of sample per capillary was prepared. The samples were loaded into UV capillaries (NanoTemper Technologies) and experiments were carried out using the Prometheus NT.48. The temperature gradient was set to increase 1° C./min in a range from 20° C. to 90° C. For negative controls, $CCR5^{QTY}$, $CXCR4^{QTY}$, $CCR10^{QTY}$ and $CXCR7^{QTY}$ were heated to 90° C. for 15 minutes to denature them. Protein unfolding was measured by detecting the temperature-dependent change in tryptophan fluorescence at emission wavelengths of 330 nm and 350 nm. Melting temperatures were determined by detecting the maximum of the first derivative of the fluorescence ratios (F330/ F350) for $CCR5^{QTY}$, $CXCR4^{QTY}$, $CCR10^{QTY}$ or $CXCR7^{QTY}$. The first derivative F350 was used for $CCR10^{QTY}$. For this, an $8^{th}$ order polynomial fit was calculated for the transition region. The first derivative of the fit and the peak position (at Tm) were then determined. Three independent experiments were performed.

Circular Dichroism and Fluorescents Measurements

CD and fluorescence spectra were recorded using an Aviv425 Circular Dichroism spectrometer (Lakewood, N.J., USA) equipped with a fluorescence emission scanning monochromator. The QTY Protein sample was buffer exchanged by dialysis into CD buffer (10 mM sodium phosphate, pH 7.4, 150 mM NaF, 1 mM TCEP). The sample was filtered through a 0.2 μm-filter before measurement. For far UV CD, spectra between 183 nm and 260 nm were collected with a 1nm step size, 1nm bandwidth and 15-second averaging time in a 0.1 cm path length cuvettes. The CD dynode voltage was kept below 700V over all the wavelengths. Baselines were measured using buffer solutions alone without any protein. Baseline subtraction and spectra smoothing were carried out with Aviv CDS software. The protein concentration was ~1.2 μM. The baseline-subtracted spectra were scaled to obtain Mean Residue Ellipticities (MREs). The algorithm CDSSTR with the reference data sets 4, 7 and SMP 180 was used for deconvolution. The fluorescence spectra (308 nm to 450 nm) were recorded with 275 nm and 295 nm excitation respectively with a bandwidth of 2 nm, a photo multiplier tube voltage of 900V, an averaging time of 1 second and an emission slit setting of 2 mm.

Computer simulations of $CCR5^{QTY}$, $CXCR4^{QTY}$, $CCR10^{QTY}$ and $CXCR7^{QTY}$ in Explicit Water Environment The published crystal structures of CCR5 (4MBS) and CXCR4 (3ODU) were obtained from the Protein Data Bank. Predicted initial structures of the QTY candidates were obtained from the predicted sequence and the GOMoDo modeling server[45]. The $CCR5^{QTY}$ sequence is 78.12% identical to CCR5, and the $CXCR4^{QTY}$ sequence is 70.74% identical to CXCR4. $CCR5^{QTY}$ and $CXCR4^{QTY}$, $CCR10^{QTY}$ and $CXCR7^{QTY}$ were simulated for 1μ second each in explicit water using the AMBER14 $N^{46}$ self-parameterizing force field within the simulation software YASARA[47]. The two models were then aligned to their detergent-encapsulated counterparts CCR5 and CXCR4 using MUSTANG[48] and superimposed. Since there are no structures of $CCR10^{QTY}$ and $CXCR7^{QTY}$ are available, these 2 receptors are not compared with natural CCR10 and CXCR7. The computer used for the simulations was built with an Intel Core iseven-6950X10-Core 3.0 GHzProcessor, GIGABYTE GeForce GTX 1080 Video Card, and 16 GB of DDR4 2800 memory.

REFERENCE LIST B

1. Vinothkumar, K. R. & Henderson, R. Structures of membrane proteins. *Quarterly Reviews of Biophysics* 43, 65-158 (2010).

2. Lv. X. et al. In vitro expression and analysis of the 826 human G protein-coupled receptors. *Protein Cell* 7, 325-337 (2016).
3. Scott, D. J., Kumar, L. Tremmel, D. & Plückthun, A. Stabilizing membrane proteins through protein engineering. *Current Opinion in Chemical Biology* 17, 427-435 (2013).
4. Hardy, D., Bill, R. M., Jawhari, A & Rothnie, A. Overcoming bottlenecks in the membrane protein structural biology pipeline. *Biochem. Soc. Trans.* 44, 838-844 (2016).
5. Mizrachi, D. et al. Making water-soluble integral membrane proteins in vivo using an amphipathic protein fusion strategy. *Nature Commun.* 6, 6826. (2015)
6. Slovic, A. M. et al Computational design of a water-soluble analog of phospholamban. *Protein Science* 12, 337-348 (2003).
7. Slovic, A. M. et al. Computational design of water-soluble analogues of the potassium channel KcsA. *Proc. Natl. Acad. Sci USA.* 101, 1828-1833 (2004).
8. Slovic, A. M. et al. X-ray structure of a water-soluble analog of the membrane protein phospholamban: sequence determinants defining the topology of tetrameric and pentameric coiled coils. *J. Mol. Biol.* 348, 777-787 (2005).
9. Perez-Aguilar, J. M. et al. A computationally designed water-soluble variant of a G-protein-coupled receptor: the human mu opioid receptor. *PLoS ONE* 8, e66009 (2013).
10. Zhao, X. et al. Characterization of a computationally designed water-soluble human μ-opioid receptor variant using available structural information. *Anesthesiology* 121, 866-875 (2014).
11. Thomson, A. R. et al. Computational design of water-soluble α-helical barrels. *Science* 346, 485-488 (2014).
12. Huang, P. S., Boyken, S. E. & Baker, D. The coming age of de novo protein design. *Nature* 537, 320-327 (2016).
13. Fersht, A. (1998) Structure and Mechanism in Protein Science: *A guide to enzyme catalysis and protein folding*. W. H. Freeman, N.Y., pages 10-13, 523-532.
14. Brändén, C. & Tooze, J. *Introduction to protein structure.* $2^{nd}$ Edition. Garland Publishing, London, UK, N.Y., p. 15-17 (1999).
15. Perutz, M. F., et al. Structure of haemoglobin: a three-dimensional Fourier synthesis at 5.5 Å resolution, obtained by X-ray analysis. *Nature* 185, 416-422 (1960).
16. Weed, R. I., Reed, C. F. & Berg, G. Is hemoglobin an essential structural component of human erythrocyte membranes? *J Clin Invest.* 42, 581-588 (1963).
17. Fersht, A. & Kaethner, M. M. Enzyme hyperspecificity: rejection of threonine by the Valyl-trna synthetase by misacylation and hydrolytic editing. *Biochemistry,* 15, 3342-3346 (1976).
18. Lin, L., Hale, S. P., Schimmel, P. Aminoacylation error correction. *Nature* 384, 33-34 (1996).
19. Lin, L. & Schimmel, P. Mutational analysis suggests the same design for editing activities of two tRNA synthetases. *Biochemistry* 35, 5596-5601 (1996).
20. Chou, P. Y. & Fasman, G. D. Empirical Predictions of Protein Conformation. *Ann. Rev. Biochemistry* 47, 251-276. (1978).
21. Dorsam R. T. & Gutkind, J. S. G-protein-coupled receptors and cancer. *Nat Rev. Cancer* 7, 79-94 (2007).
22. O'Hayre, M., Degese, M. S., Gutkind, J. S. Novel insights into G protein and G protein-coupled receptor signaling in cancer. *Curr Opin Cell Biol* 27, 126-35 (2014).
23. Halvorsen, E. C. et al. Maraviroc decreases CCL8-mediated migration of CCR5(+) regulatory T cells and reduces metastatic tumor growth in the lungs. *Oncoimmunology* 5, e1150398 (2016).
24. Babcock, G. J., Mirzabekov, T., Wojtowicz, W. & Sodroski, J. Ligand binding characteristics of CXCR4 incorporated into paramagnetic proteoliposomes. *J. Bio. Chem.* 276, 38433-38440 (2001).
25. Stenlund, P., Babcock, G. J., Sodroski, J. & Myszka, D G. Capture and reconstitution of G protein-coupled receptors on a biosensor surface *Analytical Biochemistry* 316, 243-250 (2003).
26. Navratilova, I., Sodroski, J. & Myszka, D G. Solubilization, stabilization, and purification of chemokine receptors using biosensor technology. *Analytical Biochemistry* 339, 271-281 (2005).
27. Navratilova, I., Dioszegi, M. & Myszka, D G. Analyzing ligand and small molecule binding activity of solubilized GPCRs using biosensor technology. *Analytical Biochemistry* 355, 132-139 (2006).
28. Oberlin, E. et al. The CXC chemokine SDF-1 is the ligand for LESTR/fusin and prevents infection by T-cell-line-adapted HIV-1. *Nature* 382, 833-835 (1996).
29. Bleul et al. The HIV co-receptors CXCR4 and CCR5 are differentially expressed and regulated on human T lymphocytes. *Proc. Natl. Acad. Sci. USA,* 94, 1925-1930 (1997).
30. Jin, J. et al. Targeting spare CC chemokine receptor 5 (CCR5) as a principle to inhibit HIV-1 entry. *J. BIOL. CHEM.* 289, 19042-19052, (2014).
31. Wu, B. et al. Structures of the CXCR4 chemokine GPCR with small-molecule and cyclic peptide antagonists. *Science* 330, 1066-1071 (2010).
32. Tan, Q. et al. Structure of the CCR5 chemokine receptor-HIV entry inhibitor maraviroc complex. *Science* 341, 138seven-1390 (2013).
33. Fields, S. & Song, O. A novel genetic system to detect protein-protein interactions. *Nature* 340, 245-246 (1989).
34. Li, J., Gao, J., Han, L. Zhang, Y., Guan, W., Zhou, L., Yu, Y. & Han, W. Development of a membrane-anchored ligand and receptor yeast two-hybrid system for ligand-receptor interaction identification. *Scientific Reports* 6, 35631. (2016).
35. Eble, J. A., Beermann, B., Hinz, H. J., & Schmidt-Hederich, A. alpha 2beta 1 integrin is not recognized by rhodocytin but is the specific, high affinity target of rhodocetin, an RGD-independent disintegrin and potent inhibitor of cell adhesion to collagen. *J. Biol. Chem.* 276, 12274-12284 (2001).
36. Duhr, S. & Braun, D. Why molecules move along a temperature gradient. *Proc Natl Acad Sci USA* 103, 19678-19682 (2006).
37. Wienken, C. J., et al. Protein-binding assays in biological liquids using microscale thermophoresis. *Nature Commun.* 1, 100 (2010).
38. Baaske, P., Wienken, C., Willemsen, M. J. & Braun, D. Protein-binding assays in biological liquids using microscale thermophoresis. *J. Biomol. Tech.* 22, S55 (2011).
39. Wang, X. et al. Peptide surfactants for cell-free production of functional G protein-coupled receptors. *Proc Natl Acad Sci* 108, 9049-9054 (2011).
40. Corin K. et al Structure and function analyses of the purified GPCR human vomeronasal type 1 receptor 1. *Sci Rep* 1, 172 (2011).

41. Seidel S. A. et al. Microscale thermophoresis quantifies biomolecular interactions under previously challenging conditions. *Methods* 59, 301-315 (2013).
42. Parker J. L., Newstead, S. Molecular basis of nitrate uptake by the plant nitrate transporter NRT1.1. *Nature* 507, 68-72 (2014).
43. Tegler, L. T., et al. Cell-free expression, purification, and ligand-binding analysis of Drosophila melanogaster olfactory receptors DmOR67a, DmOR85b and DmORCO. *Scientific Reports* 5, 7867 (2015).
44. Möller, F. M., Kiess, M. & Braun, D. Photochemical microscale electrophoresis allows fast quantification of biomolecule binding. *J Am Chem Soc.* 138, 5363-5370 (2016).
45. Sandal, M., Duy, T. P., Cona, M., Zung, H., Carloni, P. et al. GoMoDo: A GPCRs Online Modeling and Docking Webserver. *PLoS ONE* 8: e74092 (2013).
46. Case, D. A. et al. Amber 14N ambermd.org, University of California, San Francisco. Calif., USA.
47. Krieger, E. et al. Improving physical realism, stereochemistry, and side-chain accuracy in homology modeling: Four approaches that performed well in CASP8. *Proteins.* 77 Suppl. 9, 114-122 (2009).
48. Konagurthu, A. S., Whisstock, J. C., Stuckey, P. J. & Lesk, A. M. MUSTANG: A multiple structural alignment algorithm. *Proteins* 64, 559-574 (2006).
49. Reshetnyak, Y. K. & Burstein, E. A. Decomposition of protein tryptophan fluorescence spectra into log-normal components. II. The statistical proof of discreteness of tryptophan classes in proteins, *Biophys J* 81, 1710-1734 (2001).
50. Edelhoch, H., Perlman, R. L. & Wilchek, M. Tyrosine fluorescence in proteins. Ann N Y Acad Sci, 158, 391-409 (1969).
51. Balabanian, K., Lagane, B., Infantino, S., Chow, K. Y., Harriague J, et al. The chemokine SDF-1/ CXCL12 binds to and signals through the orphan receptor RDC1 in T lymphocytes. J Biol Chem 280: 35760-35766 (2005).
52. Naumann, U., Cameroni, E., Pruenster, M., Mahabaleshwar. H., Raz. E. et al. CXCR7 Functions as a Scavenger for CXCL12 and CXCL11. *PLoS ONE* 5, e9175 (2010).
53. Miao, Z., Luker, K. E., Summers, B. C., Berahovich, R., Bhojani, M.S., et al. CXCR7 (RDC1) promotes breast and lung tumor growth in vivo and is expressed on tumor-associated vasculature. *Proc Natl Acad Sci USA* 104, 15735-15740 (2007).
54. Xiong, N., Fu, Y., Hu, S., Xia, M. & Yang, J. CCR10 and its ligand in regulation of epithelial immunity and diseases. *Protein Cell* 3, 571-580 (2012).
55. Pan, et al. A novel chemokine ligand for CCR10 and CCR3 expressed by epithelial cells in mucosal tissues. J. Immul. 165, 2943-2949 (2000).
56. Wang et al. Identification of a Novel Chemokine (CCL28), which Binds CCR10 (GPR2) *J. Biol. Chem.* 275, 22313-22323 (2000).
57. Benredjem, B., Girard, M., Rhainds, D., St.-Onge, G., & Heveker, N. Mutational Analysis of atypical chemokine receptor 3 (ACKR3/ CXCR7) interaction with its chemokine ligands CXCL11 and CXCL12. *J. Biol. Chem.* 292, 31-42 (2017).
58. Navratilova, I., Sodroski, J., Myszka, D.G. Solubilization, stabilization, and purifcation of chemokine receptors using biosensor technology. *Analytical Biochemistry* 339, 271-281 (2005).
59. Gazit, E. Mechanisms of amyloid fibril self-assembly and inhibition: model short peptides as a key research tool, *FEBS J* 272, 5971-5978 (2005).

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A bioelectronic interface comprising:
   a) a solid substrate; and
   b) a plurality of self-assembling units wherein:
      i. each self-assembling unit comprises a variant G-protein coupled receptor (GPCR) fusion protein bound to an S-layer fusion protein;
      ii. the S-layer fusion protein comprises an S-layer protein and a fusion domain, wherein the N-terminus of the S-layer fusion protein is bound to the surface of the solid substrate, wherein the fusion domain is fused to the C-terminus of the S-layer protein, and wherein a plurality of S-layer fusion proteins form a two-dimensional crystalline lattice on the surface of the solid substrate;
      iii. the variant GPCR fusion protein comprises a variant GPCR and a binding moiety;
         wherein the variant GPCR is a water-soluble variant of a native GPCR, wherein a plurality of amino acid residues Leucine (L), isoleucine (I), valine (V), and phenylalanine (F) within the seven-transmembrane a-helical domain of the native GPCR are replaced with glutamine (Q), threonine (T), threonine (T), and tyrosine (Y), respectively; and
         wherein the binding moiety is fused to the C-terminus of the variant GPCR and has binding affinity for the fusion domain of the S-layer fusion protein, and further wherein the binding moiety is bound to the fusion domain.

2. The bioelectronic interface of claim 1, wherein the S-layer protein is C-terminally truncated.

3. The bioelectronic interface of claim 1, wherein the S-layer protein is a recombinant protein.

4. The bioelectronic interface of claim 1, wherein recombinant protein is expressed in *E. coli*.

5. The bioelectronic interface of claim 1, wherein the S-layer protein is SbpA from *Lysinibacillus sphaericus* CCM 2177.

6. The bioelectronic interface of claim 2, wherein the S-layer fusion protein is rSbpA$_{31-1068}$ZZ.

7. The bioelectronic interface of claim 1, wherein the surface of the substrate is semi-conductive or conducting.

8. The bioelectronic interface of claim 1, wherein the substrate is a silicon wafer, a carbon nanotube, or graphene.

9. The bioelectronic interface of claim 1, wherein the surface of the substrate comprises a metal oxide.

10. The bioelectronic interface of claim 9, wherein the oxide is indium tin oxide (ITO) or aluminum oxide.

11. The bioelectronic interface of claim 1, wherein the substrate is part of a bioelectronic device.

12. The bioelectronic interface of claim 1, wherein the fusion domain is a polypeptide comprising the Fc binding domain of Protein A, Protein G, or Protein A/G and the binding moiety is an Fc region.

13. The bioelectronic interface of claim 12, wherein the fusion domain is an Fc binding region of Protein A.

14. The bioelectronic interface of claim 1, wherein the fusion domain is an antibody or an antigen-binding portion thereof and the binding moiety is an antigen that binds the antibody or the antigen-binding portion thereof.

15. The bioelectronic interface of claim 1, wherein the fusion domain is an antigen and the binding moiety is an antibody or antigen-binding portion thereof that binds to the antigen.

16. The bioelectronic interface of claim 1, wherein at least about 75% of the hydrophobic amino acid residues within the seven-transmembrane domain are replaced.

17. The bioelectronic interface of claim 1, wherein the plurality of self-assembling units comprise at least two different GPCR variant proteins.

18. A biosensor for detecting the binding of a potential ligand to the variant GPCR, wherein the biosensor comprises the bioelectronic interface of claim 1, and wherein the binding of the potential ligand to the variant GPCR produces a detectable signal.

19. The biosensor of claim 18, wherein the detectable signal is an electrical, electrochemical, dielectric, or fluorescence signal.

20. A method for screening for a ligand of a G-protein coupled receptor (GPCR) comprising the steps of:
   a. contacting a potential ligand with the bioelectronic interface of claim 1; and
   b. measuring the binding of the potential ligand to the variant GPCR, wherein the binding of the potential ligand to the variant GPCR is indicative of binding to the native GPCR.

21. The method of claim 20, wherein binding is measured by measuring a detectable signal.

22. A method for detecting a G-protein coupled receptor (GPCR) ligand in a sample comprising the steps of:
   a. contacting the sample with the bioelectronic interface of claim 1; and
   b. measuring the binding of the ligand to the variant GPCR, wherein the binding of the ligand to the variant GPCR is indicative of binding to the native GPCR.

23. A method for screening for a potential ligand for binding to a G-protein coupled receptor (GPCR) comprising the steps of:
   a) contacting a potential ligand with a variant GPCR immobilized on a solid substrate, wherein the variant GPCR is part of a self-assembling unit that comprises a variant GPCR fusion protein bound to an S-layer fusion protein; wherein:
      i. the S-layer fusion protein comprises an S-layer protein and a fusion domain, wherein the N-terminus of the S-layer fusion protein is bound to the surface of the solid substrate, wherein the fusion domain is fused to the C-terminus of the S-layer protein, and wherein a plurality of S-layer fusion proteins self-assembles into a two-dimensional crystal lattice on the surface; and
      ii. the variant GPCR fusion protein comprises a variant GPCR and a binding moiety;
   wherein the variant GPCR is a water-soluble variant of a native GPCR wherein a plurality of amino acid residues Leucine (L), isoleucine (I), valine (V), and phenylalanine (F) within the seven-transmembrane a-helical domain of the native GPCR are replaced with glutamine (Q), threonine (T), threonine (T), and tyrosine (Y), respectively; and
   wherein the binding moiety is fused to the C-terminus of the variant GPCR, has binding affinity for the fusion domain of the S-layer fusion protein, and further wherein the binding moiety is bound to the fusion domain; and
   b) measuring the binding of the potential ligand to the variant GPCR, wherein the binding of the potential ligand to the variant GPCR is indicative of binding to the native GPCR.

24. A method for detecting a G-protein coupled receptor (GPCR) ligand in a sample comprising the steps of:
   a. contacting the sample with a variant GPCR immobilized on a solid substrate, wherein the variant GPCR is part of a self-assembling unit that comprises a variant GPCR fusion protein bound to an S-layer fusion protein; wherein:
      i. the S-layer fusion protein comprises an S-layer protein and a fusion domain, wherein the N-terminus of the S-layer fusion protein is bound to the surface of the solid substrate, wherein the fusion domain is fused to the C-terminus of the S-layer protein, and wherein a plurality of S-layer fusion proteins self-assembles into a two-dimensional crystal lattice on the surface; and
      ii. the variant GPCR fusion protein comprises a variant GPCR and a binding moiety; wherein the variant GPCR is a water-soluble variant of a native GPCR wherein a plurality of amino acid residues Leucine (L), isoleucine (I), valine (V), and phenylalanine (F) within the seven-transmembrane a-helical domain of the native GPCR are replaced with glutamine (Q), threonine (T), threonine (T), and tyrosine (Y), respectively; and
   wherein the binding moiety is fused to the C-terminus of the variant GPCR, has binding affinity for the fusion domain of the S-layer fusion protein, and further wherein the binding moiety is bound to the fusion domain; and
   b. measuring the binding of the ligand to the variant GPCR, wherein the binding of the potential ligand to the variant GPCR is indicative of binding to the native GPCR.

25. A self-assembling unit comprising a variant GPCR fusion protein bound to an S-layer fusion protein wherein:
   i. the S-layer fusion protein comprises an S-layer protein and a fusion domain, wherein the N-terminus of the S-layer fusion protein is bound to the surface of the solid substrate, wherein the fusion domain is fused to the C-terminus of the S-layer protein, and wherein a plurality of S-layer fusion proteins are capable of self-assembly into a two-dimensional crystal lattice on a surface;
   ii. the variant GPCR fusion protein comprises a variant GPCR and a binding moiety;
   wherein the variant GPCR is a water-soluble variant of a native GPCR, wherein a plurality of amino acid residues Leucine (L), isoleucine (I), valine (V), and phenylalanine (F) within the seven-transmembrane a-helical domain of the native GPCR are replaced with glutamine (Q), threonine (T), threonine (T), and tyrosine (Y), respectively; and
   wherein the binding moiety is fused to the C-terminus of the variant GPCR, has binding affinity for the fusion domain of the S-layer fusion protein, and further wherein the binding moiety is bound to the fusion domain.

\* \* \* \* \*